(12) United States Patent
Chapman et al.

(10) Patent No.: US 9,506,078 B2
(45) Date of Patent: *Nov. 29, 2016

(54) ENGINEERING LIPIDS IN VEGETATIVE TISSUES OF PLANTS

(71) Applicants: University of North Texas, Denton, TX (US); Board of Regents, The University of Texas System, Austin, TX (US)

(72) Inventors: Kent D. Chapman, Denton, TX (US); Richard G. W. Anderson, Dallas, TX (US)

(73) Assignees: Board of Regents, The University of Texas System, Austin, TX (US); University of North Texas, Dentons, TX (US)

( * ) Notice: Subject to any disclaimer, the term of this patent is extended or adjusted under 35 U.S.C. 154(b) by 593 days.

This patent is subject to a terminal disclaimer.

(21) Appl. No.: 13/966,019

(22) Filed: Aug. 13, 2013

(65) Prior Publication Data

US 2014/0075591 A1 Mar. 13, 2014

Related U.S. Application Data

(63) Continuation of application No. 12/696,037, filed on Jan. 28, 2010, now Pat. No. 8,507,754.

(60) Provisional application No. 61/148,952, filed on Jan. 31, 2009.

(51) Int. Cl.
  *C12N 15/82* (2006.01)
  *C12N 5/14* (2006.01)
  *A01H 5/00* (2006.01)

(52) U.S. Cl.
  CPC ............. *C12N 15/8247* (2013.01); *A01H 5/00* (2013.01)

(58) Field of Classification Search
  None
  See application file for complete search history.

(56) References Cited

U.S. PATENT DOCUMENTS

| 8,507,754 B2 * | 8/2013 | Chapman | A01H 5/00 554/8 |
|---|---|---|---|
| 2007/0174932 A1 | 7/2007 | Uwer et al. | |
| 2007/0277269 A1 * | 11/2007 | Alexandrov | C07K 14/415 800/290 |

FOREIGN PATENT DOCUMENTS

WO  WO 2007/135386  11/2007

OTHER PUBLICATIONS

Bouvier-Nave et al. (Eur. J. Biochem. (2000) 267: 85-96).*
Alonso et al (Science (2003) 301: 653-657).*
Robert et al (Func. Plant Biol. (2005) 32: 473-479).*
The Arabidopsis Information Resource webpage for At4g24160 (http://www.arabidopsis.org/servlets/TairObject?type=locus&id=129481). No date is available for the webpage.*
The Arabidopsis Information Resource Webpage for At4g24160 (http://www.arabidopsis.org/servlets/TairObject?type=locus&id=129481). Date last modified: Feb. 11, 2013. Already of record. See NPL file mailed on Mar. 2, 2016.*
Abell et al., "Membrane topology and sequence requirements for oil body targeting of oleosin," *Plant J.*, 37:461-470, 2004.
Alonso et al., "Genome-wide insertional mutagenesis of *Arabidopsis thaliana*," *Science*, 301:653-657, 2003.
Blokland et al., "Transgene-mediated suppression of chalcone synthase expression in *Petunia hybrida* results from an increase in RNA turnover," *Plant J.*, 6:861-877, 1994.
Bouvier-Nave et al., "Expression in yeast and tobacco of plant cDNAs encoding acyl CoA:diacylglycerol acyltransferase," *Eur. J. Biochem*, 267:85-96, 2000.
Capuano et al., "Properties and exploitation of oleosins," *Biotechnol. Adv.*, 25:203-206, 2007.
Cernac et al., "WRINKLED1 encodes an AP2/EREB domain protein involved in the control of storage compound biosynthesis in arabidopsis," *Plant J.*, 40:575-585, 2004.
Chapman et al., "Reduced oil accumulation in cottonseeds transformed with a brassica nonfunctional allele of a delta-12 fatty acid desaturase (FAD2)," *Crop Sci.*, 48:1470-1481, 2007.
Friedberg, "Automated protein function prediction—the genomic challenge Brief," *Bioinformation*, 7:225-242, 2006.
GenBank Accession No. NM_118548, dated Aug. 21, 2009.
Ghosh et al., "At4g24160, a soluable acyl-coenzyme A-dependentl lysophosphatidic acid acyltransferase," *Plant Phys.*, 151:869-881, 2009.
Guo et al., "Leaf senescence: signals, execution, and regulation," *Current Topics in Devel. Biol.*, 71:83-112, 2005.
Guo et al., "Protein tolerance to random amino acid change," *PNAS*, 101:9205-9210, 2004.
Heath et al., "A conserved histidine is essential for glycerolipid acyltransferase catalysis," *J. of Bacteriology*, 180(6):1425-1430, 1998.
Hruz et al., "Genevestigator V3: a reference expression database for the meta-anaylsis of transcriptomes," *Adv. Bioinformation*, Article ID 420747, 2008.

(Continued)

*Primary Examiner* — Brent Page
*Assistant Examiner* — Matthew Keogh
(74) *Attorney, Agent, or Firm* — Dentons US LLP

(57) ABSTRACT

The present invention discloses gene targets and methods for the genetic control of lipid accumulation in vegetative (non-seed) portions of plants. Enhanced lipid, e.g. triacylglycerol (TAG), accumulation in vegetative portions of plants may be obtained by down-regulation of activity of At4g24160 or a homolog thereof. Plants, plant parts, seeds comprising down-regulated AT4G24160 activity, or activity of a homolog thereof, are also provided, as well as products prepared therefrom.

26 Claims, 30 Drawing Sheets

(56) References Cited

OTHER PUBLICATIONS

Kaup et al., "A role for diacylglycerol acyltransferase during leaf senescence," *Plant Physiology*, 129:1616-1626, 2002.

Lefevre et al., "Mutations in CGI-58, the gene encoding a new protein of the esterase/lipase/thioesterase subfamily in chanarin-dorfman syndrome," *Am. J. Hum. Genet.*, 69:1002-1012, 2001.

Markham et al., "Separation and identification of major plant sphingolipid classes from leaves," *JBC*, 281:22684-22694, 2006.

Mendoza et al., "Leafy Cotyledon 2 activation is sufficient to trigger the accumulation of oil and seed specific mRNAs in arabidopsis leaves," *FEBS Letters*, 579:4666-4670, 2005.

Munoz-Bertomeu et al., "Expression of spearmint limonene synthase in transgenic spike lavender results in an altered monoterpene composition in developing leaves," *Metobolic Engineering*, 10:166-177, 2008.

Murphy, "Structure, function and biogenesis of storage lipid bodies and oleosins in plants," *Prog. Liipid Res.*, 32(3):247-280, 1993.

Oberer et al., "Recent insights into the structure and function of comparative gene identification-58," *Current Opinion in Lipidology*, 22:149-158, 2011.

Rezzonico et al., "Level of accumulation of epoxy fatty acid in *Arabidopsis thaliana* expressing a linoleic acid delta12-epoxygenase is influenced by the availability of the substrate linoleic acid," *Theor App Genet*, 109:1077-1082, 2004.

Robert et al., "Metabolic engineering of *Arabidopsis* to produce nutritionally important DHA in seed oil," *Func. Plant Biol.*, 32:473-479, 2005.

Schrag et al., "Lipases and $\alpha/\beta$ Hydrolase Fold," *Methods in Enzymology*, 284:85-107, 1997.

Slocombe et al., "Oil accumulation in leaves directed by modification of fatty acid breakdown and lipid synthesis pathways," *Plant Biotechnology J.*, 7:694-703, 2009.

Stone et al., "Arabidopsis leafy cotyledon2 induces maturation traits and auxin activity: implications for somatic embryogenesis," *PNAS*, 105(8):3151-3156, 2008.

\* cited by examiner

```
atest_TC287358      ----------------AGTAGCAAACTTCTCGATTCCTTGATTCGTGGGAAAAAGAAA
bnest_TC15176       ----------------------------------------------------------
popuest_TC45316     ----------------------------------------------------------
ricest_TC302718     ------------------------------------AAGAACTCCGCCCAGAAGAAGA
wheatest_TC256052   --------------------------------------AAAACAANCGCGGCAGAGCCTACTC
potest_TC140557     GTGAAACCGGCGAAGGAGAGAATGAGGTTAAGTTTCTTGGAAAGGCAATAGAGAACTTGG
ricest_TC358735     ----------------------------------------------------------
onest_TC176         ----------------------------------------------------------
pinest_TC42098      ----------------------------------------------------------
spruest_TC31172     ----------------------------------------------------------
sorgest_TC95780     ----------------------------------------------------------
sugest_TC68544      ----------------------------------------------------------
maizest_TC285906    -GGGCCGCACCGACCGAACCTAACCGAGAGCACGAGCATACCCGTCCCGACTCCGACTGC
best_TC142187       ----------------------------------------------------------
tobest_TC12912      ----------------------------------------------------------
cottest_TC38615     ----------------------------------------------------------
vvest_TC65200       ----------------------------------------------------------
ljest_TC8785        ----------------------------------------------------------
soybest_TC229646    ----------------------------------------------------------
medicest_TC94860    ---------------------------------------------------------- atest_TC287358      GTCTAGATTTTTGTGGATTTTGATTTTGTGATTCCGTGATTGTATGAACTTGAGCCGTTT
bnest_TC15176       ----------------------------------------------------------
popuest_TC45316     -----------------------------GGCACGAGGATTT---CTATAT
ricest_TC302718     G-GCGACGAGAGTGAC-A-GGCCGAGGAGGGA--GGGGGATTCGAGGATCGCATGCGCCG
wheatest_TC256052   GTGTGACTACCCCTACCA-ATCTGCCCAGCAG--AGCCGGCGCGGGGG--GAACACGCTC
potest_TC140557     AGAACACTCTATCTAGCACATACGCCTATATTTTGGGGAGTTCAGCGACAAAAGGGGAAA
ricest_TC358735     ----------------------------------------------------------
onest_TC176         -------------------------------TCCAATTA--GACGGCTCTG
pinest_TC42098      -----------------------------AGCTGAGGCCCAAAACATGATATAAAGACCAA
spruest_TC31172     ----------------------------------------------------------
sorgest_TC95780     ----------------------------------------------------------
sugest_TC68544      ----------------------------------------------------------
maizest_TC285906    AGAGCATCAGCCGAGGAGAAAAGTCGGGAGAAACGCGCGTGACGTCTGCCCGCGTCGTAT
best_TC142187       ----------------------------------------------------------
tobest_TC12912      ----------------------------------------------------------
cottest_TC38615     ----------------------------------------------------------
vvest_TC65200       ----------------------------------------------------------
ljest_TC8785        ----------------------------------------------------------
soybest_TC229646    ----------------------------------------------------------
medicest_TC94860    -------------------------------GGTTGGCTCATAGTTCCTTTTACC
```

```
atest_TC287358     TGCTTCGAGATTAAGAATGGCGGAAGAAATCTCAAAGACGAAGGTGGGATCTTCTTCTAC
bnest_TC15176      ------------------------------------------------------------
popuest_TC45316    GATTTTATGAACCCGTTTCGTTCACGCG-TCTCAAGCTCAATAGTA------TCTAACAT
ricest_TC302718    TGCCGCCGCCGCC-GCCGTGACGGTGACGACGACG-ACGAGGATGGCGGCGGAGGGGATG
wheatest_TC256052  GCTCGCTCGCGCC-GCGTTGCATGCGCCG--GGCA-GCCGCCGCCGCCACCACCAGGAT-
potest_TC140557    TTAATTATCTGTT-GCATCAATCGCATGAGCATCGGACTAAGGAGGTTATCGAATTCATT
ricest_TC358735    ------ATGGTTT-GTGTTAGTTACAAGA--TACAACCTCCTAAGGTTGTATTAATTGTT
onest_TC176        GTACTTTCCTACT-TAATTGTTAATTAGGG-AACG-AAAATTGGAATGATCAGATTTAGT
pinest_TC42098     CAACACGGATGAC-ACTGCATTAATGGTCGATGAGCACTCGAATGCCCAGTAGATGGTCC
spruest_TC31172    ------------------------------------------------------------
sorgest_TC95780    ------------------------------------------------------------
sugest_TC68544     ------------------------------------------------------------
maizest_TC285906   GCGCCGCGCTGCCGTCGCCGCGACGACGACGACGACCAGGATGGCAGCCGAGGAGATGAG
best_TC142187      ------------------------------------------------------------
tobest_TC12912     ------------------------------------------------------------
cottest_TC38615    ------------------------------------------------------------
vvest_TC65200      ------------------------------------------------------------
ljest_TC8785       ------------------------------------------------------------
soybest_TC229646   ------------------------------------------------------------
medicest_TC94860   TGTTGAAAACAAAACATATGGAGTAACATTTTAGTCAGAAATTCAAAGCTACGCACTTGA atest_TC287358     TGCTTCGGTGGCTGATTCATCTGCTGCTGCGTCGGCTGCAACGAATGCGGCCAAATCAAG
bnest_TC15176      ------------------------------------------------------------
popuest_TC45316    GGGCGAAGAGCAAGGATCCTCTGCTTCCGCTTCCACCGCAACATCATCATCACGGGCAAA
ricest_TC302718    TCCACGGCCGCCGCGGCAG-CGGAGGCGACGGCGACGGCGGCGCCCGCGGCGGGGTCGAG
wheatest_TC256052  --CAGGATCGGGATGGCGG-TGGAGGAG---GTCAGGCAGGCGTCCGCGGCCG--CCACG
potest_TC140557    GGTAAAAATGGCGGAACAAATCAATTCATCAGCCGCCGATAACACAGCTGCCGGAGCAAA
ricest_TC358735    ----GGTGTGGTGTTTCTTCCTGGTTTTATGCTCTCAGCTATATTGTTAACAAATATACT
onest_TC176        ---------GCACGAAAAATGGCAGAAATGGCGACAGCTGAAACTACTTCTTCTTCACC
pinest_TC42098     AGAATGGCCGAAGAATTAGCTAAAGTCGA-AGCACCAGAGGTTGCCACCGGAAGTAGATC
spruest_TC31172    ------------------------------------------------------------
sorgest_TC95780    ------------------------------------------------------------
sugest_TC68544     ------------------------------------------------------------
maizest_TC285906   ACGGGCCTCCGCCTCAACGGCCACGGCGGAGATGCCGGCGTCGCCGGCGCCGGCGCAAGC
best_TC142187      ------------------------------------------------------------
tobest_TC12912     ------------------------------------------------------------
cottest_TC38615    ------------------------------------------------------------
vvest_TC65200      ------------------------------------------------------------
ljest_TC8785       ------------------------------------------------------------
soybest_TC229646   ------------------------------------------------------------
medicest_TC94860   TTAAACTAATTATCGAAAAATGGCGGAAGAAATTAGACAAAAGGACGACGTCGATTCATC
```

FIG. 9 (Cont.)

```
atest_TC287358      ATGGAAAATTTTGTGGCCTAATTCGCTC---CGGTGGATTCCTACGTCCACCGATTACAT
bnest_TC15176       ------------------------------------------------------------
popuest_TC45316     AACAAGATCTACATGGCCCTCTATTCTT---CGCTGGATCCCCACTTCCACCGATCACGT
ricest_TC302718     GTGGGGGAGGGCGTGGCCGTCCGCGCTG---CGCTGGATCCCGACCTCCACCGACCGCAT
wheatest_TC256052   GCGGCCGAGGCCG----CGTCCGCGTCGG--CGCTGGATCCCCACCTCCACCGAACGCAT
potest_TC140557     ACGGTGGTCATTTTGGCCCTCTTCTCTT---CGTTGGATACCTACATCTACTGACCACAT
ricest_TC358735     TCAGTTCTTTCTT---CATTTTGCTCTA------GATATATCTGAGGCTCTTTGCAATTT
onest_TC176         AGCATCTACTTCAAGATGGAATTGGCTT---CGATGGATTCCGACCTCTACTGATCATAT
pinest_TC42098      GTGGTCTATCCTTCGTTGGCCTCCTGCTCTCAGATGGATTCCCACCTCCATCAAAGAAGT
spruest_TC31172     ------------------------------------------------------------
sorgest_TC95780     ------------------------------------------------------------
sugest_TC68544      ------------------------------------------------------------
maizest_TC285906    GGGGTCGAGGTGGGCGCGGGTGTGGCCGCGCGCGCTCCGGTGGATCCCCACCTCCACGGA
best_TC142187       ------------------------------------------------------------
tobest_TC12912      ------------------------------------------------------------
cottest_TC38615     ------------------------------------------------------------
vvest_TC65200       ------------------------------------------------------------
ljest_TC8785        ------------------------------------------------------------
soybest_TC229646    ------------------------------------------------------------
medicest_TC94860    TTCGAAATCTAAAAGCTTCTGGTCTTCACTCCGTTGGATTCCCACTTCTACCGATCATAT atest_TC287358      CATCGCCGCCGAGAAACGTCTTCTCTCCATCCTCAAGACGCCTTATGTACAAGAGCAAGT
bnest_TC15176       ------------------------------------------------------------
popuest_TC45316     CATCGCTGCCGAAAAACGCCTTTTCTCTCTAGTCAAGACTCCGTACGTGGTAGAGCAAGT
ricest_TC302718     CATCGCCGCCGAGAAGCGGCTCCTCTCCATAGTCAAAACTGGCTATGTCCAAGAACAAGT
wheatest_TC256052   CATCGCCGCAGAGAAGCGACTCCTCTCCATCCTCAAAACTGGGTATGTCCAAGAACAAGT
potest_TC140557     CATCGCTGCTGAAAAACGTCTTCTTTCTCTTGTTAGGACTCCTTATACACAAGAGCAGGT
ricest_TC358735     TCTAATTGGTGGTGCACTTTTTATATCTCTTTACAGAACTGGCTATGTCCAAGAACAAGT
onest_TC176         CATCGCTGCCGAGAAACGCCTCCTCTCTATAGTCAAAACTGGATATGTACAAGAGAAGGT
pinest_TC42098      CCTTGCCTCCGAACGCAGTCTCCTTTCCCTCGTCAAGACTCCCTATGTGGAAGAGGAGGT
spruest_TC31172     ------------------------------------------------------------
sorgest_TC95780     ------------------------------------------------------------
sugest_TC68544      ------------------------------------------------------------
maizest_TC285906    CCGCATCATCGCCGCCGAGAAGCGACTCCTCACGATAGTCAAAACTGGATATGTCCAGGA
best_TC142187       ------------------------------------------------------------
tobest_TC12912      ------------------------------------------------------------
cottest_TC38615     ------------------------------------------------------------
vvest_TC65200       ------------------------------------------------------------
ljest_TC8785        ------------------------------------------------------------
soybest_TC229646    ------------------------------------------------------------
medicest_TC94860    CATCGCCGCTGAGAAACGCCTTCTTTCCATTATCAAGACTGGGTATGCTCAAGAGCATGT
```

FIG. 9 (Cont.)

```
atest_TC287358      CAGTATTGGTTCAGGACCACCAGGTTCTAAAATCAGGTGGTTTAGGTCTACGAGCAATGA
bnest_TC15176       ------------------------------------------------------------
popuest_TC45316     GAATATTGGTTCGGGTCCACCAGGGTCGAAGACTCGGTGGTTTCGATCTAAGAGTGATGA
ricest_TC302718     TAACATTGGCTCCTCTCCACCCGGATCAAAAGTTAGATGGTTTAGATCATCAAGTGATGA
wheatest_TC256052   CAACATTGGCTCTGCTCCACCTGGGTCAAAAGTAAAATGGTTTAGATCATCAAGTGATGA
potest_TC140557     CAACATTGGGTCTGGTCCACCAGGTTCAAAAGTTAGATGGTTTCGATCGGTGAGCAATGA
ricest_TC358735     TAACATTGGCTCCTCTCCACCCGGATCAAAAGTTAGATGGTTTAGATCATCAAGTGATGA
onest_TC176         AAATATTGGTTCTGGACCGCCCGGGTCAAAAATTAGATGGTTCAGGTCATCCAGTGATGA
pinest_TC42098      CAATATTGGTAGCGGGCCACCTGGATCGAAGGTAAGATGGTTCAGGTCTTCAAGCAACGA
spruest_TC31172     ----------------------------------------------------AAGCAACAA
sorgest_TC95780     ------------------------------------------------------------
sugest_TC68544      ------------------------------------------------------------
maizest_TC285906    ACGAGTCAACATTGGCTCTGCTCCACCTGGGTCAAAAGTAAGATGGTTTAGGTCAGCAAG
best_TC142187       ------------------------------------------------------------
tobest_TC12912      ------------------------------------------------------------
cottest_TC38615     ------------------------------------------------------------
vvest_TC65200       ------------------------------------------------------------
ljest_TC8785        ------------------------------------------------------------
soybest_TC229646    ------------------------------------------------------------
medicest_TC94860    TAATATAGGTTCTGGTCCTCCTGGCTCTAAAGTTAGATGGTTCCGTTCAACCAGTAACGA atest_TC287358      GTCACGTTACATCAACACTGTTACATTTGA--TGCCAAGGAG----GGAGCTCCTACACT
bnest_TC15176       ------------------------------------------------------------
popuest_TC45316     GCCTAGGTTTATCAATACGGTGACTTTTCA--AAGCAAAGAG----GATTCTCCTACGCT
ricest_TC302718     GCCAAGATTCATCAATACTGTAACATTTGA--TAGCGAAGAA----AATGCTCCCACCCT
wheatest_TC256052   GCCAAGGTTCATCAATACAGTGACATTTGA--TAGCAAGGAG----AATGCTCCCACCCT
potest_TC140557     ACCGAGATTTATCAATACTGTTACTTTCGA--CAGCAAAGAG----GGTTCTCCTACTCT
ricest_TC358735     GCCAAGATTCATCAATACTGTAACATTTGA--TAGCGAAGAA----AATGCTCCCACCCT
onest_TC176         CTCGAGATTTATAAATACGGTTACTTTTGA--TAGCAAGGAC----GATGCTCCGACTTT
pinest_TC42098      GCCGCGCTTCATACACACTGTTACCTATGAGACTGCCGAAAACAGCAAAGCACCGACCTT
spruest_TC31172     GCCGCGCTTCATACATACTATTACCTACGAGTCTGCCAAGAACAGCAACGCACCGACTTT
sorgest_TC95780     ------------------------------------------------------------
sugest_TC68544      ------------------------------------------------------------
maizest_TC285906    TGATGAACCAAGGTTCATTAATACTGTAACATTTGATAGCAAGGAGAATGCCCCCACCCT
best_TC142187       ------------------------------------------------------------
tobest_TC12912      ------------------------------------------------------------
cottest_TC38615     ------------------------------------------------------------
vvest_TC65200       ------------------------------------------------------------
ljest_TC8785        ------------------------------------------------------------
soybest_TC229646    ------------------------------------------------------------
medicest_TC94860    GCCACGCTTTCTCAACACTGTTACATTTGATAGTAAACCCGA------TTCTCCTACACT
```

FIG. 9 (Cont.)

```
atest_TC287358     CGTCATGGTTCATGGTTATGGTGCTTCTCAAGGGTTTTTCTTCCGTAATTTTGATGCTCT
bnest_TC15176      ------------------------------------------------------------
popuest_TC45316    TGTAATGGTCCATGGATATGGTGCTTCTCAAGGTTTTCTTCTTCAGGAATTTTGATGCTCT
ricest_TC302718    TGTCATGGTCCATGGGTATGGTGCTTCACAGGGTTTCTTCTTTCGAAACTTTGATGCCCT
wheatest_TC256052  TGTCATGGTCCATGGTTATGGTGCGTCACAGGGGTTCTTCTTTAGAAACTTTGATGCCCT
potest_TC140557    TGTTATGGTCCATGGATATGGTGCCTCTCAAGGTTTCTTCTTTCGGAATTTTGCTGCCCT
ricest_TC358735    TGTCATGGTCCATGGGTATGGTGCTTCACAGGGTTCTTCTTTCGAAACTTTGATGCCCT
onest_TC176        AGTCATGGTACATGGTTATGGTGCTTCTCAGGGGTTTTTCTTTCGAAACTTTGATGCTTT
pinest_TC42098     GGTGATGGTTCATGGCTACGGGGCTTCCCAGGGCTTCTTCTTCCGGAACTTCGATGCACT
spruest_TC31172    GGTGATGGTTCATGGCTACGGGGCTTCCCAGGGCTTCTTCTTCCGGAACTTCGATGCACT
sorgest_TC95780    ------------------------------------------------------------
sugest_TC68544     ------------------------------------------------------------
maizest_TC285906   GGTTATGGTCCATGGCTATGGAGCTTCACAGGGGTTCTTCTTTCGAAACTTTGATGCCCT
best_TC142187      ------------------------------------------------------------
tobest_TC12912     ------------------------------------------------------------
cottest_TC38615    ------------------------------------------------------------
vvest_TC65200      ------------------------------------------------------------
ljest_TC8785       ------------------------------------------------------------
soybest_TC229646   ------------------------------------------------------------
medicest_TC94860   TGTTATGGTTCATGGATACGCTGCTTCTCAGGGTTTCTTCTTTCGCAATTTTGATGCTCT atest_TC287358     TGCCAGTCGATTTAGAGTGATCGCTATTGATCAACTTGGGTGGGGTGGTTCAAGTAGGCC
bnest_TC15176      ------------------------------------------------------------
popuest_TC45316    TGCTAGTCGTTTCAAGATCATTGCTATTGATCAGCTTGGTTGGGGTGGATCAAGTAGACC
ricest_TC302718    TGCAAGCCGTTTCAGGGTGATTGCCATTGATCAGCTTGGTTGGGGTGGATCAAGTAGACC
wheatest_TC256052  TGCAAGCCGTTTCCGGGTGATTGCCATTGACCAGCTTGGTTGGGGTGGATCAAGCAGACC
potest_TC140557    TGCAAAGCATTTCAAAGTAATTGCTATTGATCAGCTTGGCTGGGGTGGATCAAGCAGGCC
ricest_TC358735    TGCAAGCCGTTTCAGGGTGATTGCCATTGATCAGCTTGGTTGGGGTGGATCAAGTAGACC
onest_TC176        GGCCAGTCGCTTTCGAGTTATTGCCATTGATCAGCTCGGTTGGGGTGGCTCAAGTCGTCC
pinest_TC42098     CGCCAGTCGCTTCAGGGTTATTGCCATCGACCAATTGGGATGGGGTGCCTCAAGTCGACC
spruest_TC31172    CGCCAGTCGCTTTAGGGTTATTGCCATCGACCAATTGGGATGGGGTGCCTCAAGTCGACC
sorgest_TC95780    ------------------------------------------------------------
sugest_TC68544     ------------------------------------------------------------
maizest_TC285906   TGCAAGCCGTTTTAGGGTGATTGCCATTGATCAGCTTGGCTGGGGTGGTTCAAGCAGACC
best_TC142187      ---------------------------------CGGACGAGGGGATCAAACAGACC
tobest_TC12912     ------------------------------------------------------------
cottest_TC38615    ------------------------------------------------------------
vvest_TC65200      ------------------------------------------------------------
ljest_TC8785       ------------------------------------------------------------
soybest_TC229646   ------------------------------------------------------------
medicest_TC94860   CGCCTCTCGTTTCAGAATCATTGCTGTTGATCAACTTGGTTGGGGAGGATCAAGCAGACC
```

FIG. 9 (Cont.)

```
atest_TC287358      TGATTTTACATGTAGAAGCACAGAAGAAACTGAGGCATGGTTTATCGACTCCTTTGAGGA
bnest_TC15176       ----------------------AACGGAGGCGTGGTTTATCGATTCATTTGAGGA
popuest_TC45316     TGACTTTACCTGCAAAAGCACTGAAGAAACTGAGGCGTGGTTTATTGACTCCTTTGAGGA
ricest_TC302718     TGACTTCACTTGTAAAAGTACTGAAGAAACTGAGGCATGGTTCATAGATTCCTTTGAGGA
wheatest_TC256052   TGACTTTGACTGTAGAAGTACTGAAGAAACCGAGGCTTGGTTCATAGATTCTTTTGAGGA
potest_TC140557     TGACTTCACATGCAAAAGTACCGAAGAGACTGAAAATTGGTTTATTGATTCCTTTGAGGA
ricest_TC358735     TGACTTCACTTGTAAAAGTACTGAAGAAACTGAGGCATGGTTCATAGATTCCTTTGAGGA
onest_TC176         AGACTTTACTTGCAAAAGCACGGAAGAAACGGAAACCTGGTTTATTGATTCATTTGAGGC
pinest_TC42098      TGACTTTACCTGTAAAAGCACAGAAGAAACTGAAGCCTGGTTCATTGATTCATTCGAAGA
spruest_TC31172     TGACTTCACCTGTAAAAGCACAAAAGAAACTGAAGCCTGGTTCATTGATTCATTTGAAGA
sorgest_TC95780     ------------------------------------------------------------
sugest_TC68544      ------------------------------------------------------------
maizest_TC285906    TGACTTCACATGTAAAAGTACCGAAGAAACTGAGGCATGGTTCATAGATTCTTTCGAGGA
best_TC142187       TGACTTCGACTGTAGAAGTACTGAAGAAACCGAGGCTTGGTTCATAGATTCTTTTGAGGA
tobest_TC12912      -------------------------CTGAAGATTGGTTTATTGATTCCTTTGAGGA
cottest_TC38615     ------------------------------------------------------------
vvest_TC65200       ------------------------------------------------------------
ljest_TC8785        ------------------------------------------------------------
soybest_TC229646    ------------------------------------------------------------
medicest_TC94860    TGATTTCACATGCAAAAGTACCGAAGAAACTGAGGCATGGTTCATTGATTCTTTCGAGGA atest_TC287358      ATGGCGTAAAGCCCAGAATCTCAGTAACTTTATTCTATTAGGACATTCTTTTGGAGGCTA
bnest_TC15176       ATGGCGTAAGTCTAAGAATCTCAGTAACTTCATTCTGTTAGGACATTCTTTTGGAGGTTA
popuest_TC45316     ATGGCGAAAAGCAAAGAACCTCAGTAACTTCATATTGCTTGGGCATTCATTTGGAGGGTA
ricest_TC302718     ATGGCGCAAAGCAAAGAATCTCAGTAATTTTATATTGCTCGGTCACTCTTTTGGAGGATA
wheatest_TC256052   ATGGCGCAAAGCAAAAAACCTCAGTAATTTTATATTGCTTGGTCATTCTTTCGGAGGATA
potest_TC140557     GTGGCGCAAAGCCAAAAATCTTAGCAACTTTATTTTGCTTGGGCACTCTTTTGGAGGGTA
ricest_TC358735     ATGGCGCAAAGCAAAGAATCTCAGTAATTTTATATTGCTCGGTCACTCTTTTGGAGGATA
onest_TC176         ATGGCGTAAATCCAAAAACTTGAGTAACTTCATTTTGCTTGGGCATTCTTTTGGAGGATA
pinest_TC42098      ATGGCGTAAAGCTAAAAACTTGGATCAGTTTATTTTGCTAGGTCATTCTTTTGGAGGTTA
spruest_TC31172     ATGGCGTAAAGCCAAAAACTTGGATCAGTTTATTTTGCTAGGTCACTCTTTTGGAGGTTA
sorgest_TC95780     ------------------------------------------------------------
sugest_TC68544      ------------------------------------------------------------
maizest_TC285906    GTGGCGCAAGGCCAAGAACCTCAGTAATTTTATATTGCTTGGTCACTCTTTTGGAGGATA
best_TC142187       ATGGCGCAAAGCAAAGAACCTCAGTAATTTTATATTGCTCGGTCATTCTTTCGGAGGATA
tobest_TC12912      GTGGCGCAAAGCCAAAAACCTTAGCAACTTTATTTTGCTTGGGCACTCTTTTGGAGGGTA
cottest_TC38615     ------------------------------------------------------------
vvest_TC65200       ------------------------------------------------------------
ljest_TC8785        ------------------------------------------------------------
soybest_TC229646    ------------------------------------------------------------
medicest_TC94860    ATGGAGAAAAGCCAAAAATCTTACCAATTTCATACTGCTTGGACATTCTTTTGGTGGTTA
```

FIG. 9 (Cont.)

```
atest_TC287358      TGTTGCTGCTAAATACGCGCTTAAGCATCCTGAACATGTTCAACACTTAATTCTGGTGGG
bnest_TC15176       TGTTGCTGCTAAGTACGCGCTTAAGCACCCTGAGCATGTTCAGCACTTGGTTCTGGTGGG
popuest_TC45316     TGTTGCGGCTAAATATGCACTCAAGCATCCCGAGCGTGTTAAGCAGTTGATTTTAGTGGG
ricest_TC302718     TGTTGCGGCAAAGTACGCTTTACAGCATCCTGAGCACGTCCAACACTTGATCTTGGTCGG
wheatest_TC256052   TGTTGCGGCAAAGTATGCCTTACAGCATCCTGAACATGTTCAGCACTTGATTTTGGTTGG
potest_TC140557     TGTCACTGCCAAATATGCTCTCAAGCATCCTGAGCATGTTCAGCAGTTGATTCTGGTAGG
ricest_TC358735     TGTTGCGGCAAAGTACGCTTTACAGCATCCTGAGCACGTCCAACACTTGATCTTGGTCGG
onest_TC176         CGTGGCTGCAAAATATGCTCTGAAGCACCCTGAGCATGTCCAACATTTAATATTGGTGGG
pinest_TC42098      TGTGGCTGCAAAATATGCTCTGAAGTATCCAGAGCATGTCAGGCACCTAATATTGGTAGG
spruest_TC31172     TGTGGCTGCAAAATATGCTATTAAGTATCCAGAGCATGTTAAGCACCTAATATTGGTAGG
sorgest_TC95780     ---------------------------ACACATTCAGCACTTAGTTTTGGTTGG
sugest_TC68544      ------------------------------------------------------------
maizest_TC285906    TGTTGCTGCAAAATATGCGCTAAAGCACCCTGAACACGTTCAACAGTTGATTTTGGTTGG
best_TC142187       TGTTGCGGCAAAGTATGCGTTACAGCATCCTGAACATGTTCAGCACTTGATTTTGGTTGG
tobest_TC12912      TGTCGCTGCAAAATATGCTCTCAAGCATCCAGAGCATGTTCAGCAGTTGATTCTGGTAGG
cottest_TC38615     ------------------------------------------------------------
vvest_TC65200       ------------------------------------------------------------
ljest_TC8785        ------------------------------------------------------------
soybest_TC229646    ------------------------------------------------------------
medicest_TC94860    TGTTGCTTCCAAATACGCGCTCAAGCACCCTCAGCACGTACAACACTTAATTTTGGTGGG atest_TC287358      ATCTGCTGGGTTCTCAGCAGAAGCAGATGCCAAATCAGAATGGCTCACTAAATTTAGAGC
bnest_TC15176       ATCTGCTGGTTTCTCAGCAGAATCACATGCCAAGTCGGAGTGGCTCACTAAGTTTAGAGC
popuest_TC45316     ATCTGCTGGATTTTCATCAGAATCAGATTCCAAGTCTGAGTGGCTCGCCCAATTTAGGGC
ricest_TC302718     CCCTGCTGGCTTTTCATCAGAAACAGAGCATAGCTCTGAGTGGTTAACCAAGTTCCGAGC
wheatest_TC256052   TTCTGCTGGCTTTTCGTCAGAAACAGATCATAGTTCTGAGTGGTTAACCAAGTTCCGTGC
potest_TC140557     ACCAGCCGGATTTACATCACAAACTGGACATATGTCTGAAC-------------------
ricest_TC358735     CCCTGCTGGCTTTTCATCAGAAACAGAGCATAGCTCTGAGTGGTTAACCAAGTTCCGAGC
onest_TC176         CCCTGCAGGCTTCACGTCAGAAACGGAACATAAATCAGAATGGTTGACTAAATTCAGAGC
pinest_TC42098      CTCAGCTGGATTCTCTGACGAGTCAAATAAAAAGGCTGAGTGGGTAACACAATTTAAATC
spruest_TC31172     CCCAGCTGGATTCTCCGACGAGTCAAATAAAAAGGCTGAGTGGATAACACAATTTAGAAC
sorgest_TC95780     TCCTGCTGGCTTCTCGTCAGAAACAGACCATAGCTCTGAGTGGTTAACCAAGTTTCGAGC
sugest_TC68544      ------------------------------------------------------------
maizest_TC285906    TCCTGCTGGCTTCTCATCAGAAACAGAGCATAGCTCTGAGTGGTTAACCAAGTTTCGAGC
best_TC142187       TTCTGCTGGCTTTTCATCAGAAACAGATCATAGTTCTGAGAGGTTAACCAAGTTCCGTGC
tobest_TC12912      ACCAGCTGGATTTACATCAGAGACTGAACATATGTCCGAGCGGCTTACCCAGTTTAGAGC
cottest_TC38615     ------------------------------------------------------------
vvest_TC65200       ------------------------------------------------------------
ljest_TC8785        ------------------------------------------------------------
soybest_TC229646    ------------------------------------------------------------
medicest_TC94860    ACCTGCCGGGTTTACAGAAGAAACAGATCCAAAGACTGAGTTTGTTACTAAGTTTCGAGC
```

FIG. 9 (Cont.)

```
atest_TC287358    AACATGGAAAGGTGCAGTCCTAAATCATTTATGGGAGTCAAATTTCACTCCTCAGAAGCT
bnest_TC15176     AACGTGGAAAGGTGCTCTTCTAAATCATCTATGGGAGTCCAATTTCACTCCTCAGAAGCT
popuest_TC45316   AACTTGGAAAGGAGCCATTTTGAATCATTTGTGGGAGTCTAATTTTACTCCTCAGAAGGT
ricest_TC302718   TACATGGAAAGGCATGCTAGTGAATCATCTATGGGAGTCCAATTTTACTCCTCAAAGAAT
wheatest_TC256052 AACGTGGAAAGGCATGCTAGTAAACCATCTTTGGGAGTCCAATTTCACTCCTCAGAGAAT
potest_TC140557   ------------------------------------------------------------
ricest_TC358735   TACATGGAAAGGCATGCTAGTGAATCATCTATGGGAGTCCAATTTTACTCCTCAAAGAAT
onest_TC176       CACTTGGAAAGGAGCTATTTTCAATCATCTCTGGGAATCCAACTTTACTCCTCAGAAAGT
pinest_TC42098    AACATGGAAGGGTGCAATATTAAATCATCTTTGGGAATCTAACTTCACTCCACAAAAGTT
spruest_TC31172   AACATGGAAGGGTGTAATATTAAATCATCTTTGGGAATCTAACTTCACTCCACAAAAGTT
sorgest_TC95780   AACATGGAAAGGCATGCTAGTGAATCATCTTTGGGAGTCCAATTTTACTCCCCAAAGAGT
sugest_TC68544    ------------------TAGTGAATCATCTTTGGGAGTCCAATTTTACTCCCCAAAGAGT
maizest_TC285906  AACATGGAAAGGCATGCTAATGAATCGTCTTTGGGAGTCCAATTTTACTCCCCAAAGGGT
best_TC142187     AACGTGGAAAGGCATGCTAGTAAACCATCTTTGGGAGTCCAATTGTACTCCTCAAAGAAT
tobest_TC12912    AACATGGAAGGGAGCCGTCTTGAATCATCTGTGGGAGTCTAACTTTACCCCGATGAAACT
cottest_TC38615   ---------GGGGGCAATTTTGAGTCATTTGTGGGAGTCTAATTTTACTCCTCAGAAGAT
vvest_TC65200     ------------------------------------------------------------
ljest_TC8785      ------------------------------------------------------------
soybest_TC229646  ---------------GTTTTGAACCATCTTTGGGAATCAAATTTCACACCTCAGAAACT
medicest_TC94860  AACATGGAAGGGAGCAGTTCTGAACCATCTATGGGAATCTAATTTTACACCTCAGAAAAT atest_TC287358    GGTTAGAGGATTAGGTCCTTGGGGTCCAGGTCTTGTAAATCGGTATACAACTGCAAGATT
bnest_TC15176     GATTAGAGGATTAGGTCCTTGGGGTCCGGGTCTTGTGAACCGGTATACAAGTGCAAGATT
popuest_TC45316   TGTCAGAGGGTTGGGTCCTTGGGGTCCTGGTCTGGTACGTCGCTACACAACTGCTAGATT
ricest_TC302718   AGTGAGAGGATTGGGTCCTTGGGGACCAGGCTTAGTTCAGAGATATACCAGTGCCAGATT
wheatest_TC256052 TGTGAGAGGATTAGGTCCTTGGGGCCCAGATTTAGTTCGGAGATATACCACTGCTAGGTT
potest_TC140557   ------------------------------------------------------------
ricest_TC358735   AGTGAGAGGATTGGGTCCTTGGGGACCAGGCTTAGTTCAGAGATATACCAGTGCCAGATT
onest_TC176       TATTAGAGGTTTAGGACCATGGGGCCCAGATATGGTACGAAGATATACTAGTGCTAGATT
pinest_TC42098    TGTTCGGAGTCTAGGGCCTTGGGGTCCACGTATAGTAAAAGGATATACAAGTGTTCGGTT
spruest_TC31172   TGTTCGGGGTCTAGGGCCTTGGGGTCCACGTATAGTGAACGGATATACAAGTGCTCGGTT
sorgest_TC95780   TATTAGAGGATTGGGCCCTTGGGGTCCAGGTCTAGTACAAAGATATACCAGTGCCAGGTT
sugest_TC68544    TATTAGAGGATTGGGTCCTTGGGGTCCAGGTCTAGTACGAAGATATACCAGTGCCAGGTT
maizest_TC285906  TATTAGGGGATTGGGTCCTTGGGGTCCAGGTCTAGTACAAAGATATACCAGTGCCAGGTT
best_TC142187     TGTGAGAGGATTGGGTCCTTGGGGTCCTGATTTAGTTCGGAAATATACCACTGCTAGGTT
tobest_TC12912    TGTCAGAGGCTTAGGCCCATGGGGTCCAGACCTAGTTCGCAAATACACTAATGCTAGATT
cottest_TC38615   TATAAGAGGNTTAGGTCCTTGGGGTCCAGATCTTGTACGGAAGTATACAGCTGCTAGGTT
vvest_TC65200     ---------------------------------------------GTACAAGTGCTAGATT
ljest_TC8785      ------------------------------------------------------------
soybest_TC229646  TGTCAGGGGTTTAGGTCCTTGGGGTCCCAACATAGTCCGCAAGTATACAAGTGCTAGGTT
medicest_TC94860  TGTCAGAGGTTTAGGTCCTTGGGGTCCTAACATGGTCCGCAAATATACAAGTGCTAGGTT
```

FIG. 9 (Cont.)

```
atest_TC287358    TGGTGC---ACATTCGGAGGGAACTGGGCTAACAGAAGAGGAAGCCAAATTGCTAACCGA
bnest_TC15176     TGGAGC---ACATTCGGTGGGAACTGTGCTAACAGATGAGGAGTCCAGATTGCTCACCGA
popuest_TC45316   TGGTGC---ATATTCAACCGGAGTAGTATTGGCTGAGGAGGAGTCCAAATTGCTAACAGA
ricest_TC302718   TGGCTC---ACATTCAACAGGTGAATTACTAACAGAACAGGAATCCACATTACTGACAGA
wheatest_TC256052 TGGCTC---ACATTCAACAGGTGAATTACTAACAGAAAACGAGTCCTCCTTGCTGACAGA
potest_TC140557   ------------------------------------------------------------
ricest_TC358735   TGGCTC---ACATTCAACAG----------------------------------------A
onest_TC176       TGGTTC---TTATTCTAATGGCACCACATTGACAGATGAGGAGTCAGCTTTGCTTACAGA
pinest_TC42098    TGTGAC---CCGTACAACTGGTGATACATTGAATGAAGTTGAGGCCAAATTGCTTTCAGA
spruest_TC31172   TGTAAC---TGGTTCGACTGGTGATATATTGAATGAAGTCGAGGCCAAACTGCTTTCGGA
sorgest_TC95780   TGGTAC---ACGTTCAACTGGTGATATACTAACAGATCAAGAATCAACATTGTTGACAGA
sugest_TC68544    TGGTAC---ACGTTCAACTGGTGAATTACTGACAGATCAAGAATCGACATTGTTAACAGA
maizest_TC285906  TGGTAC---AAGTTCTACTGGTGAATTACTAACAGATGAAGAATCGGCATTGATGACAGA
best_TC142187     TGGCTC---ACATTCAACAGGTGAATTACTAACAGAACATGAGTCCTCCTTACTGACAGA
tobest_TC12912    TACTGC---ATATTCTAATGGAGATAGTTTGACCGAGGAGGAGTCCAGGCTACTCTCAGA
cottest_TC38615   TACTAACAGATATTCACCTGAGGGTGTATTTACAGAGGAGGAGTCTAGACTTCTATCTGA
vvest_TC65200     TAGTTC---ATATTCAACTGGTGATTTGTTAACTGAAGAGGAGTCCAAGTTACTCACAGA
ljest_TC8785      ------------------------------TGACAGAATCTGAATCGACATTGCTGACAGA
soybest_TC229646  TGGTAC---ACATTCAACTGGGGAAATACTGACTGAAGAGGAATCAACATTGCTGACAGA
medicest_TC94860  TGGTAC---ACATTCAACCGGGCAAAAACTGATTGACGAGGAATCAAGTCTGCTGACTGA atest_TC287358    TTATGTGTACCATACTTTGGCTGCAAAGGCTAGTGGAGAGTTATGCTTGAAATACATCTT
bnest_TC15176     TTATGTGTATCATACGTTGGCTGCAAAGGCTAGTGGAGAGTTGTGCTTGAAATACATCTT
popuest_TC45316   TTATGTGTATCATACTTTAGCAGCCAAAGCTAGTGGAGAGCTATGCTTGAAATTTATATT
ricest_TC302718   TTACATTTACCATACTTTGGCTGCCAAAGCTAGTGGAGAGTTGTGCTTAAAACATATATT
wheatest_TC256052 TTACATTTACCACACTTTAGCTGCCAAAGCTAGTGGAGAGCTGTGCTTAAAACATATTTT
potest_TC140557   ------------------------------------------------------------
ricest_TC358735   TTACATTTACCATACTTTGGCTGCCAAAGCTAGTGGAGAGTTGTGCTTAAAACATATATT
onest_TC176       TTACATATACCACACTTTAGCTGCTAAAGCAAGTGGAGAACTGTGCTTGAAGTACATTTT
pinest_TC42098    TTATGTCTACCACACATTAGCTGCTAAAGCGTCTGGGGAGCTGTGTCTGAAGTATATATT
spruest_TC31172   TTATGTCTACCACACCTTAGCTGCTAAAGCATCTGGGGAGTTGTGTCTGAAGTATATATT
sorgest_TC95780   TTATATTTACCATACCTTAGCTGCCAAAGCTAGTGGAGAGCTGTGCTTGAAATATATATT
sugest_TC68544    TTATATTTACCATACCTTAGCTGCCAAAGCTAGTGGAGAGCTGTGCTTGAAATATATATT
maizest_TC285906  TTATATGTACCATACGTTAGCTGCCAAAGCTAGTGGAGAGCTGTGCTTGAAATATATATT
best_TC142187     TTACATTTACCACACTTTAGCTGCTAAAGCTAGTGGAGAGTTGTGCTTAAAACATATTTT
tobest_TC12912    TTATGTATATCATACCTTGGCTGCAAAACCGAGTGGGGAGCTATGTTTAAAATATATATT
cottest_TC38615   TTATGTGTACCATACCTCAGCTGCCAAAGCAAGTGGAGAGCTCTGCTTAAAATATATATT
vvest_TC65200     TTATGTGTACCATACTGTAGCAGCCAAAGCTAGTGGAGAGCTGTGCTTGAAATACATATT
ljest_TC8785      TTATCTTTACCACACAACAGCTGCCAAACCTAGTGGCGAGCTGTGCTTAAACTATATATT
soybest_TC229646  CTATGTTTACCACACATTGGCGGCCAAAGCTAGTGGAGAGCTGTGCTTAAAATATATTTT
medicest_TC94860  TTATGTTTATCATACATTGGCGGCCAAAGCTAGTGGGGAGCTGTGTTTAAAATATATTTT
```

FIG. 9 (Cont.)

```
atest_TC287358      CTCATTTGGAGC-ATTTGCTAGGAAGCCCCTCTTACAAAGTGCATCAGAGTGGAAAGTGC
bnest_TC15176       CTCCTTCGGAGC-ATTTGCTCGGAAGCCACTCTTACAAAGTGCATCAGAGTGGAAAGTGC
popuest_TC45316     TTCTTTTGGAGC-ATATGCACGGAAGCCCCTTTTACAGAGTGCATCAGAATGGAAAGTGC
ricest_TC302718     TTCCTTTGGGGC-ATTCGCGAGGAAACCTCTTCTGCAAAGGTCAGTTTTCTTCGTATTAA
wheatest_TC256052   TTCCTTGGGGGC-ATTTGCAAGGAAACCACTTCTGCACAGTGCATCCGACTGGAAAGTGC
potest_TC140557     ------------------------------------------------------------
ricest_TC358735     TTCCTTTGGGGC-ATTCGTGAGGAAACCTCTTCTGCAAAGTGCATCCGATTGGAAAGTGC
onest_TC176         TTCATTTGGAGC-ATTCGCACGGAAACCTCTTTTACAGAGTGCATCTGAGTGGAAAGTTC
pinest_TC42098      TGCTTTTGGAGC-ATTTGCTCGATCACCTCTTTTAAGAAGTGCCTCAGAATGGAAAGTAC
spruest_TC31172     TTCTTTTGGAGC-ATTTGCTCGATCACCTCTTTTAAAATGTGCACCAGAATGGAAGGTAC
sorgest_TC95780     TTCCTTCGGGGC-ATTTGCAAGGAAACCTCTTCTGCAGTGCGCATCCGATTGGAAAGTGC
sugest_TC68544      TTCCTTCGGGGC-ATTTGCAAGGAAACCTCTTCTGCAGTGCGCATCCGATTGGAAAGTGC
maizest_TC285906    TTCCTTCGGGGC-ATTTGCAAGGAAACCTCTTCTGCAGTGCGCGTCCGATTGGAAAGTGC
best_TC142187       CTCATTGGGGGC-ATTTGCAAGGAAACCACTTCTGCACAGTGCATCCGACTGGAAAGTGC
tobest_TC12912      TTCCTTCGGAGC-ATTTGCCAAGAGTCCTCTTTTATACAGAGCACCAGATTGGAAGGTGC
cottest_TC38615     TGCATTTGGAGC-ATTTAATCGGGCAC---TTTTAAACAGTGCATCTGAGTGGAAAGTGC
vvest_TC65200       TTCATTTGGAGCGATTTGATCGGTTGCCCCTTCTGCACAACGCATCAGAATGGAAAGTGC
ljest_TC8785        TTCATTTGGAGC-ATTCACCAAGTTGCCCCTTCTTCAAAGTGCCTCAGAGTGGAAGGTGC
soybest_TC229646    TTCATTTGGAGC-ATTTGCTAGGATGCCCCTTCTTCTCAGTGCCGCAGAGTGGAAGGTGC
medicest_TC94860    TGCATTTGGAGC-ATTTGCTAGGATGCCCCTTCTTCAAAGTGCTCAAGAGTGGAAGGTGC atest_TC287358      CAACAACGTTTATCTATGGAATGAATGATTGGATGAACTATCAAGGTGCGGTGGAAGCGA
bnest_TC15176       CAACAACTTTTATCTATGGAATGAATGATTGGATGAACTATCAAGGTGCAGTGGAAGCAC
popuest_TC45316     CAACCACTTTCATATATGGCTTCGAAGATTGGATGAGCTACGAAGGTGCCCAACAAGCTC
ricest_TC302718     CTAAATGTAGGAGTTATGAGCACCCTGGTGATCTTGAGAGC--ATATGCACAATA-----
wheatest_TC256052   CAACTACTTTCATATATGGTCACGACGATTGGATGAATTACCAAGGGGCGCAGCAAGCAC
potest_TC140557     ------------------------------------------------------------
ricest_TC358735     CAACTACTTTCATATATGGCCAACAAGATTGGATGAATTACCAAGGTGCACAGCAAGCAC
onest_TC176         CTACTACTTTCATATATGGCTATCATGACTGGATGAACTACCAAGGTGCACAACAAGCTC
pinest_TC42098      CAACCACCTTTATCTATGGTTATTATGACTGGATGGATTATGAAGGAGCTGTGGAGGCTC
spruest_TC31172     CAACCACCTTTATCTATGGTCATCATGACTGGATGGATTATGAAGGAGCTGTGGAGGCTC
sorgest_TC95780     CGACTACTTTCATATATGGTCAGGAAGATTGGATGAACTACCAAGGGGCTCAGCAAGCAC
sugest_TC68544      CGACTACTTTCATATATGGGCAGGAAGATTGGATGAACTACCAAGGGGCTCAGCAAGCAC
maizest_TC285906    CGACTACTTTCATATATGGGCAGCAAGATTGGATGAACTACCAAGGCGCTCAGCAAGCAC
best_TC142187       CAACTACTTTCATATATGGCCACGATGATTGGATGAATTACCAAGGGGCGCAGCAAGCAC
tobest_TC12912      CAACAGCTTTCATATATGGATACGAAGATTGGATGAATTATCAAGGAGCGGAACAGGCTA
cottest_TC38615     CAACCACTTTTATATATGGGGCTGAAGATTGGATGAACTACCAAGGAGCCCAAGAAGCTC
vvest_TC65200       CAACCACTTTTATATATGGCTTCGAAGATTGGATGAACTACCAAGGAGCCCAAGAAGCTC
ljest_TC8785        CCACTACTTTCATATATGGTGTCCAAGACTGGATGAATTATGAAGGGGCTCAAGAAGCTC
soybest_TC229646    CCACCACTTTCATGTATGGTTTCCAAGACTGGATGAATTATCAAGGTGCCCAAGAAGCTC
medicest_TC94860    CCACCACATTCATATATGGTTACGAAGATTGGATGAATTATGAAGGTGCCCAAGAAGCTC
```

FIG. 9 (Cont.)

```
atest_TC287358      GGAAATCCATGAAGG--TCCCTTGCGAAATCATTCGGGTTCCACAGGGTGGTCATTTTGT
bnest_TC15176       GGAAACACATGAAGG--TCCCTTGCGAAATCATTCGTGTTCCACAGGGTGGCCATTTTGT
popuest_TC45316     GCCAGCATATGAAGG--TTCCATGCGAGATCATTCGGGTTCCACAGGGCGGGCACTTTGT
ricest_TC302718     ------------------------------------------------------------
wheatest_TC256052   CGCAAGGACATGAAAGTTCCTTTGCGAAATCATCAGAGTCCCACAGGAAGGACATTTTGG
potest_TC140557     ------------------------------------------------------------
ricest_TC358735     GGAAAGAAATGAAAGGAGGACATTTTGTGTTCATAGATAATCCTTCGGGGTTCCACTCCG
onest_TC176         GCAAAGACATGGAAG--TACCTTGCGAAATCATAAGAGTTCCCGAGGCAGGGCATTTTGT
pinest_TC42098      GTAAACTTATGAGTG--TTCCTGCTGAGATCATAAGAGTTCCTCAAGCGGGTCACTTTGC
spruest_TC31172     GTAAACGTATGAATG--TTCCTGTTGAGATCATAAGAGTTCCTCAAGCCGGTCACTTTGC
sorgest_TC95780     GGAAGGACATGAAAG--TTCCTTGTGAAATAATCAGGGTGCCACAGAGTGGACATTTTGT
sugest_TC68544      GGAAGGACATGAAAG--TTCCTTGTGAAATAATCAGGGTGCCACAGGGTGGACATTTTGT
maizest_TC285906    GGAAGGACATGAAAG--TTCCTTGTGAAATAATCAGGGTGCCGCAGGGTGGACATTTTGT
best_TC142187       GCAAGGACATGAAAG--TTCCTTGCGAAATCATCAGAGTCCCACAGGGAGGACATTTTGT
tobest_TC12912      GGAAGAATATGAAGG--TTCCATGTGAAATCTTAAGAGTCCCTCAGGCTGGTCACTTTGT
cottest_TC38615     GCGAGCAAATGAAGG--TCCCATGTGAAATTATCAGGGTTCCTCAGGGTGGACATTTTGT
vvest_TC65200       GCAAGCAAATGAAGG--TCCCATGTGAAATTATTAGGGTCCCCCAGGCTGGGCATTTTGT
ljest_TC8785        GCAAGCATATGAAAG--TTCCCTGTGAAATCATTAGGGTTCCCCAGGCCGGGCATTTTGT
soybest_TC229646    GCAAGCATATGAAGG--TTCCATGCGAAATCATCAGGATTCCTCAGGGTGGGCACTTTGC
medicest_TC94860    GCAAGCATATGAAGG--TTCCATGTGAAATTATCAGGGTCCCTAAGGCCGGCCATTTTGT atest_TC287358      GTTCATAGACAACCCAATTGGTTTTCATTCTGCAGTGCTTTATGCTTGCCGCAAGTTTAT
bnest_TC15176       GTTCATAGACAACCCAGCTGGTTTTCATTCCGCAGTGATGTATGCTTGCC----------
popuest_TC45316     ATTCATAGACAACCCAACTGCGTTCCATTCAGCTGTGTTTTATGCTTGTCGGATGTACAT
ricest_TC302718     ------------------------------------------------------------
wheatest_TC256052   GTTTATAGATAACCCCTGGGGGGTTTCCACCCCGGGGGATCTTTCTACCGCGGGGCCGGA
potest_TC140557     ------------------------------------------------------------
ricest_TC358735     CGGTCTTCCACGCATGCCGCAAGTTTCTATCTGGAGATGGAGAGGAAGGCCTCTCTCTTC
onest_TC176         GTTCATAGATAACCCATCTGGATTCCACTCAGCTGTGTTCCACGCATGTCGTAAATTTAT
pinest_TC42098      TTTCCTAGACAATGCATCGGCATTCCATTCAGCAGTGTTGTATGCTTGTCGGAAATTTTT
spruest_TC31172     TTTCCTAGACAACGCATCGGCATTTCATTCAGCAGTGTTCTATGCTTGTCGGAAATTTTT
sorgest_TC95780     GTTTATAGACAACCCTTCAGGGTTCCACTCGGCTGTCTTCTACGCGTGCCGTAATCTTTT
sugest_TC68544      GTTTATAGACAACCCTTCAGGGTTCCACTCGGCTGTCTTCTACGCGTGCCGTAATC----
maizest_TC285906    GTTCATAGACAACCCTTCAGGGTTCCACTCGGCTGTCTTCTATGCGTGCCGTAATCTTCT
best_TC142187       GTTTATAGATAACCCTGAGGGGTTCCACTCGGCGATCTTCTACGCGTGCCGGAAATTTTT
tobest_TC12912      ATTTATAGACAACACAGCCGCATTCCACTCTGCTGTACTCTATGCTTGCCGTAGATTT--
cottest_TC38615     GTTCCTTGAAAATAGAGATGGATTCCATTCAGCTGTGTTGTATGCCTGTAGGAGATTTCT
vvest_TC65200       ATTCATAGACAATCCCTCGGGGTTCCACTCGGCTGTATTGTATGCTTGCCGCAGATTTCT
ljest_TC8785        GTTCATCGAAAACCCGTCTGGCTTCCATTCAGCTGTGTTTCATGCTTGCCGGAGGTTTCT
soybest_TC229646    GTTCATTGACAACCCAACTGCCTTCCATTCAGCTGTTTTTATGCTTGTCGAAGGTTTCT
medicest_TC94860    GTTCATTGACAACCCAAGTGGCTTCCATTCAGCTGTGTTTTATGCTTGTCGAAGGTTTCT
```

FIG. 9 (Cont.)

```
atest_TC287358      ATCTCAAGACTCCTCTCATGATCAACAACTCCTAGATGGTCT-ACGATTGGTTTA--GTC
bnest_TC15176       ------------------------------------------------------------
popuest_TC45316     TTCACCTAATC---TTGAAACTGAACATCTCCCTGAAGGTCTCACGCTTGCGTAG--GAA
ricest_TC302718     ------------------------------------------------------------
wheatest_TC256052   AATTTTTTATC----TGGGAGAGGCAGAGGGAGGGTCTCTCTCCTTCCTGATGGC--TTT
potest_TC140557     ------------------------------------------------------------
ricest_TC358735     CTGAAGGCCTA----ACATCGGCCTGA---------------------------------
onest_TC176         CAACGGTCTTG----CAGAAGACAACCTCTACCTGAAGGACTTTCATCTGCTTAA--GTA
pinest_TC42098      TAGCGAGAATG----AAGAAAATGAAATCTTCCCTGAAGGGCTAACAAGAGTGTA--GCA
spruest_TC31172     TATCAAGGATG----AAGAAAAAGAAAACTTCCCAGAAGGGATAATAAGAGTGTA--ACA
sorgest_TC95780     ATCCCAAAATGGGGAGGAGGGCTTCACATTTCCTGGTGGCCTAATATCTGCATGA-AGTG
sugest_TC68544      --------ATGGGGAGGAGGGCTTCACATTTCCTGATGGCCTAATATCTGCATGA-AGTG
maizest_TC285906    ATCAGTAAATGGAGAGGAGGGATTCACATTTCCTGATGGCCTAATATCTGCGTGA-AGTG
best_TC142187       ATCTGGAGATGCAGAGGAAGGTCTCTCTCTTCCTGATGGCTTGATATCTGCATGA-GGCG
tobest_TC12912      ATCTCACCACAGA-AGGACAATGACCCACTTCCTGAAGGCTTGATATCTGTCTGATGGAG
cottest_TC38615     TTCACCTAACCC---TGATAAAGAACCCTTTCCTGAAGGTTTGGTATCAGCATAGAAGAA
vvest_TC65200       CTTGCCTGACCC---TGATAGTCAATCCCTTCCTGAAGGCTTGACATCTGCCTAAAAATA
ljest_TC8785        GAGTCCTGATCC---TGACAATGAACCCCTTCCTGAAGGGCTAATCTCTGCATAGAGTAT
soybest_TC229646    TACACCTGATCC---AGACAATGAATCTCTTCCTAAAGGGCTAACCTCTGCATAGGTTAG
medicest_TC94860    TACCCCAAATTC---GGACAATGAATCTCTTCCCGAAGGGCTATCGTCTGCTTAGGATTT atest_TC287358      ATAGTATCTTGTTCCTTTTACCTTCCAA--------ATTTATTCTATATGTGT-AT-AC
bnest_TC15176       ------------------------------------------------------------
popuest_TC45316     ATGTTACCATAAATCTTTAATTATTTGTGTATGATTCATTTATTTTATAGCTCC-GTCAC
ricest_TC302718     ------------------------------------------------------------
wheatest_TC256052   GATATTCTGCATTGCGGGGGCCTCCCTCGGGGGACCCCCATCCCGAAATAATGG-GTATG
potest_TC140557     ------------------------------------------------------------
ricest_TC358735     ------------------------------------------------------------
onest_TC176         ATTTTGTATCACAACACATCCATGCTATACAACATTTCCATAATTGCTTTGCAT-CCAGG
pinest_TC42098      ATATT-GTGTAATACGAGCATTCAATTGTTTATAATTTAAGAAACTGGCAGGAG-AGTTT
spruest_TC31172     ATATTTGTGTAGTACAAGCATTCA-TTGCTCCTAATTTAAGAAACTGGCATGCA-AGTTT
sorgest_TC95780     GCATGTTC----AACAATCTTATCGTGCCCAACAATAGTTTATATGAAGCAAAG-ATATA
sugest_TC68544      GCATGTTC----AACAATCTTGTCCTGCCCAAGAATAGTTTATATGAAGGAAAG-ATATA
maizest_TC285906    GCATGTTC----AACAAGCTT-----GCTCAACAACAGTTTACATAAAGCAAAG-ATATA
best_TC142187       TCATCTTG----TGTGATCTCGTACCGAATAGCGGT-GTCAGCATAAAGCAAAG-CTATA
tobest_TC12912      ATACATTGCCGTGGTGTTTTCATTGCGTGTGTTGTAGGTAAATAGTGTACAATA-GCATA
cottest_TC38615     GCATAG--------------TATTTTTTTAATTTCTCTCCACATGTTGTATGGCGCATT
vvest_TC65200       GAGTAG----GCTATAAATTGTAAATTGATAGCCTATGTATAAAAAAAAAACAAAACATT
ljest_TC8785        AATTT--TCTTGTG-TAGTGCTGTCTATATT--TTTTATTTTTCATTTTTTTGACAAATA
soybest_TC229646    GTCTTAATTTTGTGCTATTCCTGTCTATATG--TATT-TTAATATTTTTTTTTACTAATT
medicest_TC94860    AATTT-----TGCATCAATCCAGTGTATATTAATATGGTTATTAATTTTTTTTT------
```

FIG. 9 (Cont.)

```
atest_TC287358      AAGTATATATGAAAAAGAACATAAAAAAGAATTACTTTCTTTATTTGAAT----------
bnest_TC15176       ------------------------------------------------------------
popuest_TC45316     AAATTTATACTAGGATGTATTAATAAAACATTCATTTTTCATGTACATGTACATCTAATG
ricest_TC302718     ------------------------------------------------------------
wheatest_TC256052   GGACTTAAAAGCAAAGGTTATCCGACCCATAGAAAAAGGCTCCATGGACGCGCGGGGCGT
potest_TC140557     ------------------------------------------------------------
ricest_TC358735     ------------------------------------------------------------
onest_TC176         CTCTATTACATAGAAATCAATTTCGAAATGCATACCCTTCACATCCAGTTAACGTTTGTA
pinest_TC42098      GCCTTTATATATTATTTTATTTGGACTTAATATATAACATGGTGGAATTCCGTCATGAAA
spruest_TC31172     GCCTTTATATATTATTTTATTTGAACTTTATGTATAATATGGTGGAATTCCATCATGAAA
sorgest_TC95780     CGATGGTGGA---AATCTTTGCTCA----TTTCCACCAATCTGGAA---ATATTTGTGCC
sugest_TC68544      CGATGGTGGA---AATCTTTGCTCA----TTTCCACCAATTTGGAA---ATATCTGTGCC
maizest_TC285906    CGATTGTGGA---AATCATTGCCCA----TTTCCACCAATTTGCTT---GTATACGGATT
best_TC142187       CAACAATAGA---AATGTTT--TTG----TATGTATGAAT-TGTGT---GAATATG----
tobest_TC12912      TTAGCATTGATTTAATATTCTCTCAAATGTGTTTACTGGTCTGAGTAACGTAACTTACCA
cottest_TC38615     ACACC---GAGTTTCATTGGCCAGAAGATTA-TTTGGGTAAAGAAAAAAACATTATTTGC
vvest_TC65200       CTTTCTGCGAAGTTTGTTGGTTCATACATTC-TTCTGTAGTTGATGACTTCATAAGAAAA
ljest_TC8785        AAATTCCATAATTTAATCAAGCCATATTCTAGTCTTGTAAGTTGTAAGAGCAATTCAAAG
soybest_TC229646    AAATTTCATAATTGAATGAAATCATATGTATATTGTTTCAGTA--AAGTGGAATTTACTG
medicest_TC94860    --ACTTCATAACTGAATGAAGCCGTGTCTTG--TTTCTCAGTG--AAGTGGAATATAATG atest_TC287358      ------------------------------------------------------------
bnest_TC15176       ------------------------------------------------------------
popuest_TC45316     TACTTGAGTTGTGCTGGATGCAGCTGTATTTATTGAATATGAGCTCCGGAAGTTGAAACT
ricest_TC302718     ------------------------------------------------------------
wheatest_TC256052   CCCCCAACTCGGTTATTTAGAATGGATGGAATCTCCTGCGAAAATAAGTCTTTTCTCTA
potest_TC140557     ------------------------------------------------------------
ricest_TC358735     ------------------------------------------------------------
onest_TC176         CAATTAAACATAGGTCTTGGTATCTTACATTTGCACGCGTTT------------------
pinest_TC42098      ATGTTGACTGAAAATGATTGCAAAGCTTACTGTATAATCTTGTAT--ATGTTATTCTTTT
spruest_TC31172     ATGTTGACTGATAATGGTTGTGAAGCTTTGTGCATAATCTTGTATTTACGTTATTCTTTT
sorgest_TC95780     CTCTTCCACCAATTTGTTTGTATACGGATTATGCC-GTGTATATATTCTGTGTTGACTGT
sugest_TC68544      CTCGTCCACCAATTTGTTTGTATACGGATCATGCC-GTGTGTATATTCTGTGATGACTGT
maizest_TC285906    ATGCTGTGTATAT---ATTACATAACAAATGTATT-A-GTAT-CATTTAATGCACGATTT
best_TC142187       -TCATTCATATGT--GCTTGCGTACCAACAACACTAGTGAGACAATTATGTTTTTTTTTT
tobest_TC12912      GTTTCTCAGAACATAATATCAATGTTAAGGAAGTC-ATGAATGGGTAGCATTCTGTTCTT
cottest_TC38615     CTGTAGCTTGTATCATAATATTTTTATATACGTATTATGTGTTTTGTAGTACCTTGAATC
vvest_TC65200       TTCCATTGTTCCTCAGAGAAGCTATATTCTGAACGCATGCATAATTTAATTCAGTTGTTA
ljest_TC8785        AAAAACCAACTGTAATATAAATTTGATGTGTGTAACATGTGCTAATTAAAACATGTAAT-
soybest_TC229646    AAAA--TATTTGTAATAGCAACTTCAACAAAAATCGATTTGTAGGAGAAATTTCTTCCC-
medicest_TC94860    GAAA--TATATGTAATTGTAATAACAATAATATT-GATTTGTTGGGGAACTTTGAGGAC-
```

FIG. 9 (Cont.)

```
atest_TC287358      ------------------------------------------------------------
bnest_TC15176       ------------------------------------------------------------
popuest_TC45316     TTCAAAAATGGTCATCAAACAGTTCGTGGTTTCCTCGACCCGTGGAGAAAGTTTCTACAT
ricest_TC302718     ------------------------------------------------------------
wheatest_TC256052   TTGGTAGTTCTCCGTCACCCCTCAACACTCTAAACTGAAGAACAAACTTAAGCTGCCTTG
potest_TC140557     ------------------------------------------------------------
ricest_TC358735     ------------------------------------------------------------
onest_TC176         ------------------------------------------------------------
pinest_TC42098      NNT---------------------------------------------------------
spruest_TC31172     GATAGTTGAAAATGTTGAATCTAGTTCACTTTAGGTGCC---------------------
sorgest_TC95780     AAGAAACATAATGTATTAACATTATGTAATGTATGTACGATTC--TT-TATTTGATTTTC
sugest_TC68544      AAGAAACATAATGTATTAACATTATGTAATGTATGTACGATTC--TT-TATATGATTTTC
maizest_TC285906    GTGAAAGGGCCTGAGTTTGTATTTAGCGAATTTTAGGTTGGTT--TT-TTTCCCTTTTTC
best_TC142187       GCAGGTCTAGACATA-----ATTATGTCATATATGTAAGATCT--TCCTAGTCAGTTTTT
tobest_TC12912      CTGATTGTTCGTTCCTT-GTAGGAAGTCATGCACAGATAGGTCGATGATTTGTGTTCTTG
cottest_TC38615     TGGTTACTGGTTTAAGGGAATGGATATTGAAGAATTGATTTT------------------
vvest_TC65200       TGAGCGGTTGAATTTGCCACCGGATCTTCAACAAATTTCTTAAATGCTATTTATGAGTAA
ljest_TC8785        TGGTTTTTGTATTATTTTG--TGCTATGGATGAAAATTTAGTCTTACTA-ATTTAACCTC
soybest_TC229646    TGGAAATTGTTCTATTTTAAATCTTGTTGCTCATAAGATATTATGACTTCATTCAATGTC
medicest_TC94860    AAAAACATATTCTGGTAAAA-TTTTGTTGCACATGCGACAAACATATGCTGTG------- atest_TC287358      ------------------------------------------------------------
bnest_TC15176       ------------------------------------------------------------
popuest_TC45316     TAATCATACTGAAAATAGGAAAATGTTTGTTTATGAAAGGGATGCACTATAGGGTGCATT
ricest_TC302718     ------------------------------------------------------------
wheatest_TC256052   TCGTATGCCGGGCGCCTCCGAATATTAAACTAAAGGCTCATATACGCGCACAACAAACAC
potest_TC140557     ------------------------------------------------------------
ricest_TC358735     ------------------------------------------------------------
onest_TC176         ------------------------------------------------------------
pinest_TC42098      ------------------------------------------------------------
spruest_TC31172     ------------------------------------------------------------
sorgest_TC95780     AACTTGCAATACGCAAG--AACCAC-----------------------------------
sugest_TC68544      GAATTGCAATACGCGAG--AACCATTTTCTTT----------------------------
maizest_TC285906    TTCTTTCAGTGCGCTTGCTAGTCAATCCCATACTATAAGCCGTGATCATTTTTTGTTTAT
best_TC142187       AGGTCAAGTTGCTGTAAGTGATGCTCTATATTCTTTAAGGGCAACTTTATGTTTGCCTGC
tobest_TC12912      AAATTACATTAATTTTTTTTTATGAATAGTGTACTCAAAAGTTACGAAAGCAATAAGATGA
cottest_TC38615     ------------------------------------------------------------
vvest_TC65200       ATCTGAATTTGAGGGTACCTTGTACATGCATTGTGACTGAAGTAAAATTCGGGTTGCCCT
ljest_TC8785        TACCAT------------------------------------------------------
soybest_TC229646    TTTTAGGAAAAGTAGTTAGTTATATTAAATTTGTC-------------------------
medicest_TC94860    ------------------------------------------------------------
```

FIG. 9 (Cont.)

```
atest_TC287358      ----------------------------------------------------------------
bnest_TC15176       ----------------------------------------------------------------
popuest_TC45316     TTGGCAATTTCATAGTGTGATAATTAATTACGTGCGGATAAAGGGCTTGGTTGATATCAT
ricest_TC302718     ----------------------------------------------------------------
wheatest_TC256052   CCCC------------------------------------------------------------
potest_TC140557     ----------------------------------------------------------------
ricest_TC358735     ----------------------------------------------------------------
onest_TC176         ----------------------------------------------------------------
pinest_TC42098      ----------------------------------------------------------------
spruest_TC31172     ----------------------------------------------------------------
sorgest_TC95780     ----------------------------------------------------------------
sugest_TC68544      ----------------------------------------------------------------
maizest_TC285906    GTCTCATAATATAAGGCACATCTCACTACACACGTTTATCGATGCAGTGATATATAGGGA
best_TC142187       TACGAAACATCTTCACAGTATTAACTGCCGCTGTACATTTGCTGCAGTCATTGCTGCGTC
tobest_TC12912      TGTACAAAT-------------------------------------------------------
cottest_TC38615     ----------------------------------------------------------------
vvest_TC65200       TCCTTGTACCTCTGCATGAGAGCTATGAAGAGATTTTATAATTTTGGTTTATGCCCTTCA
ljest_TC8785        ----------------------------------------------------------------
soybest_TC229646    ----------------------------------------------------------------
medicest_TC94860    ---------------------------------------------------------------- atest_TC287358      ----------------------------------------------------------------
bnest_TC15176       ----------------------------------------------------------------
popuest_TC45316     ATTTTATAAAATCTTATTTGAGATTTGTTTTC--------------------------------
ricest_TC302718     ----------------------------------------------------------------
wheatest_TC256052   ----------------------------------------------------------------
potest_TC140557     ----------------------------------------------------------------
ricest_TC358735     ----------------------------------------------------------------
onest_TC176         ----------------------------------------------------------------
pinest_TC42098      ----------------------------------------------------------------
spruest_TC31172     ----------------------------------------------------------------
sorgest_TC95780     ----------------------------------------------------------------
sugest_TC68544      ----------------------------------------------------------------
maizest_TC285906    ATTAAATACAATTTTTGGTTTT------------------------------------------
best_TC142187       GTAGCCATTTTTAGAAAGTATTTTGGAACAGTGGAAGTGCATTTTGGTGTCTTACGATGC
tobest_TC12912      ----------------------------------------------------------------
cottest_TC38615     ----------------------------------------------------------------
vvest_TC65200       TTGTAGAAAAGTTCACTGTTGGTATAATTAATGCCGCCCTCACTTGCAGCTCTGCATAGT
ljest_TC8785        ----------------------------------------------------------------
soybest_TC229646    ----------------------------------------------------------------
medicest_TC94860    ----------------------------------------------------------------
```

FIG. 9 (Cont.)

```
atest_TC287358      ------------------------------
bnest_TC15176       ------------------------------
popuest_TC45316     ------------------------------
ricest_TC302718     ------------------------------
wheatest_TC256052   ------------------------------
potest_TC140557     ------------------------------
ricest_TC358735     ------------------------------
onest_TC176         ------------------------------
pinest_TC42098      ------------------------------
spruest_TC31172     ------------------------------
sorgest_TC95780     ------------------------------
sugest_TC68544      ------------------------------
maizest_TC285906    ------------------------------
best_TC142187       TATTATCCTACCAGACTATTTTGATAAAAAAAG
tobest_TC12912      ------------------------------
cottest_TC38615     ------------------------------
vvest_TC65200       CATGAGGGAGGAGGTATTT-------------
ljest_TC8785        ------------------------------
soybest_TC229646    ------------------------------
medicest_TC94860    ------------------------------
```

ENGINEERING LIPIDS IN VEGETATIVE TISSUES OF PLANTS

This application is a continuation of U.S. application Ser. No. 12/696,037, filed Jan. 28, 2010, which claims the benefit of priority of U.S. Provisional Appl. Ser. No. 61/148,952, filed Jan. 31, 2009, each of the entire disclosures of which are incorporated herein by reference.

GOVERNMENT INTEREST

This invention was made with government support under Grant HL 20948 and Grant GM 52016 awarded by the National Institute of Health. The government has certain rights in the invention.

BACKGROUND OF THE INVENTION

1. Field of the Invention

The invention relates to the engineering of plants to alter lipid content in vegetative portions of the plant.

2. Description of Related Art

Plants synthesize and store oil primarily in cytosolic lipid droplets, and much of the Earth's fossil fuel reserves are the consequence of this process. In domesticated oilseeds, these stored triacylglycerols (TAGs) represent a major source of calories for human and animal nutrition, an excellent feedstock for diesel fuels, and a reservoir for the deposition of industrial fatty acids for chemical feedstocks. A number of acyltransferases are involved in the biosynthesis of TAGs, including acyl-CoA:cholesterol acyltransferases (ACATs), diacylglycerol acyltransferases DGAT1s and DGAT2s), lecithin:cholesterol acyltransferases (LCATs), phospholipid: diacylglycerol acyltransferases (PDATs), glycerol-3-phosphate acyltransferases (GPATs) and acyl-CoA lysophosphatidic acid acyltransferases (LPAATs). In plants, TAG is the primary component of vegetable oil that is used by the seed as a stored form of energy to be used during seed germination.

Higher plants are believed to synthesize oils via a metabolic pathway commonly referred to as the Kennedy pathway (Kennedy et al., 1956; Finnlayson et al., 1980). Fatty acids are made in plastids from acetyl-CoA through a series of reactions catalyzed by enzymes known collectively as Fatty Acid Synthase (FAS). The fatty acids produced in plastids are exported to the cytosolic compartment of the cell, and are esterified to coenzyme A. These acyl-CoAs are the substrates for glycerolipid synthesis on the endoplasmic reticulum (ER). Glycerolipid synthesis itself is a series of reactions leading first to phosphatidic acid (PA) and 1,2-diacylglycerol (DAG). Either of these metabolic intermediates may be directed to membrane phospholipids such as phosphatidylglycerol (PG), phosphatidylethanolamine (PE), or phosphatidylcholine (PC), or they may be directed on to form neutral triacylglycerol (TAG). DAG is synthesized from glycerol-3-phosphate and fatty acyl-CoAs in two steps catalyzed sequentially by glycerol-3-phosphate acyltransferase (G3PAT), and lysophosphatidic acid acyltransferase (LPAAT) to make PA, and then an additional hydrolytic step catalyzed by phosphatidic acid phosphatase (PAP) to make DAG. In most cells, DAG is used to make membrane phospholipids, the first step being the synthesis of PC catalyzed by CTP-phosphocholine cytidylyltransferase. In cells producing storage oils, DAG is acylated with a third fatty acid in a reaction catalyzed by DAGAT.

Factors governing the oil content of a vegetative plant part are not well known, and the role of a CGI58 homolog in lipid accumulation in vegetative tissues of plants has not been previously described. As such, materials and methods for increasing the neutral lipid (e.g. oil content, including TAG) content in cells of plant vegetative tissues by use of CGI58-related sequences have not been previously described.

BRIEF DESCRIPTION OF THE FIGURES

Figure 1:
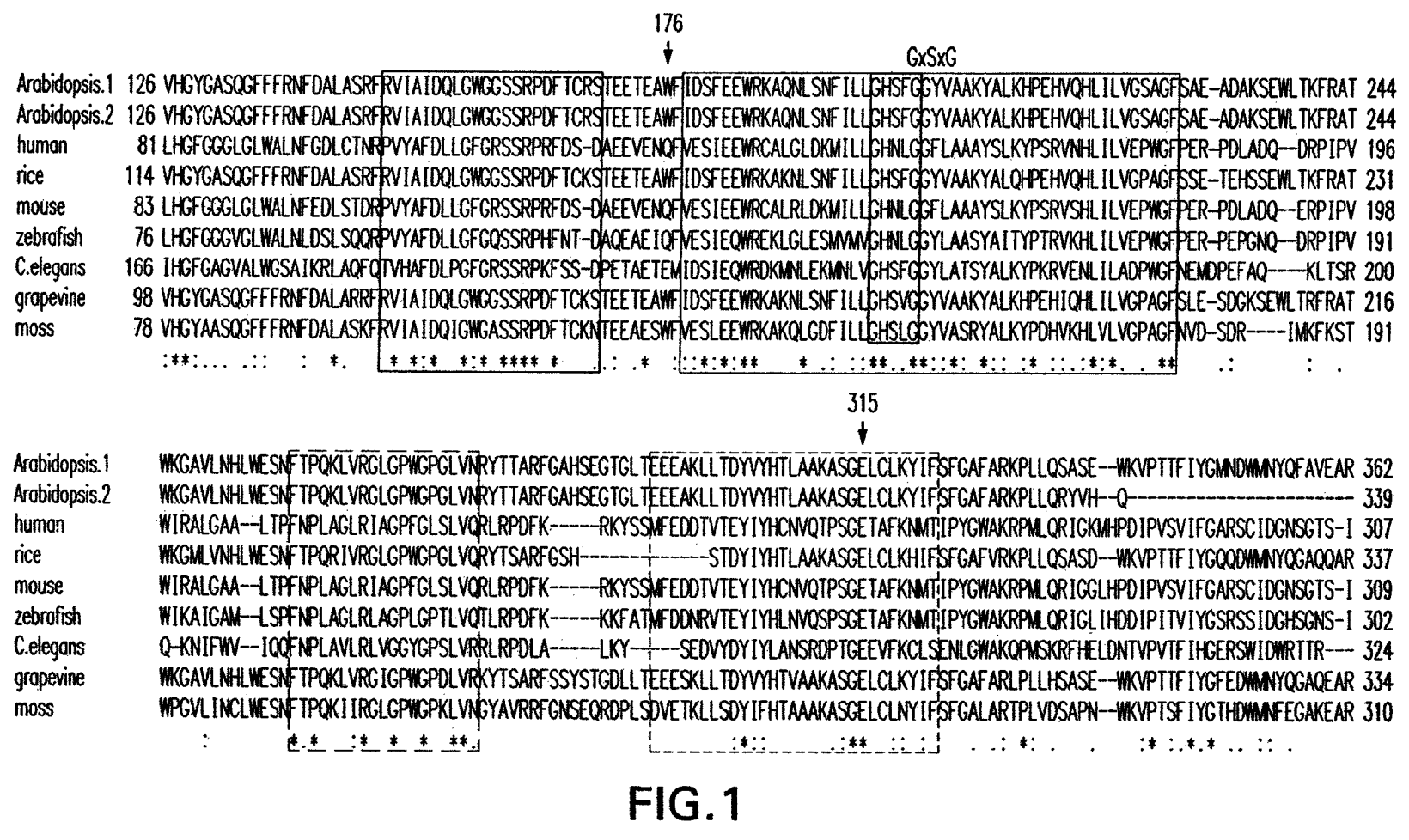
Figure 1:
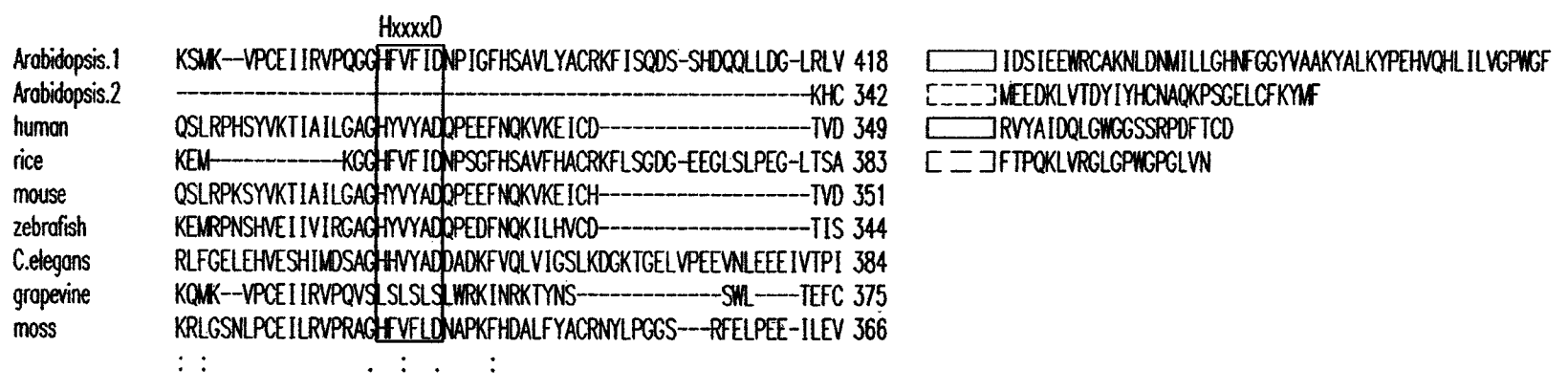

FIG. 1: shows partial amino acid sequence alignments of Arabidopsis At4g24160 (CGI58-homolog) splice variants (Arabidopsis 1, 2), and homologs from grape, rice, human, mouse, *C. elegans*, zebrafish, and moss (*Physcomitrella*) (SEQ ID NOs: 9-18). Motif analysis by MEME/MAST or visual analysis reveals four distinct domains common to all proteins (shaded boxes). A classical GXSXG (SEQ ID NO:1) esterase/lipase sequence (boxed and annotated above the sequence) is present in the plant and nematode sequences, and the acyltransferase motif $(H(X)_4D)$ (SEQ ID NO:17; also boxed and annotated) is present in all but the truncated Arabidopsis splice variant. Consensus sequences of each motif are shown at the bottom right (SEQ ID NOs: 2-5). Conserved residues are noted with an asterisk, strongly similar amino acids with a colon, and weakly similar amino acids with a period. Two positions in the *Arabidopsis* amino acid sequence marked 176 and 315 correspond to residues, that when mutated in the human sequence, interfere with lipid body binding and cause disease. "*Arabidopsis.1*" represents aligned portions of SEQ ID NO:7; "*Arabidopsis.2*" (SEQ ID NO:9) represents aligned portions of the shorter polypeptide (SEQ ID NO:38) produced by the At4g24160 splice variant, also indicating the differences with the longer polypeptide encoded at the same locus.

FIG. 9: shows a Clustal alignment of the sequence of *Arabidopsis* TIGR cDNA clone TC287358 (SEQ ID NO:8), containing the At4g24160 gene (CGI58 homolog), with cDNA sequences of other organisms: *B. napus*, poplar, rice, wheat, potato, onion, pine, spruce, sorghum, sugarcane, maize, barley, tobacco, cotton, grape, *Lotus japonicus*, soybean, and alfalfa (SEQ ID NOs:18-36). The gene is located on *Arabidopsis* chromosome 4, spanning bases 12,539,796-12,542,321, according to the *Arabidopsis* genome TC alignment (version 5), available at the Gene Index Project (compbio.dfci.harvard.edu/tgi; Quackenbush et al., 2001).

SUMMARY OF THE INVENTION

Figure 2A:
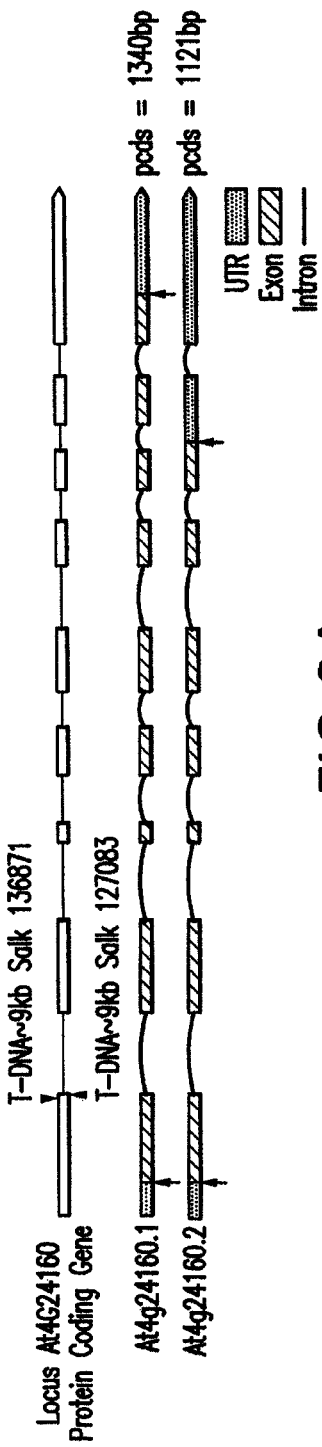
FIG. 2: (A) the relative gene exon/intron structure of the At4g24160 locus, which gives rise to two transcripts; and (B) Detection of both transcripts by RT-PCR in wild-type seedlings; neither is detected in seedlings of T-DNA insert mutant lines. Nucleotide sequence of full length transcript (mRNA) is given in SEQ ID NO:6. The corresponding amino acid sequence is given in SEQ ID NO:7. The nucleotide sequence of the second transcript is given in SEQ ID NO:37, and the corresponding amino acid sequence is given in SEQ ID NO:38. Ubiquitin transcripts expressed in seedlings of the same wild-type and mutant lines are shown as a control. cDNAs corresponding to the protein coding sequences of both transcripts were amplified from seedling mRNA.
Figure 2B:
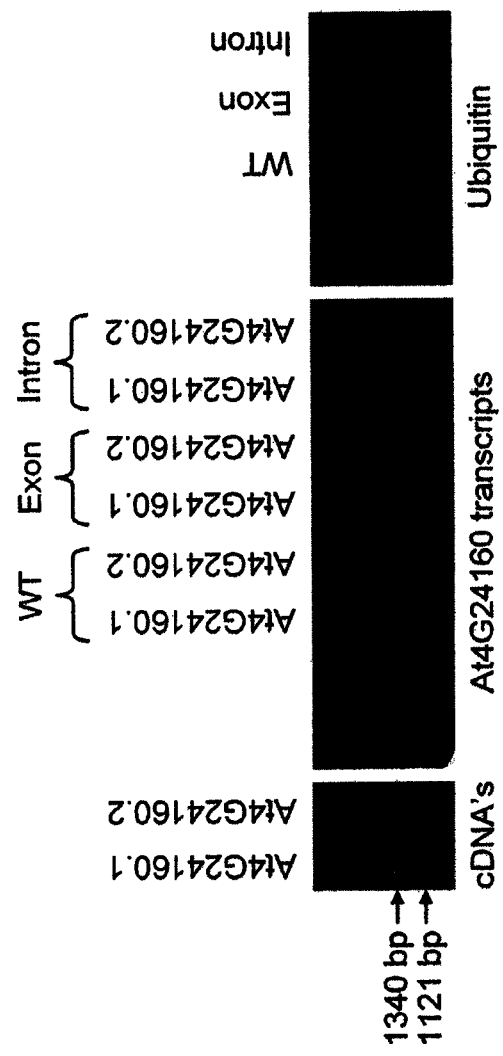

In one aspect, the present invention provides a plant comprising increased lipid accumulation in vegetative tissues relative to a wild type plant of the same species and wherein activity of an At4g24160 gene product or a homolog thereof has been down-regulated in the plant. In one embodiment, down-regulation of an At4g24160 gene product or a homolog thereof comprises at least one method selected from the group consisting of: a) expressing in the plant a RNA molecule complementary to all or a portion of an mRNA expressed from a gene comprising a sequence selected from the group consisting of SEQ ID NOs:18-36, wherein the RNA molecule inhibits the function of the At4g24160 gene product or homolog thereof in said plant; b) mutagenizing said At4g24160 gene, or homolog thereof, so that the function thereof is down-regulated relative to wild type At4g24160 or a homolog thereof, in a plant of the same species; and c) co-suppression.

In certain embodiments, the plant is a transgenic plant; in other embodiments, the plant is non-transgenic. The plant may further be defined as a fertile $R_0$ transgenic plant, or as a progeny plant of any generation of a fertile $R_0$ transgenic plant. A part of such a plant is an embodiment of the invention. In certain embodiments, the plant part is selected from the group consisting of a cell (including a cell (e.g. tissue) culture), a leaf, a stem, a petiole, pollen, a tuber, and root tissue.

Another aspect of the invention relates to a seed of a plant comprising increased lipid accumulation in vegetative tissues relative to a wild type plant of the same species and wherein activity of an At4g24160 gene product or a homolog thereof has been down-regulated in the plant, further wherein the seed is of a plant that comprises increased lipid accumulation in vegetative tissues, relative to a wild type plant of the same species.

Another aspect of the invention relates to a method of altering lipid content in a plant (including a plant cell or plant cell culture) comprising down-regulating the function of an At4g24160 gene product or homolog thereof. In certain embodiments, the sequence of the gene encoding the homolog, or of the homolog, comprises a sequence selected from the group consisting of: SEQ ID NOs:18-36; a sequence at least about 70% identical to a any of SEQ ID NOs:6 or 18-36; and a sequence at least about 75% identical to any of SEQ ID NOs:10-16.

In some embodiments, down-regulating the function of an At4g24160 gene product or homolog thereof comprises eliminating the function of said an At4g24160 gene product or homolog thereof. In certain embodiments, down-regulating the function of an At4g24160 gene product or homolog thereof comprises expressing in the plant a RNA molecule complementary to all or a portion of an mRNA expressed from a gene comprising a sequence selected from the group consisting of SEQ ID NOs:18-36, wherein the RNA molecule inhibits the function or expression of an At4g24160 gene product or homolog thereof in said plant. In particular embodiments the RNA molecule is a single stranded RNA molecule. In yet other embodiments, the RNA molecule is a double stranded RNA molecule. In still yet other embodiments, down-regulating the function of an At4g24160 gene product or homolog thereof comprises mutagenizing said At4g24160 gene, or homolog thereof, so that the function thereof is down-regulated relative to the wild type At4g24160 or homolog thereof in a plant of the same species. In further embodiments, down-regulating the function of an At4g24160 gene product or homolog thereof comprises co-suppression.

In certain embodiments, the plant is of a species selected from the group consisting of corn, sugarcane, sorghum, millet, rice, wheat, barley, soybean, *Glycine* sp., grape, canola, *Arabidopsis, Brassica* sp., cotton, tobacco, sugar beet, sunflower, bamboo, switchgrass (*Panicum virgatum*), giant reed (*Arundo donax*), reed canarygrass (*Phalaris arundinacea*), Miscanthus×giganteus, *Miscanthus* sp., *Sericea lespedeza* (*Lespedeza cuneata*), ryegrass (*Lolium multylorum, Lolium* sp.), timothy, kochia (*Kochia scoparia*), forage soybeans, alfalfa, clover, turf grass, sunn hemp, kenaf, bahiagrass, bermudagrass, dallisgrass, pangolagrass, big bluestem, indiangrass, fescue (*Festuca* sp.) including tall fescue, *Dactylis* sp., *Brachypodium distachyon*, smooth bromegrass, orchardgrass, kentucky bluegrass, yellow nutsedge (*Cyperus esculentus*), pine, poplar (*Populus* sp.), willow, and eucalyptus.

Another aspect of the invention comprises a method of producing lipids in a plant comprising: (a) obtaining a plant comprising increased lipid accumulation in vegetative tissues relative to a wild type plant of the same species and wherein activity of an At4g24160 gene product or a homolog thereof has been down-regulated in the plant; and (b) isolating lipid from said plant. In certain embodiments, the fatty acid content of lipids accumulated in vegetative tissue comprise a rationally defined fatty acid profile. In other embodiments, the neutral lipids accumulated in vegetative tissue are leaf-specific fatty acids. In particular embodiments the fatty acids are rich in omega-3 fatty acids.

Yet another aspect of the invention relates to a method of plant breeding comprising: identifying a plant comprising a reduced level of function of an At4g24160 gene product or a homolog thereof relative to that found in an otherwise isogenic plant that displays a wild-type level of function of an At4g24160 gene product or homolog thereof; and selecting the plant for crossing with a second plant. In certain embodiments, the method may further be defined as comprising a step wherein identifying comprises at least one method selected from the group consisting of: PCR, single strand conformational polymorphism analysis, denaturing gradient gel electrophoresis, cleavage fragment length polymorphism analysis and/or DNA sequencing. In certain embodiments the method comprises: a) identifying at least a first polymorphism at the At4g24160 locus, or a locus encoding a homolog thereof, in a crop plant that confers increased neutral lipid content in vegetative tissues of the plant; b) assaying a crop plant for the presence of the polymorphism; and c) selecting at least a first crop plant comprising the polymorphism. The method further comprises, in certain embodiments, crossing the first crop plant with a second crop plant of the same species or variety to produce a progeny plant comprising the polymorphism. In some embodiments the polymorphism comprises an insertion, a deletion, or at least one single nucleotide polymorphism (SNP) at a position in the At4g24160 locus, or a locus encoding a homolog thereof, that reduces the function of At4g24160, or corresponding homolog thereof, relative to that found in an otherwise isogenic plant displaying a wild-type level of function of an At4g24160 gene product, or homolog thereof.

Another aspect of the invention relates to a method of producing food, feed, or oil comprising: (a) obtaining a plant or progeny thereof, according to the method of plant breeding comprising: identifying a plant comprising a reduced level of function of an At4g24160 gene product or a homolog thereof relative to that found in an otherwise isogenic plant that displays a wild-type level of function of an At4g24160 gene product or homolog thereof; and selecting the plant for crossing with a second plant; (b) cultivating said plant to produce a plant product; and (c) preparing food, feed, or oil from said plant or plant product. In certain embodiments, the oil comprises TAG. In other embodiments, the plant product comprises leaves, stems, shoots, tubers, or roots.

In certain embodiments, the neutral lipids isolated from vegetative tissues of a plant comprise a rationally designed fatty acid profile. In particular embodiments, the neutral lipids may comprise hydroxyl, epoxy, cyclic, acetylenic, saturated, polyunsaturated, short-chain fatty acids, long-chain fatty acids, TAGs, wax-esters, or steryl-esters. In other embodiments, the neutral lipids isolated from vegetative tissues of the plant comprise a leaf-specific fatty acid profile. Thus, in particular embodiments, the neutral lipids isolated from vegetative tissues of the plant may comprise hexadecatrienoic and octadecatetraenoic fatty acids, or do not contain eicosaenoic fatty acid.

DETAILED DESCRIPTION OF THE INVENTION

The following is a detailed description of the invention provided to aid those skilled in the art in practicing the present invention. Those of ordinary skill in the art may make modifications and variations in the embodiments described herein without departing from the spirit or scope of the present invention.

The present invention relates to altering the lipid composition of a plant, and vegetative production of lipids in particular, by affecting the expression of certain plant genes, such as a At4g24160 gene of *Arabidopsis* or plant homologs thereof. This specifically includes, but is not limited to, plants such as corn, sugarcane, sorghum, millet, rice, wheat, barley, soybean, *Glycine* sp., grape, canola, *Arabidopsis*, *Brassica* sp., cotton, tobacco, bamboo, sugar beet, sunflower, willow, switchgrass (*Panicum virgatum*), giant reed (*Arundo donax*), reed canarygrass (*Phalaris arundinacea*), *Miscanthus×giganteus, Miscanthus* sp., *Sericea lespedeza* (*Lespedeza cuneata*), ryegrass (*Lolium multiflorum, lolium* sp.), timothy, kochia (*Kochia scoparia*), forage soybeans, alfalfa, clover, turf grass, sunn hemp, kenaf, bahiagrass, bermudagrass, dallisgrass, pangolagrass, big bluestem, indiangrass, fescue (*Festuca* sp.) including tall fescue, *Dactylis* sp., *Brachypodium distachyon*, smooth bromegrass, orchardgrass, kentucky bluegrass, yellow nutsedge, pine, poplar (*Populus* sp.), and eucalyptus, among others. The present invention thus provides methods for controlling levels of lipids in plants.

Chanarin-Dorfman Syndrome is a neutral-lipid storage disorder (Lefevre et al., 2001; Bruno et al., 2008). CGI58, also known as ABHD5, associates with lipid droplets in human cells and participates in storage lipid hydrolysis. A mutation in this protein results in hyperaccumulation of lipid droplets in cells and the pathology associated with this syndrome. The CGI58 protein sequence includes a so-called "alpha/beta hydrolase fold" that is shared by members of the esterase/lipase/thioesterase family, suggesting that it might be a TAG lipase. Recent analyses of its functional properties have indicated that the mammalian polypeptide stimulates the activity of a lipase called ATGL (Adipose Triglyceride Lipase), which is the major lipase responsible for catalyzing the initial step of TAG breakdown in both adipose and non-lipid storing cell types (e.g. Lass et al., 2006; Yen & Farese, 2006; Schweiger et al., 2006; Yamaguchi et al., 2007). Interestingly, CGI58 also possesses lysophosphatidic acid acyltransferase (LPAAT) activity in vitro, suggesting that, in addition to its role in stimulating lipase activity, it may play a role in recycling of fatty acids into membrane phospholipids (Ghosh et al., 2008).

At4g24160 has been identified by the inventors as a putative homolog of human CGI58, in *Arabidopsis thaliana*. The gene in *Arabidopsis* is apparently expressed as two alternative transcripts (two distinct cDNAs corresponding to the same gene have been identified) and the predicted protein products share domain architecture with other lipases/esterases and acyltransferases (FIG. 1). Surprisingly, *Arabidopsis* mutant lines lacking the function of the CGI58 homolog (i.e. At4g24160) contained vegetative (i.e. non-seed) tissues with metabolic machinery capable of synthesizing and storing oil as TAG, demonstrating that there are mechanisms in place to regulate this process in non-seed tissues. It is thus provided for the first time that this mechanism can be exploited for the synthesis and accumulation in substantial quantities of desired neutral lipid compounds (i.e. oils) in above-ground biomass of plants, as well as in plant cell cultures.

Triacylglycerols can be synthesized in non-seed tissues (Murphy, 2001); however, their abundance is low and these storage lipids are presumed to be metabolized rapidly, perhaps for the recycling of fatty acids for energy or the synthesis of membrane lipids. Thus the regulation and transient accumulation of storage oils in non-seed tissues is not well understood.

In certain embodiments, "controlling levels of lipids" as used herein refers to control of lipid levels in vegetative portions of the plants. Likewise, "controlling fatty acid composition" refers to altering the molecular composition of fatty acids in neutral lipids produced in vegetative tissues of plants with decreased level of At4g24160 function, to obtain lipids displaying a particular profile of fatty acids, such as a leaf-specific fatty acid profile. Thus, the fatty acids may include hydroxyl, epoxy, cyclic, acetylenic, saturated, polyunsaturated, short-chain or long-chain fatty acids that are incorporated into neutral lipids that can be compartmentalized in lipid droplets, including TAGs, wax-esters, and steryl-esters.

"Down-regulating" as used herein refers to reducing the expression or function of the At4g24160 gene or homolog thereof. Such reduction may be a 25%, 50%, 75%, or up to 90%, or more, reduction in gene expression, or in function of a At4g24160 polypeptide or homolog thereof. For instance, this may be measured by comparing the level of mRNA transcript(s) derived from the At4g24160 locus, or homolog thereof, in a given plant cell with the level of such transcript(s) found in an otherwise isogenic plant cell, but differing in function or regulation of the At4g24160 locus, or homolog thereof, including functional activity of a polypeptide encoded at this locus, under comparable conditions. Such "down-regulated" function may also be measured by assaying the enzymatic activity of a polypeptide, such as ATGL (Adipose Triglyceride Lipase) or homolog, that is regulated by a polypeptide encoded at the At4g24160 locus or a locus homologous thereto.

"Homolog," as used herein, refers to genes related to each other by descent from a common ancestral DNA sequence, and such genes, as understood herein, may share about 70%, 75%, 80%, 85%, 90%, 95%, 98%, 99%, or greater sequence similarity at the nucleotide level with any of the nucleotide sequences given in SEQ ID NOs:6, 8, and 18-37. In some embodiments, homologs comprise the domain structure shown in FIG. 1, for instance one or more, two or more, or three or more of the four domains indicated by shading in FIG. 1, and/or one or more of the esterase/lipase and acyltransferase sequence motifs described in FIG. 1. Homologs may also be defined, in certain embodiments, as polypeptides comprising at least about 75%, 80%, 85%, 90%, 95%, 98%, 99%, or more, sequence similarity, at the corresponding amino acid sequences, with one or more of the polypeptide sequences given in SEQ ID NOs:7, 10-16, and 38.

By "vegetative portions" is meant non-seed portions, including leaves, stems, shoots, buds, tubers, and roots, among others. Thus, in specific embodiments, levels of neutral lipids such as triacylglycerols (TAGs), diacylglycerols (DAGs, e.g. 1,2-diacylglycerol, or 1,3-diacylglycerol), and monoacylglycerols in vegetative portions of a plant are increased relative to the levels typically seen in such portions of a given plant (e.g. in a similar and otherwise isogenic but non cgi58-mutant plant). This increase may result in a vegetative tissue neutral lipid content of, for example, about 0.5%, 1%, 2%, 3%, 4%, 5%, 6%, 8%, 10%, 15%, 20%, 25%, 30%, 40%, 50%, or greater, on a w/w basis. Thus, the amount of TAG in vegetative tissues of mature cgi58 mutant plants, such as cgi58 mutant *Arabidopsis*, may be measured by electrospray MS against a tripentadecanoyl standard (or by another method known in the art) and be about 50% higher than in otherwise similar wild-type plants. The level of neutral lipids in vegetative portions of a plant may be measured at various stages of vegetative tissue growth, for instance when true leaves are expanding, when they are fully expanded but not senescing, or when they are beginning to senesce (e.g., corresponding to developmental stages of about 15, 40, and 65 days after emergence as seen for *Arabidopsis* plants). In some embodiments, TAG content in a vegetative portion of a plant that displays decreased function of At4g24160 or a homolog thereof, may increase 2-fold, or 3-fold, 5-fold, 10-fold, or more, relative to that found in an otherwise isogenic plant of the same variety or species that differs by displaying a wild-type level of At4g24160 homolog function, such as the activity of a polypeptide encoded at the At4g24160 locus, or a locus homologous thereto.

Additionally, the fatty acid profile of neutral lipids synthesized in vegetative portions of a plant that displays decreased function of At4g24160 or a homolog thereof may show a molecular composition similar to that found in wild-type leaves, for instance demonstrating an increase in omega-3 fatty acid content, or an increase in the ratio of omega-3 to omega-6 fatty acids, relative to this level or ratio of neutral lipids as typically found in seed tissues. Thus, such TAGs, DAGs, and/or monoacylglycerols being produced in vegetative portions of a plant that displays decreased function of At4g24160 or a homolog thereof may, for instance, comprise levels of 16:3 and 18:3 hexadecatrienoic and octadecatrienoic fatty acids, as is typically found in leaf tissue, while, for instance, not containing the level of 20:1 eicosaenoic fatty acids typically found in seed oil bodies such as those of *Arabidopsis*. Thus, the fatty acid composition (as well as the level of neutral lipids) may be manipulated in vegetative tissues of plants with altered (e.g. decreased) level of At4g24160 function, to yield particular useful lipid species, including ones that are not found, or found at such levels, in seed oil. This further allows for the production of plants and tissue cultures which display rationally designed fatty acid profiles in the neutral lipids produced in their vegetative tissues, such as neutral lipids from vegetative tissues which are enriched in omega-3 fatty acid content, relative to the omega-3 fatty acid content found in neutral lipids of seed oils. For instance, one or more enzymes specific for production of a particular fatty acid of interest, or which are known to alter the fatty acid profile of lipids in an organism, as is known in the art, may be introduced into a cgi58 mutant plant, or other plant displaying decreased At4g24160 function, in order to produce a plant, or plant-derived oil, comprising neutral lipids (e.g. vegetatively-produced neutral lipids) displaying a specific non naturally occurring fatty acid profile, or which contain one or more specific fatty acid(s) of interest. This may, for instance, include any fatty acid for industrial purposes (e.g. for production of food, feed, or fuel), for which an enzymatic step or steps can be introduced or modified in plants, including hydroxyl, epoxy, cyclic, acetylenic, saturated, polyunsaturated, short-chain or long-chain fatty acids that are incorporated into neutral lipids that can be compartmentalized in lipid droplets, including TAGs, wax-esters, and steryl-esters.

The substantial elevation of what is almost entirely TAG in cgi58 homolog T-DNA knockouts (e.g. see FIG. 3 upper right) indicates that multiple molecular strategies can be used for oil engineering in vegetative tissues in accordance with the invention. Because this biomass would not necessarily compete with food crops directly, this strategy could allow better utilization of GM and non-GM strategies. Extraction and recovery of this oil from biomass will also not be a considerable issue, since extrusion technologies and/or solvent-based approaches may be adapted to recovery of oil before other uses. It should be recognized that even a minor percentage of oil in biomass represents a revolutionary change in oil production. For example, a conservative estimate of TAG content at 3% on a dry weight basis would be comparable to total yields from oilseed crops. Yields of biomass from switchgrass are in the range of 5 tons of dry matter per acre (Fuentes and Taliaferro, 2002). A 3% yield of oil from this amount of biomass would represent 300 lbs of oil/acre, which is comparable to the current soybean oil yield (335 lbs/acre). A goal of 10% oil yield from plant vegetative tissues would be realistic in terms of causing minimal physiological consequences and representing a relatively minor impact on overall carbon allocation, especially if this is coordinated with senescence (e.g. expression of a sequence designed for suppression of expression of a At4g24160 polypeptide or homolog is placed under the control of a senescence-specific promoter) or chemical treatment. This amount of oil from biomass (1000 lbs/acre) would rival the highest oilseed crop yields in the temperate regions of the world. Canola is currently the highest yielder at about 850 lbs/acre, thus making biofuel production more economical. The success in *Arabidopsis* supports a rapid translation to crop systems. This strategy could be readily adapted for use in food crops, where oils could be recovered from vegetative crop residues (e.g., corn stover), or, for use with dedicated energy crops where oil could be recovered from, for instance, stems and leaves prior to carbohydrate utilization.

In particular embodiments, the neutral lipid content of the vegetative portions of such plants, with a decreased activity of an AT4G24160 gene product or homolog thereof, is increased. An mRNA sequence of the At4g24160 gene is found in SEQ ID NO:6. The amino acid sequence of the full length polypeptide encoded at the At4g24160 locus is given in SEQ ID NO:7, and is also found at GenBank Accession B029749. Differences between the two polypeptides encoded by the At4g24160 locus are shown in FIG. 1. Altered plants with a reduced activity (partial or complete reduction in function) of a At4g24160 homolog, as compared to a wild type, for example, have dramatically increased levels of TAG in their vegetative tissues. The neutral lipid content of such plant vegetative parts may further be altered by cultural methods, for instance by exposing a plant to low temperature or to an increased concentration of ozone (i.e. above ambient).

In another aspect, the invention provides methods for screening crop plants, including cultivars, accessions, and breeding lines and materials of the crop plants listed above, for the presence of a mutation in a At4g24160 gene, or homolog thereof present in their genomes. Such screening may, in certain embodiments, be phenotypic (e.g. by chemically, visually, or microscopically assessing the oil content, neutral lipid content, or TAG content of plant vegetative tissues), or genetic (e.g. by detection based on nucleic acid probes or primers). In certain embodiments, use of an immuno-technique may be employed. In other embodiments, a method may employ marker-assisted breeding to identify plants, including cultivars or breeding lines, displaying a trait of interest, such as elevated levels of neutral lipids in vegetative portions of plant biomass.

At4g24160 Homolog Isolation

Isolation of additional At4g24160 homologs from other plant species may be accomplished by laboratory procedures well known and commonly used in the art. Standard techniques are used for identification, cloning, isolation, amplification, and purification of nucleic acid sequences and polypeptides. These techniques and various others are generally performed as described for instance in Sambrook et al., 1989. Genome walking techniques may be performed according to manufacturer's specifications (CLONTECH Laboratories, Inc., Palo Alto, Calif.).

One such technique for isolation of At4g24160-homologs is the use of oligonucleotide probes based on sequences disclosed in this specification to identify the desired gene in a cDNA or genomic DNA library. To construct genomic libraries, large segments of genomic DNA are generated by digestion with restriction endonucleases and then ligating the resultant segments with vector DNA to form concatemers that can be packaged into an appropriate vector. To prepare a cDNA library, mRNA is isolated from the desired organ, such as seed tissue, and a cDNA library is prepared from the mRNA.

A cDNA or genomic DNA library can be screened using a probe based upon the sequence of a cloned At4g24160 gene (e.g. SEQ ID NO:6), or the sequence encoding another identified homolog (e.g. SEQ ID NOs:18-36). Probes may be used to hybridize with genomic DNA or cDNA sequences to isolate homologous genes in the same or different plant species. Usefully employed such probes include, without limitation, 5' UTRs which, may function as promoters. Alternatively, antibodies raised against an At4g24160 polypeptide, or homolog thereof, can be used to screen an mRNA expression library to isolate sequences of interest. At4g24160 homologs may also be identified in silico, for instance by similarity-based database searches as described below.

Nucleic acid sequences can be screened for the presence of protein encoding sequence that is homologous to genes of other organisms with known protein encoding sequence using any of a variety of search algorithms. Such search algorithms can be homology-based or predictive-based. Similarity-based searches (e.g., GAP2, BLASTX supplemented by NAP and TBLASTX) can detect conserved sequences during comparison of DNA sequences or hypothetically translated protein sequences to public and/or proprietary DNA and protein databases. Existence of a gene is inferred if significant sequence similarity extends over the majority of the target gene. Since such methods may overlook genes unique to the source organism, for which homologous nucleic acid molecules have not yet been identified in databases, gene prediction programs may also be used. Gene prediction programs generally use "signals" in the sequences, such as splice sites or "content" statistics, such as codon bias, to predict gene structures (Stormo, 2000).

Alternatively, the nucleic acids of interest can be amplified from nucleic acid samples using amplification techniques. For example, polymerase chain reaction technology can be used to amplify the sequences of a At4g24160 gene or At4g24160 gene homolog directly from genomic DNA, from cDNA, from genomic libraries, and cDNA libraries. PCR and other in vitro amplification methods may also be useful, for example, in cloning nucleic acids sequences that code for proteins to be expressed, to make nucleic acids to use as probes for detecting the presence of desired mRNA in samples, for nucleic acid sequencing, or for other purposes.

Appropriate primers and probes for identifying At4g24160 and homolog sequences from plant tissues are generated from comparisons of the sequences provided herein. For a general overview of PCR, see, Innis, et al., eds., 1990.

As noted above, the nucleic acids used in the context of the present invention are characterized by the presence of sequence encoding an AT4G24160 homolog polypeptide. Primers that specifically amplify At4g24160 coding regions of the exemplified genes may be useful for identification of particular AT4G24160 homologs from different crop species. Primers suitable for this purpose are designed based on the sequence of At4g24160 homolog genes disclosed herein (e.g. SEQ ID NOs:18-36), using well known methods.

In certain embodiments of the invention, down-regulation of the activity of a polypeptide encoded by a gene comprising any of SEQ ID NO:18-36 may be accomplished using antisense-mediated-, or dsRNA-mediated-, or other forms of RNA-mediated-interference (RNAi), as is well known in the art. Methods for identification of candidate nucleotide sequences for RNA mediated gene suppression, and design of oligonucleotides and constructs to achieve RNA-mediated gene suppression, are well known (e.g. Reynolds et al., 2004; Lu and Mathews, 2008). DNA sequences of genes encoding At4g24160 homologs may also be mutagenized, such as by T-DNA insertion, transposon insertion, or homologous recombination, to create plants comprising down-regulated activity of a At4g24160 homolog.

PCR or other primers may be used under standard PCR conditions, preferably using nucleic acid sequences as identified in EST libraries or other GenBank accessions as a template. The PCR products generated by any of the reactions can then be used to identify nucleic acids useful in the context of the present invention by their ability to hybridize to known At4g24160 homolog genes found in GenBank and other databases, as well as their ability to mediate down-regulation of activity of a At4g24160 homolog such as those given in FIG. 1, FIG. 9, and SEQ ID NOs:18-36. Alternatively, primers that specifically hybridize to highly conserved regions in a At4g24160 gene or At4g24160 gene homolog can be used to amplify sequences from widely divergent plant species such as switchgrass, canola, soybean, and tobacco, for example.

Polynucleotides may be synthesized by well-known techniques, as described in the technical literature. See, e.g., Carruthers et al., 1982, and Adams et al., 1983. Double-stranded DNA fragments may then be obtained either by synthesizing the complementary strand and annealing the strands together under appropriate conditions, or by adding the complementary strand using DNA polymerase with a suitable primer sequence.

In a particular embodiment, the expression of a At4g24160 gene or gene homolog is reduced relative to the level of expression found in an otherwise isogenic wild-type plant. This reduction in expression may be partial or complete, relative to the expression found in cells of an otherwise isogenic wild-type plant. Reduction in activity or function of the polypeptide encoded by At4g24160, or homolog thereof, may be accomplished by methods well known in the art including through co-suppression, and RNAi-mediated approaches, including via dsRNA and siRNA, among others.

DsRNA or siRNA nucleotide sequences comprise double strands of polymerized ribonucleotide and may include modifications to either the phosphate-sugar backbone or the nucleoside. Modifications in RNA structure may be tailored to allow specific genetic inhibition. In one embodiment, the dsRNA molecules may be modified through an enzymatic process so that siRNA molecules may be generated. Alternatively, a construct may be engineered to express a nucleotide segment for use in an miRNA- or siRNA-mediated resistance approach. The siRNA can efficiently mediate the down-regulation effect for target genes. This enzymatic process may be accomplished by utilizing an RNAse III enzyme or a DICER enzyme of the RNAi pathway (Elbashir et al., 2001; Hamilton and Baulcombe, 1999).

Use of variants of At4g24160 sequences may be employed, for instance, by preparing mutant At4g24160 homolog alleles. In vitro mutagenesis and selection, site-directed mutagenesis, or other means can be employed to obtain mutations of naturally-occurring At4g24160 homolog sequences. Such mutagenesis may, for instance, comprise use of transposon or T-DNA insertions Plant Transformation To use isolated sequences in the above techniques, recombinant DNA vectors suitable for transformation of plant cells are prepared. Techniques for transforming a wide variety of higher plant species are well known and described in the technical and scientific literature. See, for example, Weising et al., 1988; and Sambrook et al., 1989. Methods of plant cell culture are well known in the art. A DNA sequence coding for the desired polypeptide, for example a cDNA sequence encoding a full length protein, will preferably be combined with transcriptional and translational initiation regulatory sequences that will direct the transcription of the sequence from the gene in the intended tissues of the transformed plant.

Vectors used for plant transformation may include, for example, plasmids, cosmids, yeast artificial chromosomes (YACs), bacterial artificial chromosomes (BACs), plant artificial chromosomes (PACs), or any suitable cloning system. It is contemplated the utilization of cloning systems with large insert capacities will allow introduction of large DNA sequences comprising more than one selected gene. Introduction of such sequences may be facilitated by use of BACs or YACs, or even PACs. For example the use of BACs for *Agrobacterium*-mediated transformation was disclosed by Hamilton et al., 1999.

Particularly useful for transformation are expression cassettes that have been isolated from such vectors. DNA segments used for transforming plant cells will, of course, generally comprise the cDNA, gene or genes that one desires to introduce into and have expressed in the host cells. These DNA segments can further include structures such as promoter, enhancers, 3' untranslated regions (such as polyadenylation sites), polylinkers, or even regulatory genes as desired. The DNA segment or gene chosen for cellular introduction may encode a protein that will be expressed in the resultant recombinant cells resulting in a screenable or selectable trait and/or will impart an improved phenotype to the resulting transgenic plant. However, this may not always be the case, and the present invention also encompasses transgenic plants incorporating non-expressed transgenes. Preferred components are described below.

A number of promoters that are active in plant cells have been described in the literature, and are preferred elements included in the context of the present invention. Such promoters would include but are not limited to those isolated from the following genes: nopaline synthase (NOS; Ebert et al., 1987) and octopine synthase (OCS): cauliflower mosaic virus (CaMV) 19S (Lawton et al. 1987) and 35S (Odell et al., 1985), as well as the enhanced CaMV 35S promoter (e35S; described by Kay et al., 1987); figwort mosaic virus (FMV) 35S; the small subunit of ribulose bisphosphate carboxylase (ssRUBISCO, a very abundant plant polypeptide); napin (Kridl et al., 1991); Adh (Walker et al., 1987); sucrose synthase (Yang et al., 1990); tubulin; actin (Wang et al., 1992); cab (Sullivan et al., 1989); PEPCase (Hudspeth et al., 1989); 7S-alpha'-conglycinin (Beachy et al., 1985); R gene complex promoters (Chandler et al. 1989); tomato E8; patatin; ubiquitin; mannopine synthase (mas); soybean seed protein glycinin (Gly); soybean vegetative storage protein (vsp); waxy; Brittle; Shrunken 2; Branching enzymes I and II; starch synthases; debranching enzymes; oleosins; glutelins; globulin 1; BETL1; and *Arabidopsis* banyuls promoter. The rice actin 1 promoter, the AGL11 promoter, the BETL1 promoter, and the e35S promoter may find use in the practice of the present invention. All of these promoters have been used to create various types of DNA constructs that have been expressed in plants (see, for example, Rogers et al., WO 84/02913).

Promoter hybrids can also be constructed to enhance transcriptional activity (Hoffman, U.S. Pat. No. 5,106,739, herein incorporated by reference), or to combine desired transcriptional activity, inducibility, and tissue or developmental specificity. Promoters that function in plants include but are not limited to promoters that are classified as, among others, inducible, viral, synthetic, constitutive, tissue-specific, developmentally-regulated, chemically or environmentally inducible, or senescence-related, for instance as described (Odell et al., 1985). Promoters that are tissue specific, tissue-enhanced, or developmentally regulated are also known in the art and envisioned to have utility in the practice of this present invention. For instance, a tissue specific promoter, such as the ST-LS1 promoter (e.g. Stockhaus et al., 1989), that is functional in plant vegetative tissues such as leaves, stems, and/or roots, may be of use. Such a promoter may also be expressed to at least some degree in seed or embryo tissues. In certain embodiments, the promoter to be utilized may be expressed preferentially in green parts of a plant such as leaves or stems. A senescence-related promoter (e.g. from SAG12) may also be utilized.

The promoters used in the present invention may be modified to affect their control characteristic. Promoters can be derived by means of ligation with operator regions, random or controlled mutagenesis, or other means well known in the art. Furthermore the promoter regions can be altered to contain multiple enhancer sequences to assist in elevating gene expression. Examples of such enhancer sequences have been reported (Kay et al., 1987).

Where an enhancer is used in conjunction with a promoter for the expression of a selected protein, it is believed that it will be preferred to place the enhancer between the promoter and the start codon of the selected coding region. However, one could also use a different arrangement of the enhancer relative to other sequences and still realize the beneficial properties conferred by the enhancer. For example, the enhancer could be placed 5' of the promoter region, within the promoter region, within the coding sequence, or 3' of the coding region. The placement and choice of sequences used as enhancers is known to those of skill in the art in light of the present disclosure. Transformation constructs prepared in accordance with the current invention will typically include a 3' untranslated region (3' UTR), and typically contains a polyadenylation sequence. One type of 3' UTR that may be used is a 3' UTR from the nopaline synthase gene of *Agrobacterium tumefaciens* (NOS 3'-end; Bevan et al., 1983). Other 3' UTR sequences can be used and are commonly known to those of skill in the art.

A number of selectable marker genes are known in the art and can be used in the present invention (Wilmink and Dons, 1993). By employing a selectable or screenable marker gene in addition to the gene of interest, one can provide or enhance the ability to identify transformants. Useful selectable marker genes for use in the present invention would include genes that confer resistance to compounds such as antibiotics like kanamycin and herbicides like glyphosate or dicamba. Other selectable markers known in the art may also be used and would fall within the scope of the present invention.

DNA constructs of the present invention may be introduced into the genome of the desired plant host by a variety of techniques that are well known in the art. For example, the DNA construct may be introduced directly into the genomic DNA of the plant cell using techniques such as electroporation and microinjection of plant cell protoplasts, or the DNA constructs can be introduced directly to plant tissue using DNA particle bombardment.

Microinjection techniques are known in the art and well described in the scientific and patent literature. The introduction of DNA constructs using polyethylene glycol precipitation is described in Paszkowski et al., 1984. Electroporation techniques are described in Fromm et al., 1985. Ballistic transformation techniques are described in Klein et al., 1987.

Alternatively, the DNA constructs may be combined with suitable T-DNA flanking regions and introduced into a conventional *Agrobacterium tumefaciens* host vector. The virulence functions of the *Agrobacterium tumefaciens* host direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example, Horsch, 1984; and Fraley, 1983.

After transformation by any of the above transformation techniques, the transformed plant cells or tissues may be grown in an appropriate medium to promote cell proliferation and regeneration. Plant regeneration from cultured protoplasts is described in Evans et al., 1983; and Binding, Regeneration of Plants, Plant Protoplasts, pp. 21 73, CRC Press, Boca Raton, 1985. For gene gun transformation of wheat and maize, see, U.S. Pat. Nos. 6,153,812 and 6,160,208. See also, Christou, 1996. See, also, U.S. Pat. Nos. 5,416,011; 5,463,174; and 5,959,179 for *Agrobacterium*-mediated transformation of soy; U.S. Pat. Nos. 5,591,616 and 5,731,179 for *Agrobacterium*-mediated transformation of monocots such as maize; and U.S. Pat. No. 6,037,527 for *Agrobacterium*-mediated transformation of cotton. Other Rhizobiaceae may be used for plant cell transformation as well (e.g. Broothaerts et al., 2007).

Methods for Identifying and Breeding Plant Germplasm

In still yet another aspect, the invention provides a method of obtaining crop plant germplasm, comprising the steps of: a) identifying at least a first polymorphism in a crop plant genomic region conferring reduced function or expression of a plant At4g24160 homolog; b) assaying other crop plants of the same order, family, genus, or species for the presence of the polymorphism; and c) selecting at least a first crop plant comprising the polymorphism. In certain embodiments the polymorphism results in a loss of function phenotype. In other embodiments, the polymorphism may comprise a full or partial deletion or a point mutation in the gene sequence of the At4g24160 homolog. Detecting the polymorphism may be carried out by any method, for instance PCR, single strand conformational polymorphism analysis, denaturing gradient gel electrophoresis, cleavage fragment length polymorphism analysis and/or DNA sequencing. Since the cgi58 mutant phenotype of interest is a loss-of-function mutation, many of the commonly used techniques for screening mutants (e.g., TILLING; McCallum et al., 2000) in commercial crop species may be adapted to identify cgi58 mutant alleles.

In still yet another aspect, the invention provides a method of plant breeding comprising the steps of: a) identifying in a crop plant a genomic region conferring reduced function or expression of a plant At4g24160-homolog allele; b) selecting at least a first crop plant comprising the genomic region; and c) crossing the first crop plant to a second crop plant to produce progeny plants comprising the genomic region. In certain embodiments the genomic region comprises a sequence polymorphism relative to the nucleotide sequence of the corresponding genomic region of a wild-type plant. The polymorphism may comprise, for instance, an insertion, a deletion, or a single nucleotide polymorphism (SNP) at the locus encoding At4g24160, or homolog thereof. Identifying the polymorphism may be carried out by any method, including PCR, single strand conformational polymorphism analysis, denaturing gradient gel electrophoresis, cleavage fragment length polymorphism analysis and/or DNA sequencing, among others. The method may further comprise the step of: d) selecting a progeny plant comprising the polymorphism and crossing the progeny plant with a third crop plant to produce additional progeny plants. In the method the second and third plants may be of the same variety. In certain embodiments, the method further comprises repeating step d) about 2-10 times.

Uses for Vegetative Plant Tissues with Enhanced Lipid Content

Common uses for oils comprising neutral lipids include the preparation of food for human consumption, feed for non-human animal consumption and industrial uses such as for preparation of biofuels. As used herein, "industrial use" or "industrial usage" refers to non-food and non-feed uses for products prepared from plant parts prepared according to the present invention. As used herein, "biofuel" refers to a fuel combusted to provide power, heat, or energy, e.g. for an internal combustion engine, comprising at least 1%, 5%, 10%, 20% or more, by weight, of an oil, or product thereof, produced from a plant of the present invention, or by a method of the present invention. Also included in this invention are plants, plant cell cultures, and plant parts thereof, including seeds, containing one or more various transgene construct(s) or mutagenized loci utilized for decreasing expression of At4g24160 or a homolog thereof, oil obtained from the vegetative tissues of such plants and cells and progeny thereof, animal feed derived from the processing of such tissues, the use of the foregoing oil in food, animal feed, biofuels, cooking oil or industrial applications, and products made from the hydrogenation, fractionation, interesterification or hydrolysis of such oil.

The following examples are included to demonstrate specific embodiments of the present invention. It should be appreciated by those of skill in the art that the techniques disclosed in the examples that follow represent techniques discovered by the inventors to function well in the practice of the present invention, and thus can be considered to constitute exemplary modes for its practice. However, those of skill in the art should, in light of the present disclosure, appreciate that many changes can be made in the specific embodiments that are disclosed and still obtain a like or similar result without departing from the spirit and scope of the present invention.

EXAMPLES

Example 1

Oil Bodies Accumulate in Tissues of *Arabidopsis* CGI58 Gene Knockout Lines

Two *Arabidopsis* lines with T-DNA disruptions in the first exon or first intron of the At4g24160 locus (SALK_127083 and SALK_0136871; *Arabidopsis* Biological Resource Center, Ohio State University, Columbus, Ohio) were obtained and characterized. There appeared to be no obvious growth differences between the mutant and wildtype *Arabidopsis* plants. The corresponding non-segregating homozygous mutant lines and the location and orientation of the T-DNA insert in the 0136871 were verified by DNA sequencing. The T-DNA insertion found in SALK_0136871 is annotated in the first exon of the At4g24160 locus, while the insertion found in SALK_127083 is found near the first exon of the At4g24160 locus. As annotated by the *Arabidopsis* information site (www.arabidopsis.org) it is located in the first intron.

Figure 3:
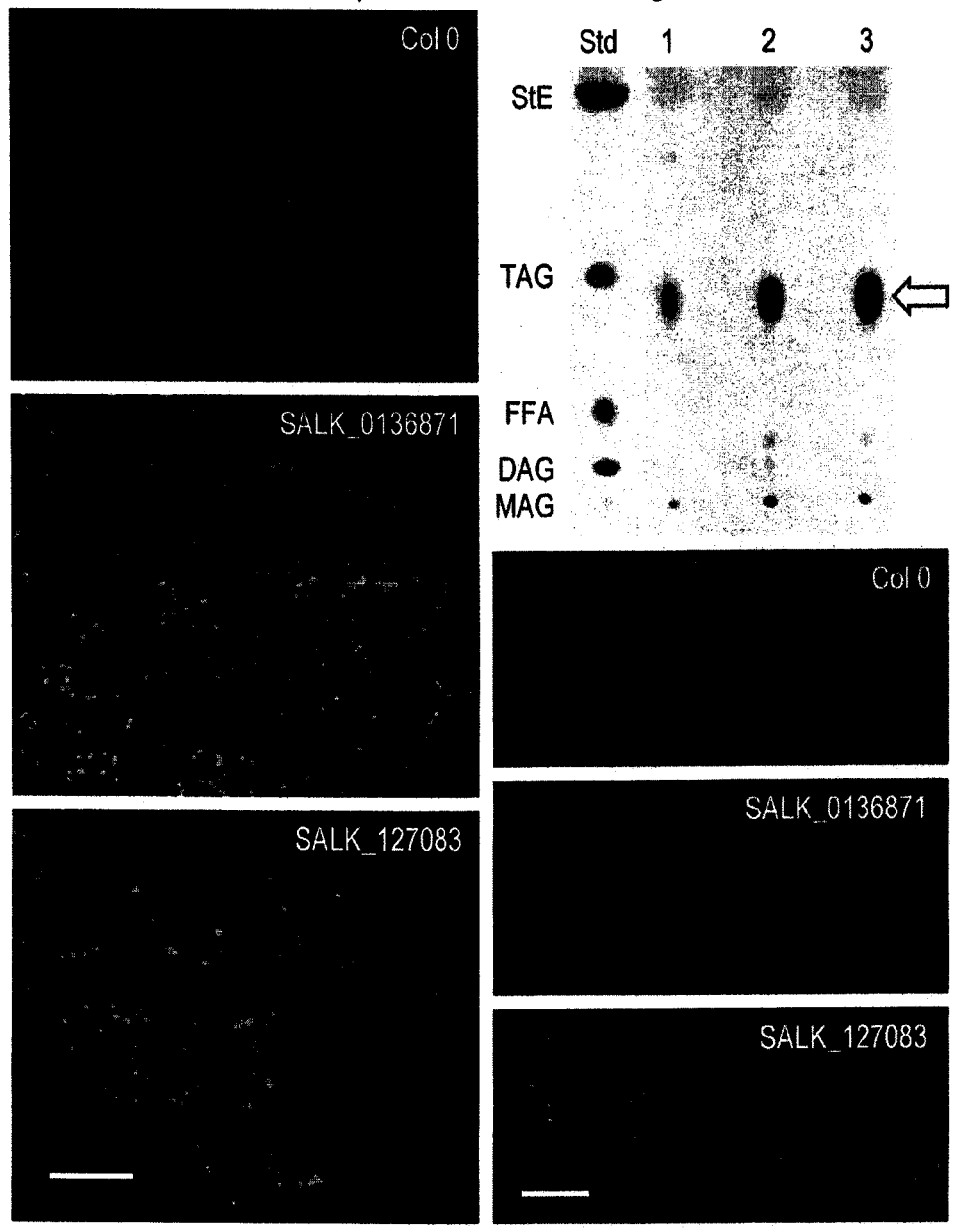
FIG. 3: Representative confocal microscope images of WT (Col 0), and two T-DNA mutant lines stained with Nile red to reveal lipid bodies (left) in 21-day old seedlings (petiole region of true leaves)(left). Bar=20 microns. TLC separation of neutral lipids isolated from 14-day old seedlings (450 mg FW each) of WT (lane 1), and both T-DNA mutants (lanes 2 and 3)(upper right). Standards are sterylesters (StE), triacylglycerols (TAG) (arrow), free fatty acids (FFA), diacylglycerols (DAG), and monoacylglycerols (MAG). Representative epifluorescence images of purified lipid bodies from 14-day old wild-type and T-DNA mutant seedlings (stained with BODIPY 493). Bar=20 microns (lower right).
Figure 7B:
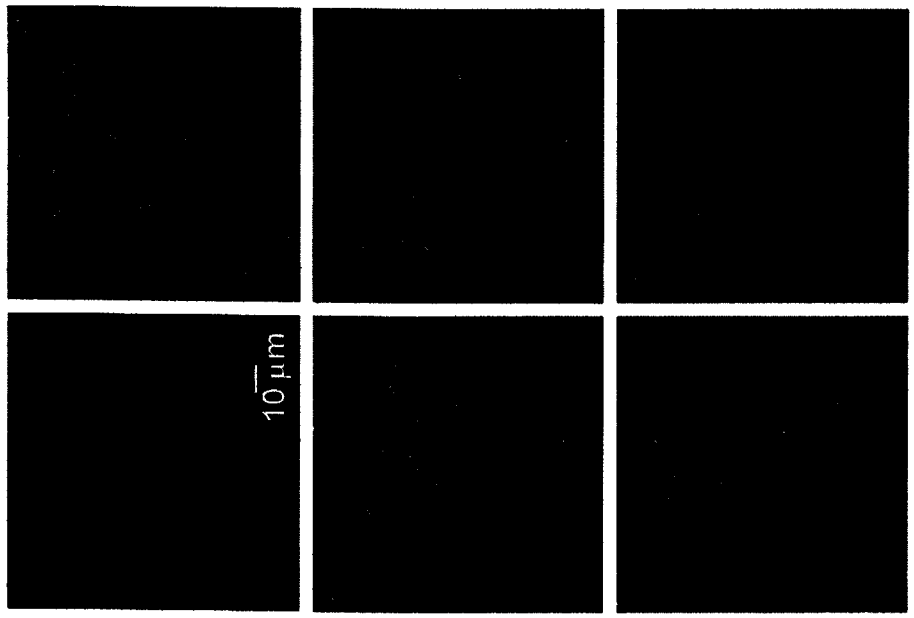
FIG. 7A and FIG. 7B: shows representative confocal fluorescence images of leaves of 40 day old *Arabidopsis* plants (wild-type and T-DNA insertional mutant line Salk_136871). Leaves were fixed in paraformaldehyde and stained with BODIPY 493/520 (Invitrogen), a neutral lipid-specific stain. BODIPY-fluorescence and chlorophyll autofluorescence were imaged together. Excitation of both chlorophyll and BODIPY stain were at 493 nm. Emission wavelength for chlorophyll was 692 nm, exposed for 0.4 seconds. Emission wavelengths for BODIPY-stained lipid bodies was 520 nm, exposed for 10 seconds. Scale bar=10 microns. Images were acquired with a Zeiss 200M optical microscope fitted with a CSU-10 Yokogawa confocal scanner (McBain Instruments, Simi Valley, Calif.) and captured with a digital camera (Hamamatsu, Phoenix, Ariz.).
Figure 7A:
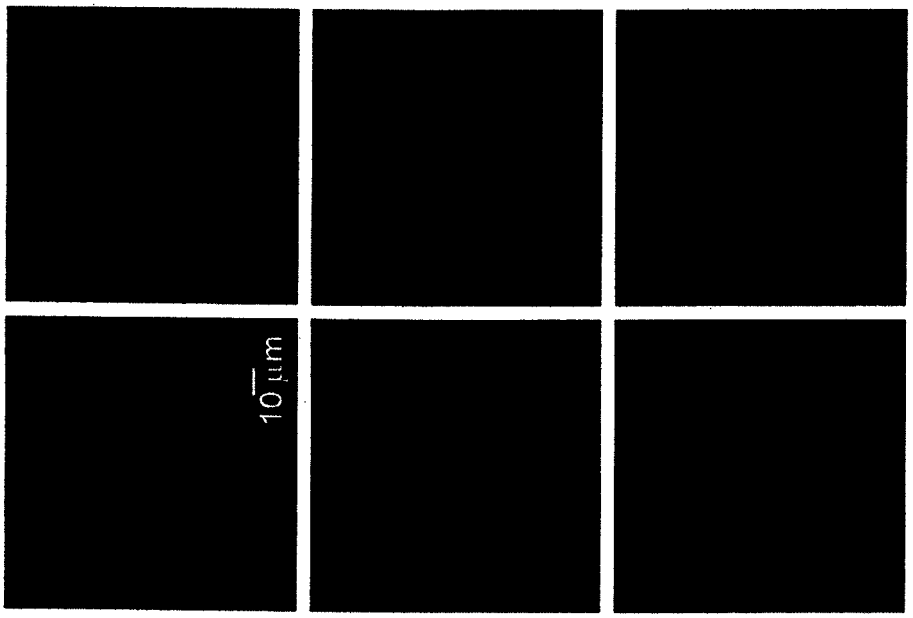
Figure 8:
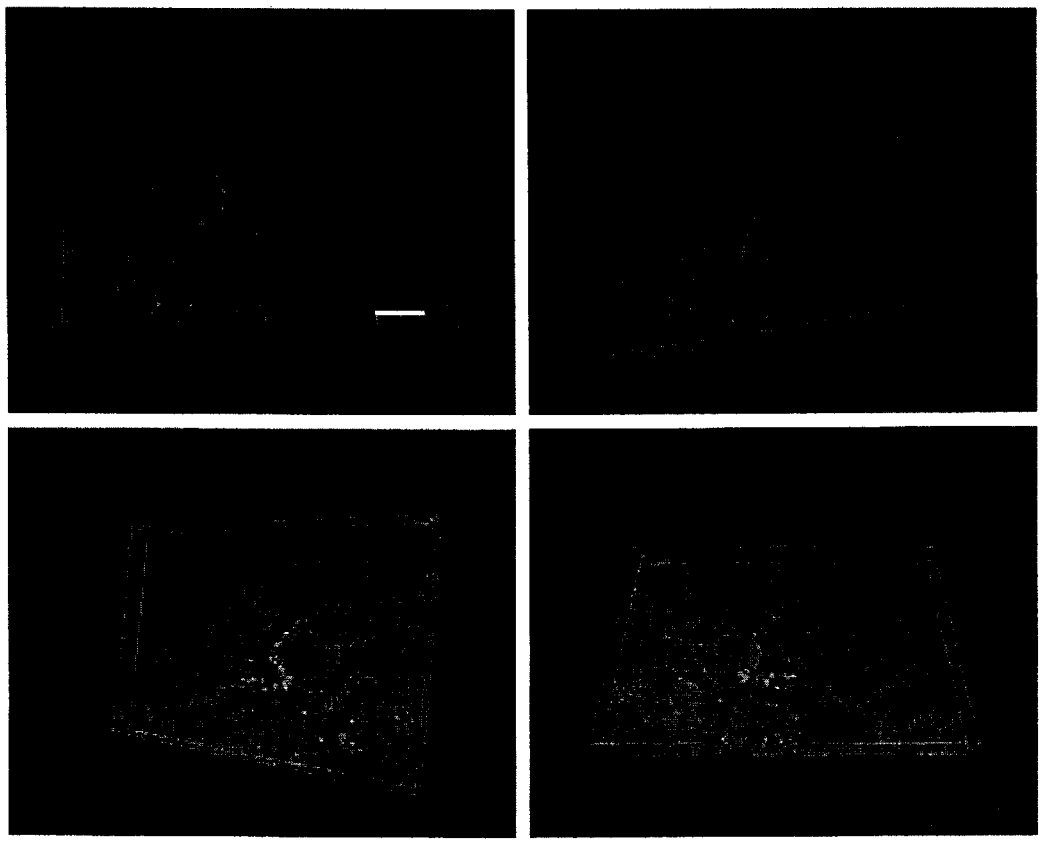
FIG. 8: shows a three-dimensional projection of lipid droplets in SALK_136871 (cgi58 mutant) mesophyll cells of mature *Arabidopsis* leaves, about 40 days after emergence. The projection was prepared from a Z-stack of thirteen optical sections imaged by confocal fluorescence micrographs acquired from the T-DNA insertional mutant line. Leaves were prepared and imaged as in FIG. 7. Each image is a 1 micron section (Scale bar=20 microns). Lipid bodies are abundant throughout the cytoplasm of these mutants. Lipid droplets are distinctly separated from the chloroplasts in these cells.

The *Arabidopsis* cgi58-homolog T-DNA mutants were stained with either Nile-red or BODIPY 493 (e.g. Invitrogen, or Molecular Probes, Inc., Eugene, Oreg.), two selective neutral lipid stains, and found to show neutral lipid particles. This lipid droplet phenotype was found in petioles, roots and leaves of *Arabidopsis* plants imaged at 14-21 days after germination, and in leaves of 28-35 day old plants (e.g. see FIGS. 7-8). Representative images of petioles from leaves from 14-day old wild-type [Col 0] and both T-DNA mutant lines are shown (FIG. 3 left). To further support the identity of these stained particles as lipid bodies, subcellular fractions were isolated from homogenates of 14-day old wild-type seedlings and from seedlings of both T-DNA lines (by flotation 3× through sucrose medium according to Chapman and Trelease, 1991). Isolated lipid bodies were stained with BODIPY 493 (and Nile red, not shown), and were substantially more numerous in purified fractions from T-DNA mutants than from corresponding wild-type (Col 0; FIG. 3 lower right). In addition to subcellular fractionation, an increase in neutral lipid content was confirmed in both T-DNA mutants, most of which comprised TAGs (FIG. 3 upper right). Taken together, these results indicated that a disruption in the At4g24160 locus, encoding a putative homolog of human CGI58, lead to an accumulation of TAG in vegetative tissues of plants, and that this TAG is compartmentalized into lipid droplets in the cytoplasm of most all vegetative cells. Because only a small number of lipid bodies are normally found in vegetative tissues, this is evidently due to an elaboration of an otherwise normal cellular process of transient neutral lipid storage and recycling.

Example 2

*Arabidopsis* CGI58 is Alternatively Spliced

The At24160 gene gives rise to two alternative transcripts (FIG. 1): one transcript, At4g24160.1, (SEQ ID NO:6; see GenBank Accession NM_118548) predicted to encode the full-length protein (SEQ ID NO:7), while the other transcript, At4g24160.2 (SEQ ID NO:37), encodes a shorter protein (SEQ ID NO:38) that lacks the last two exons but possesses a longer 3' untranslated region (UTR). RT-PCR confirms the occurrence of both transcripts in *Arabidopsis* tissues (and lack thereof in mutants) (FIG. 1) and both cDNAs have been isolated (FIG. 1). The nucleotide sequences of the splice variants were confirmed by DNA sequencing.

Expression of At4g24160 isoforms in different tissues and different developmental stages was followed, to further characterize the temporal profile and location of neutral lipid accumulation in vegetative tissues of cgi58 mutant plants. Transcript abundance was estimated by RT-PCR using a one-Step RT-PCR system from Takara Bio (Shiga, Japan). The following transcript-specific primers were used for At4G24160:

```
                                        (SEQ ID NO: 39)
     5'-ATGAACTTGAGCCGTTTTGCTTCGAGA-3';

(SEQ ID NO: 40)
     5'-AACCAATCGTAGACCATCTAGGAG-3';
     and (SEQ ID NO: 41)
     5'-GCAATGTTTTGGTGGACATACCT-3'.
```

Both long (R1) and short (R2) transcripts were amplified with the same forward primer (SEQ ID NO:39) but different reverse primers (SEQ ID NOs:40-41, respectively). RT-PCR reactions were performed with 0.2 μg total RNA and the following RT-PCR conditions: 42° C. for 15 min, followed by 35 cycles of 95° C. for 2 min, 94° C. for 10 s, 56° C. for 25 s, 72° C. for 1 min 30 s. Amplification of ubiquitin transcripts was used as a control for comparisons. Amplimers were separated by agarose gel (1%) electrophoresis and visualized by ethidium bromide staining.

Figure 13:
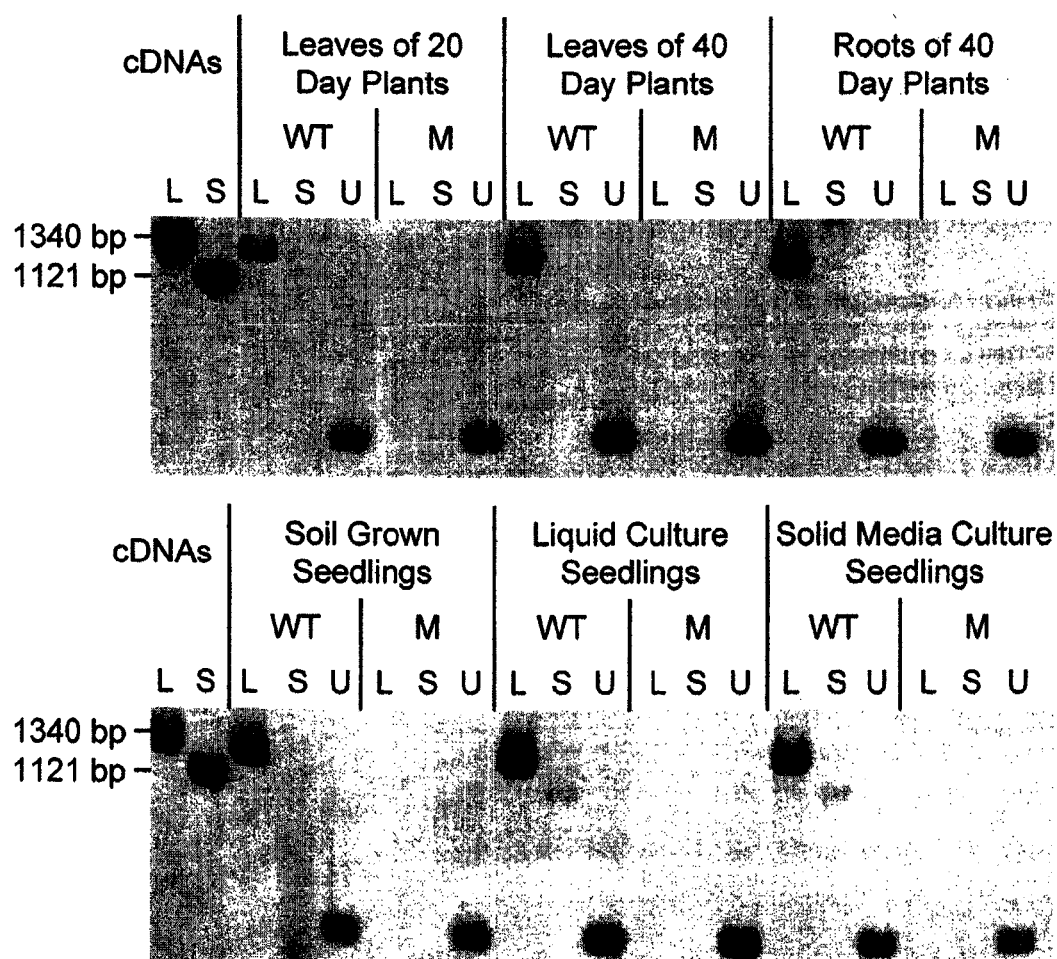
FIG. 13: shows expression of At4g24160 isoforms in different tissues and different developmental stages, as determined by semi-quantitative RT-PCR. Lane legends are as follows: "L"=full-length transcript; "S"=alternatively spliced shorter transcript for a smaller CGI-58 protein which lacks the acyltransferase domain; "U"=ubiquitin control. "WT"=RNA isolated from wild-type *Arabidopsis*; "M"=RNA isolated from cgi58 mutant *Arabidopsis*.

Thus, cDNAs corresponding to the two alternatively spliced At4g24160 (At4g24160.1 and At4g24160.2) transcripts were amplified from seedling mRNA and used to verify sequences predicted in FIG. 1. Analysis of mRNA abundance using semi-quantitative RT-PCR revealed that the longer splice variant (1,340 bp; see FIG. 13, lanes labeled "L" in each sample) was expressed in both leaves and roots of wild-type (WT) plants cultivated under a variety of conditions. The shorter splice variant (1,121 bp; FIG. 13 lanes labeled "S"), however, was only detected at very low levels in leaves of 40 day old plants, and seedlings grown on liquid or solid media. Notably, no transcripts for either the longer or shorter form of At4g24160 were detected in the T-DNA mutant plants (M). The level of ubiquitin transcripts expressed in the same wild-type and mutant plants (lanes labeled "U") are shown as a control.

Using semi-quantitative RT-PCR, it was found that the longer (full-length) transcript was expressed in all wild-type tissues examined, whereas the shorter, truncated transcript was expressed, albeit at low levels, only in leaves of wild-type mature plants and in seedlings cultured in liquid or solid media (FIG. 13). The longer (full-length) transcript was also the major form detected in vegetative tissues of soil-grown, wild-type plants (FIG. 13). Neither transcript was detected in any tissues from mutants, confirming the lack of CGI-58 expression in these plants. Based on these results, it is likely that the larger CGI-58 protein product is responsible for regulating neutral lipid accumulation in vegetative tissues. The physiological relevance of the alternatively-spliced smaller CGI-58 protein, which lacks the acyltransferase domain, is presently unclear.

Example 3

The Arabidopsis at4g24160 Protein Products are CGI58 Homologs

An alignment of CGI58 proteins from various species indicates the presence of several conserved domains as well as specific amino acid motifs that are known to be important for certain enzyme activities. For instance, Domain 2, which starts at about position 178 in FIG. 1, contains a GXSXG (SEQ ID NO:1) motif (boxed in FIG. 1) where X is any amino acid) that is associated with esterase/lipase/thioesterase function (Schrag and Cygler, 1997), and in mammalian CGI58 the critical serine residue in the middle of this motif has been substituted with an asparagine (Lefèvre et al., 2001; see FIG. 1). While this substitution is known to disrupt the esterase/lipase function, the plant homologs do have a serine at this position, suggesting that the plant (and *C. elegans*) proteins might have lipase activities themselves (rather than stimulate a lipase, like the mammalian proteins). A second motif ($HX_4D$) is present towards the C-terminal end of the proteins (also boxed in FIG. 1), and this motif has been implicated in acyltransferase activity (Heath and Rock, 1998). Whether this motif is important for the LPAAT activity of mammalian (or *Arabidopsis*) CGI58 polypeptides, and homologs thereof, is unknown, However, this motif is absent in the short form of the *Arabidopsis* protein (FIG. 2A; due to alternative splicing).

Example 4

Enhancement of Oil Content in Vegetative Tissues of Plants

Figure 4:
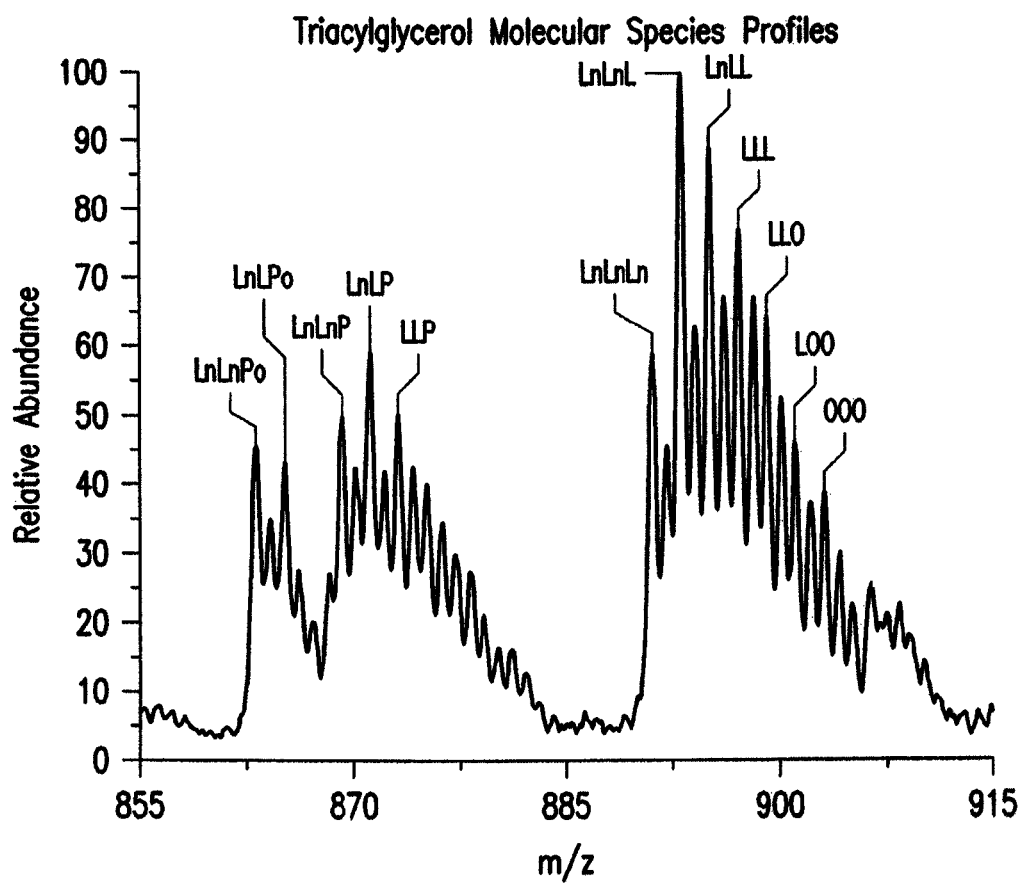
FIG. 4: Nanospray ionization and mass spectroscopy of triacylglycerol molecular species in *Arabidopsis* Col 0 wild-type seedlings. Full scan, positive ion nanospray-MS species were identified as ammonium adducts $(M+NH_4)+$ using a ProXeon nanospray ionization source (ProXeon Biosystems, Odense, Denmark) and analyzed with a LCQ Deca XP Plus quadrupole ion trap (Thermo Fisher Scientific, Waltham, Mass.). A 50× dilution of reconstituted TAG extract in chloroform was prepared with 1:1 (v/v) chloroform:methanol plus 10 mM ammonium acetate. Typical scanning conditions were carried out in positive ion mode with a 0.8-1.0 kV spray voltage, scan range of 700-1000 m/z, 275° C. capillary temperature, 3 microscans per second with a maximum injection time of 200 msec.
Figure 5:
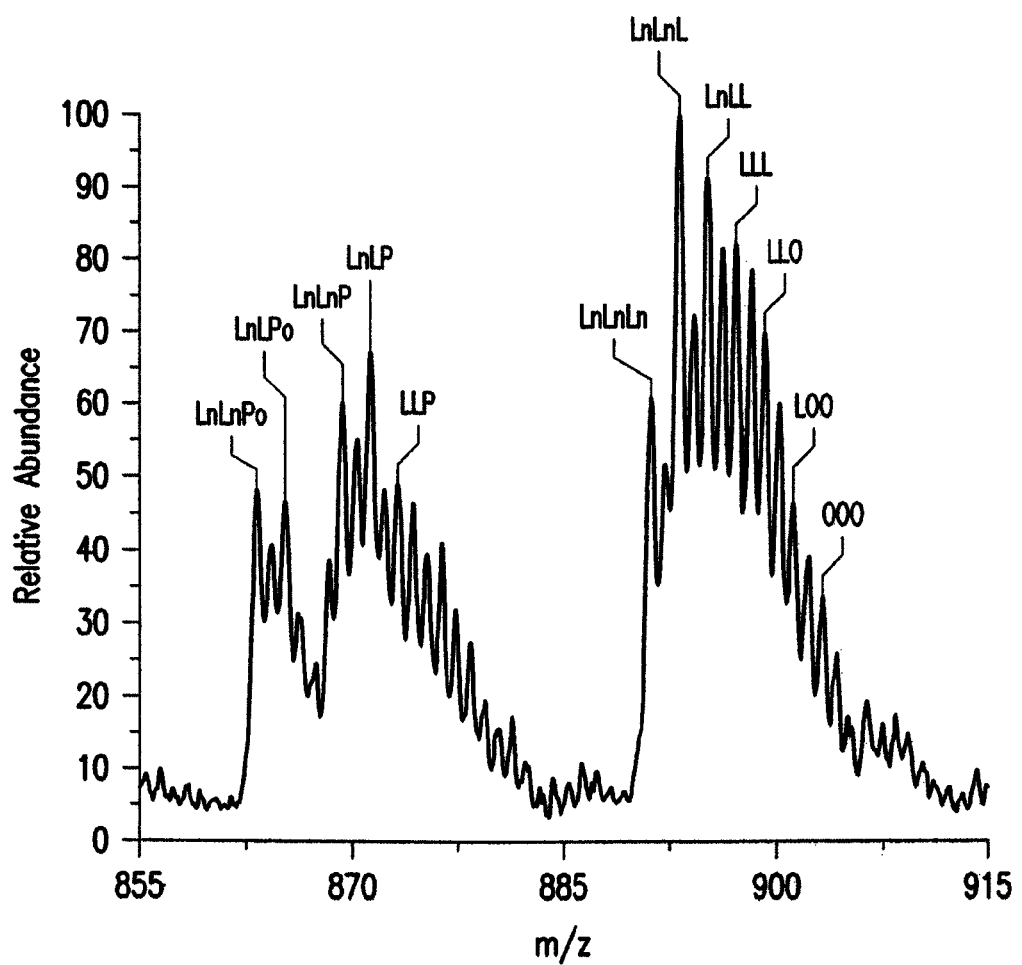
FIG. 5: Same as for FIG. 4, but carried out on At4g24160 T-DNA exon insertional line SALK_0136871.
Figure 6:
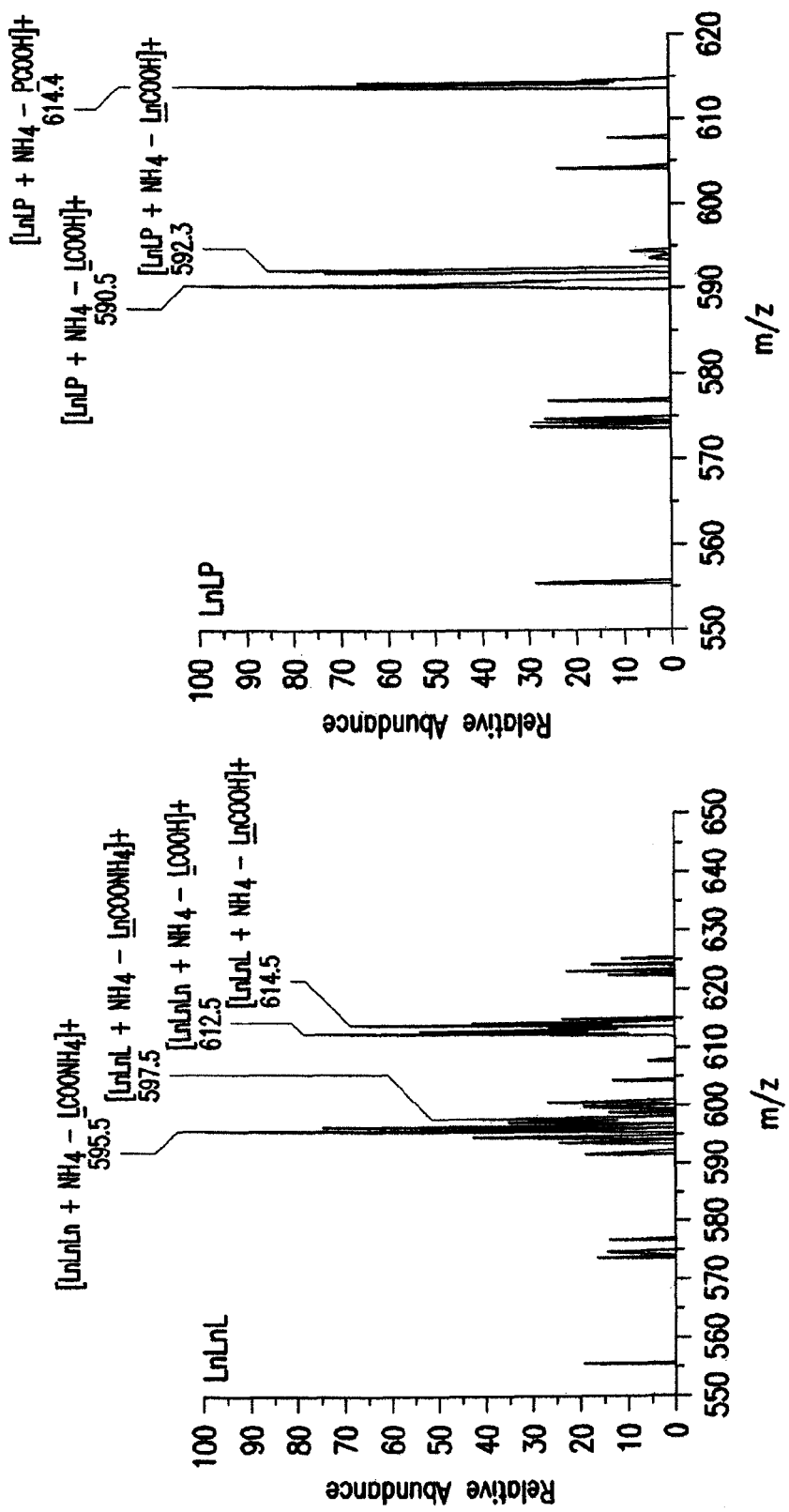
FIG. 6: Nanospray ionization and mass spectroscopy of triacylglycerol molecular species in *Arabidopsis*; tandem scans were typically carried out with an isolation width of 2.0 m/z, 35% normalized collision energy, 0.200 activation Q, and 30 msec activation time with a scan range from 200 to 1000 m/z. Representative tandem scans performed on the wild-type TAG extracts (FIG. 6) shows the typical diacylglycerol fragmentation products as notated by the TAG plus initial adduct [LnLnLn+NH4] minus a free fatty acid as underlined [LnLnLn+NH4-LnCOOH]+ and compared to known masses (Byrdwell, 2005).

Lipid bodies may be found in plant tissues other than seeds (e.g. see wild-type stems in FIG. 3 left). However, the elaboration of this compartment to the level seen in the cgi58 T-DNA knock out lines (FIG. 3) represents an unexpected result, and allows for use of non-seed, food or non-food vegetative biomass for plant oil production. Rough estimates of TAG content in the cgi58 T-DNA mutants suggests that the level of TAGs has increased by at least two to three times that of corresponding wild-type (FIG. 3 upper right). TAGs were identified and analyzed by nanospray ionization and mass spectrometry (see FIGS. 4-6).

Example 5

Further Enhancement of Oil Content in Plants Displaying a Cgi58 Mutant Phenotype Factors that might be combined with At4g24160 homolog loss-of-function mutations, or in other plants wherein At4g24160 is down-regulated, to increase the amount of oil accumulated in vegetative tissues such as leaf tissues may include the following: 1) ectopic expression of embryo-associated transcription factors that have been shown to result in oil accumulation in leaves (e.g, WRI1 or LEC; Cernac and Benning, 2003); 2) chemical or natural induction of senescence to stimulate lipid turnover (Guo and Gan, 2005) and boost accumulation of neutral lipid droplets in At4g24160-homolog mutant plants prior to harvest; 3) ectopic expression of oleosin proteins (Murphy, 1993; Capuano et al., 2003; Abell et al, 2004) to stabilize lipid droplets and prevent their turnover; or 4) combination of At4g24160 down-regulation with alterations in endoplasmic reticulum (ER) machinery to stimulate the abnormal accumulation of lipid droplets (Chapman et al., 2008).

Example 6

Identification of At4g24160 Homologs

Plant homologs of the *Arabidopsis* At4g24160 locus were initially found via in silico analysis of genomic and cDNA (e.g. EST) databases. Searches were conducted with the sequence of At4g24160 (SEQ ID NO:6 or SEQ ID NO:8), and multiple putative homologs were identified. FIG. 9 provides a nucleotide alignment of sequences encoding some homologs, sequences of which are given in SEQ ID NOs:18-36.

Example 7

Triacylglycerol Composition of Neutral Lipids Produced in Vegetative Tissues

The neutral lipid fractions from combined leaf tissues of mature plants (about 45 day old) were dissolved in 1:1 (v/v) chloroform:methanol with 10 mM ammonium acetate. TAG molecular species were identified by neutral loss fragmentation spectra in tandem. Typical scanning conditions were carried out in positive ion mode with a 4-4.5 kV spray voltage, scan range of 650 m/z to 950 m/z, 275° C. capillary temperature, 3 microscans per full scan with a maximum injection time of 200 msec. Tandem scans (MS/MS) were performed with an isolation width of 5.0 m/z, 35% normalized collision energy, and 30 msec activation time with a scan range from 200 m/z to 1000 m/z. Tripentadecanoyl glycerol (tri 15:0) was added at the time of extraction and used as a quantitative standard. All solvents were optima grade from Thermo-Fisher Scientific.

Figures 10A, 10B:
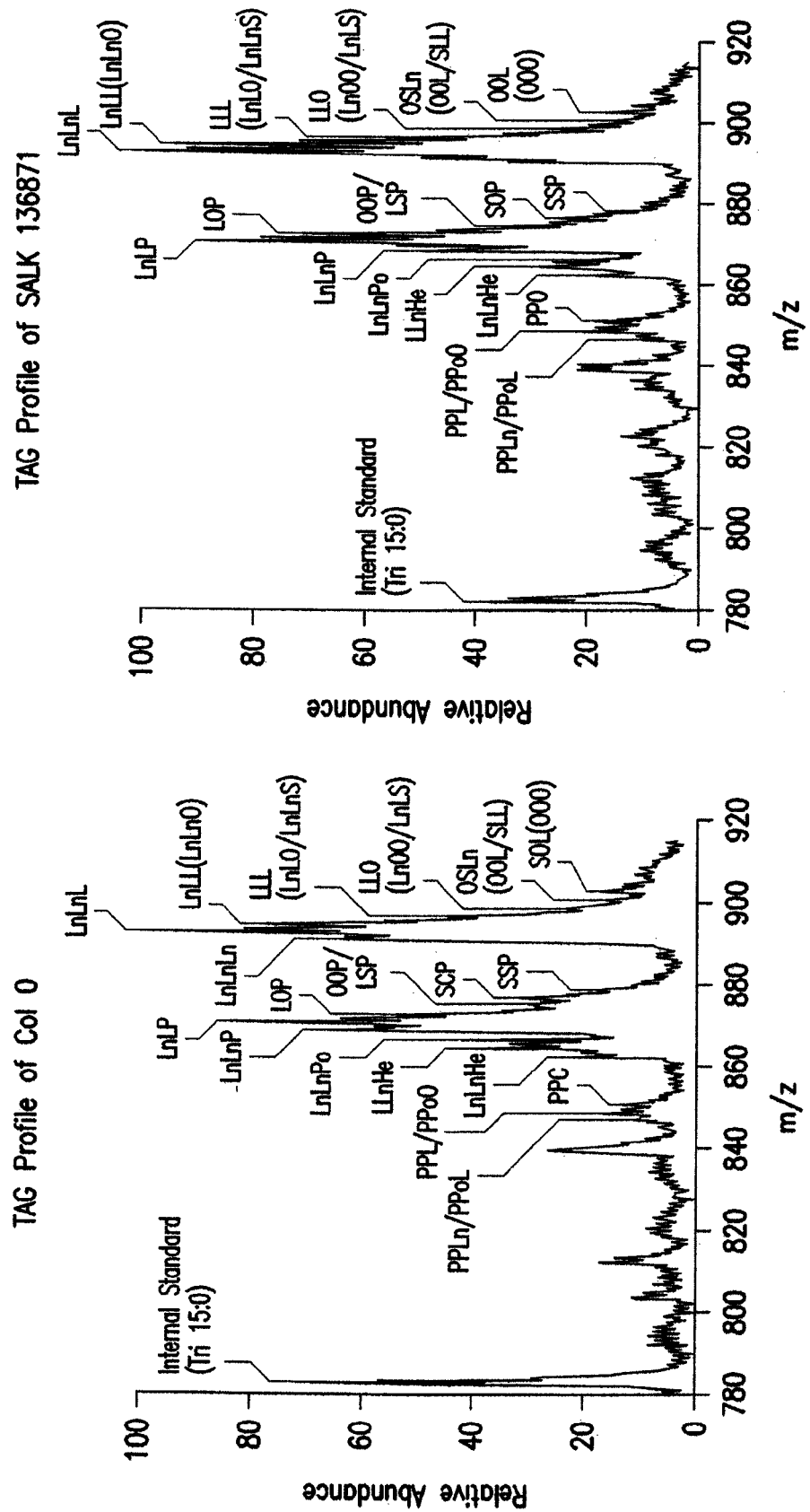
FIG. 10: Electrospray ionization mass spectrometry (MS) of TAG molecular species in wild-type and At4g24160 T-DNA knockout plants. Positive ion MS analysis of neutral lipids of wildtype (A) and CGI-58-exon disruption (B) identified TAG species as ammonium adducts [M++NH4]+ using a LCQ Deca XP Plus quadrupole ion trap. The neutral lipid fractions from combined leaf tissues of mature plants (about 45 d old) were dissolved in 1:1 (v/v) chloroform:methanol plus 10 mM ammonium acetate. Peaks are labeled according to the three fatty acids present in each TAG molecular species, and low abundance TAG species with the same molecular mass are indicated in parentheses. Positions of fatty acids on the glycerol backbone were not determined. Fatty acid abbreviations are: He, 16:3-hexadecatrienoic acid; L, 18:2-linoleic acid; Ln, α-18:3-linolenic acid; P, 16:0-palmitic acid; Po, 16:1-palmitoleic acid; 5, 18:0-stearic acid. (C) Regions of several relevant, representative MS/MS scans showing the diagnostic diacylglycerol fragmentation ions minus a free fatty acid compared to known masses (e.g. Byrdwell, 2005). Molecular ions were in some cases a combination of isomers as revealed in MS/MS (e.g., first two panels, each with three combinations of DAG species derived from same parent ion, but with a different fatty acid loss).
Figure 10C:
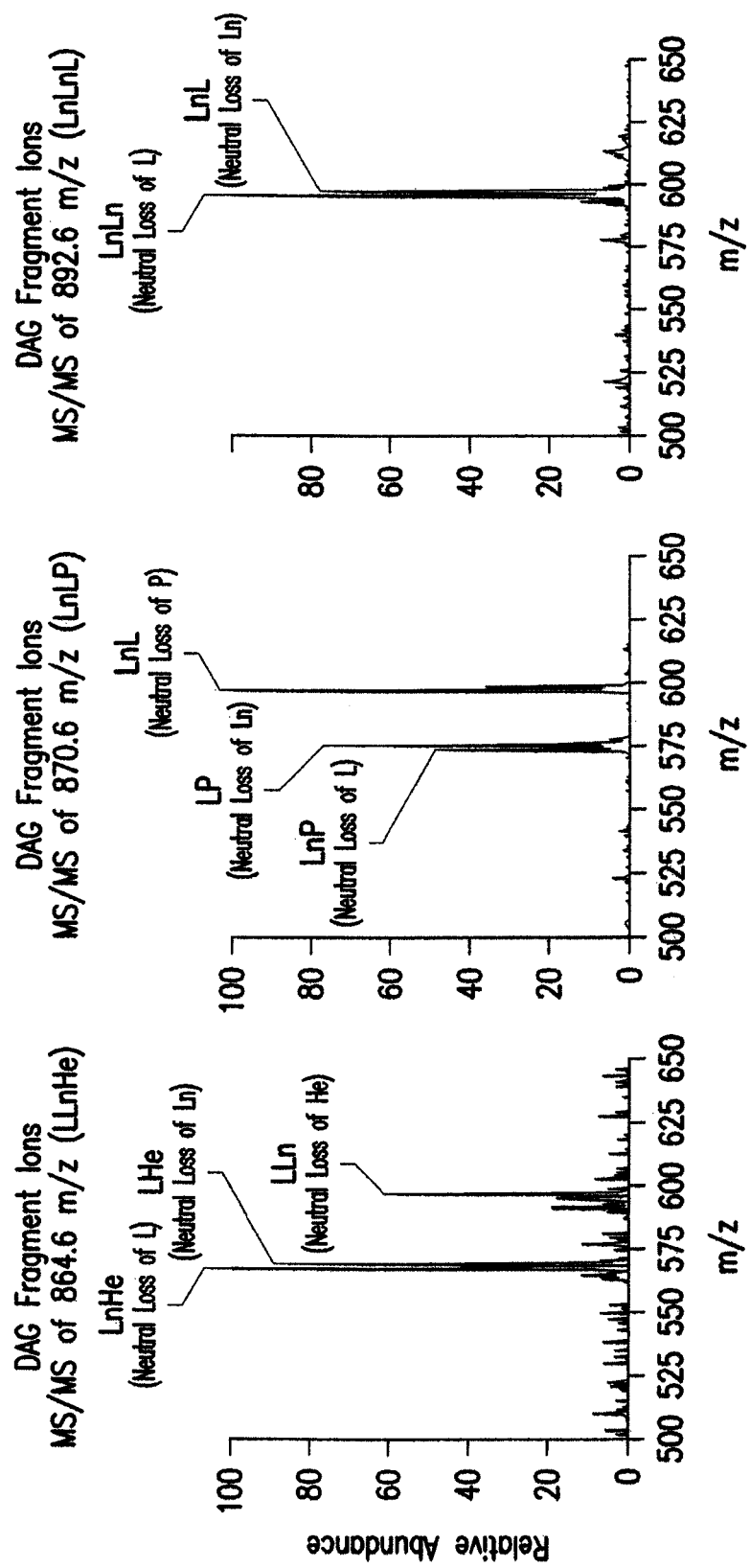

Previously, ectopic over-expression of seed transcription factors was shown to increase TAG content in *Arabidopsis* seedling tissues, and this appeared to be caused by an up-regulation of a seed-specific program (e.g. Cernac & Benning, 2004) because the TAG profiles were more similar to those found in seeds than in leaves. For instance, the TAGs in certain overexpression mutants were rich in 20:1/eicosaenoic fatty acid typically found in *Arabidopsis* seed oil bodies (Graham, 2008). In contrast, however, analysis of TAGs in above-ground vegetative tissues of cgi58 mutant plants by electrospray ionization and tandem mass (MS) unexpectedly showed that their molecular composition was similar to that found in wild-type leaves (see FIG. 10). That is, these TAGs were composed of typical leaf tissue fatty acids such as 16:3 and 18:3/hexadecatrienoic and octadecatrienoic fatty acids and did not contain 20:1 fatty acid. Moreover, the TAG profiles in the cgi58 mutants were reminiscent of the TAG composition generated in leaf tissues of a *Arabidopsis* beta-oxidation mutant (e.g. Yang & Ohlrogge, 2009). Thus, also in combination with genes encoding other fatty acid synthesis-related genes which are known in the art, the fatty acid composition (i.e. "profile"), as well as the level of neutral lipids, may be controlled in vegetative tissues of plants displaying a decreased level of At4g24160 function, to yield particular useful lipid species and profiles, including ones that are not otherwise found, or found at such levels, in seed oils.

Example 8

Quantification of Lipids in Vegetative Tissues

Figure 11C:
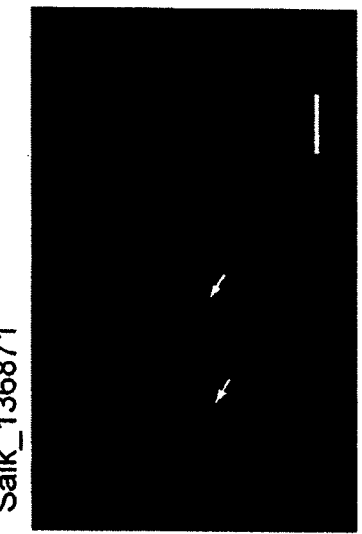
FIG. 11: shows that lipid droplets are abundant in leaves of cgi58 mutants. A) Representative confocal fluorescence micrograph of mesophyll tissues of mature wild-type leaves (about 40 d after emergence), showing chloroplasts and a few lipid droplets (arrows) stained with BODIPY 493. The boxed region in the left panel is shown at higher magnification on the right. (B) Confocal fluorescence micrograph of mesophyll tissues of same-age leaves of cgi-58 T-DNA knockouts showing similar chloroplast distribution, but with considerably more lipid droplets accumulated in the cytosol outside of chloroplasts. (C) Z-stack of thirteen optical sections (taken at 1 micron increments) of the cgi-58 T-DNA knockout mutant (Salk_136871), reconstructed to reveal the cellular organization of lipid droplets and their relationship to chloroplasts, as also seen in FIG. 8. D) The percent area of lipid droplets and chloroplasts in mesophyll cells was quantified by morphometric analysis as the percent of image area fluorescing from either the lipid droplets or chloroplasts channels. Averages and standard deviations are plotted for ten digital images of 25,000 microns$^2$ each taken from several leaves at each stage. There were significant differences between the amounts of lipid droplets in mutants and wild-types in leaves at 40 d ($p<0.0001$) and at 65 d ($p<0.002$), but not at 15 d ($p>0.63$). Abundance was most dramatic in mature, 40 d leaves. No statistical differences were observed in the relative percentage of chloroplasts between mutant and wild-type, suggesting the mutation only affected lipid accumulation in cytosolic droplets. Scale Bar=20 microns.
Figure 11D:
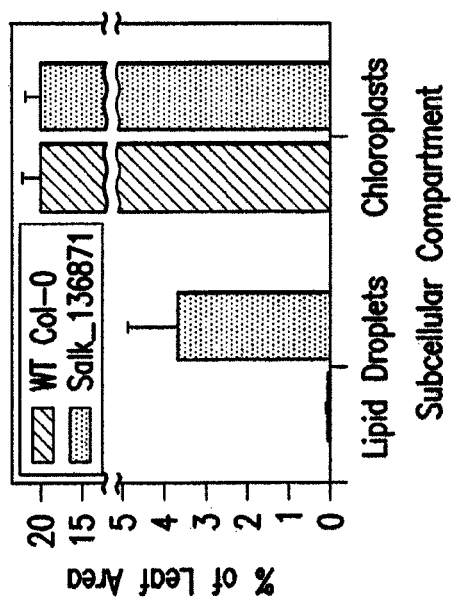
Figure 11A:
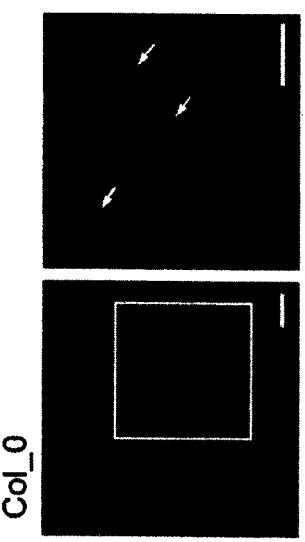
Figure 11B:
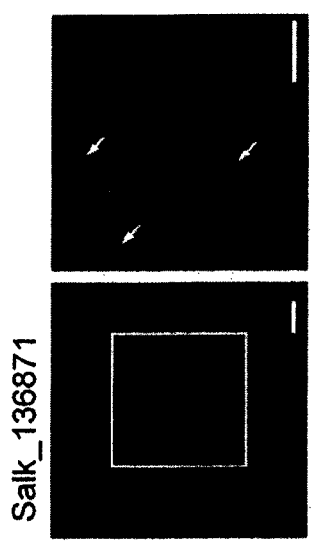

In addition to the studies described for instance in Example 4, additional imaging with a second neutral-lipid-specific stain (such as 4,4-difluoro-1,3,5,7,8-pentamethyl-4-bora-3a,4a-diaza-s-indacene (BODIPY®493); available from Molecular Probes-Invitrogen; Eugene, Oreg.), which has improved and more selective spectral characteristics (Tavian & Colombo, 2007) confirmed that there are more lipid droplets in mesophyll cells of mutant leaves compared to wild-type leaves (FIGS. 11A and B). Imaging both chloroplasts (red chlorophyll autofluorescence) and lipid droplets (green BODIPY 493 fluorescence, arrows) together in the mutants also showed that lipid droplets were extra-plastidial and that there appeared to be a dramatic elaboration of lipid droplets in mutants compared to wild-type leaf cells (FIGS. 11A and B). Moreover, three-dimensional reconstructions of multiple Z-stacked confocal images of mutants specifically revealed that the lipid droplets accumulated in the cytosol and not inside chloroplasts (FIG. 11C), which is unlike the lipid-rich plastoglobuli that tend to accumulate in the chloroplast stroma of stressed or senescing tissues (Munne-Bosch, 2005). Morphometric analysis comparing wild-type and mutant mesophyll tissues revealed a ~50-fold increase in area occupied by lipid droplets in mutant cells (quantified as % area in the green channel) compared to wild-type cells (3.71%±1.17 vs. 0.072%±0.040; $p<0.0001$), whereas the areas occupied by chloroplasts in these same groups of cells was approximately equivalent (quantified as % area in the red channel) (FIG. 11D). The amount of TAG in mature *Arabidopsis* cgi58 mutant plants quantified by direct electrospray MS against a tripentadecanoyl glycerol standard was 50% higher than in wild-type plants (e.g. 699±74 mg/g dw; vs 466±98 mg/g dw; n=9, $p<0.0001$).

Example 9

Developmental Aspects of Cytosolic Lipid Droplet Accumulation

Figure 12:
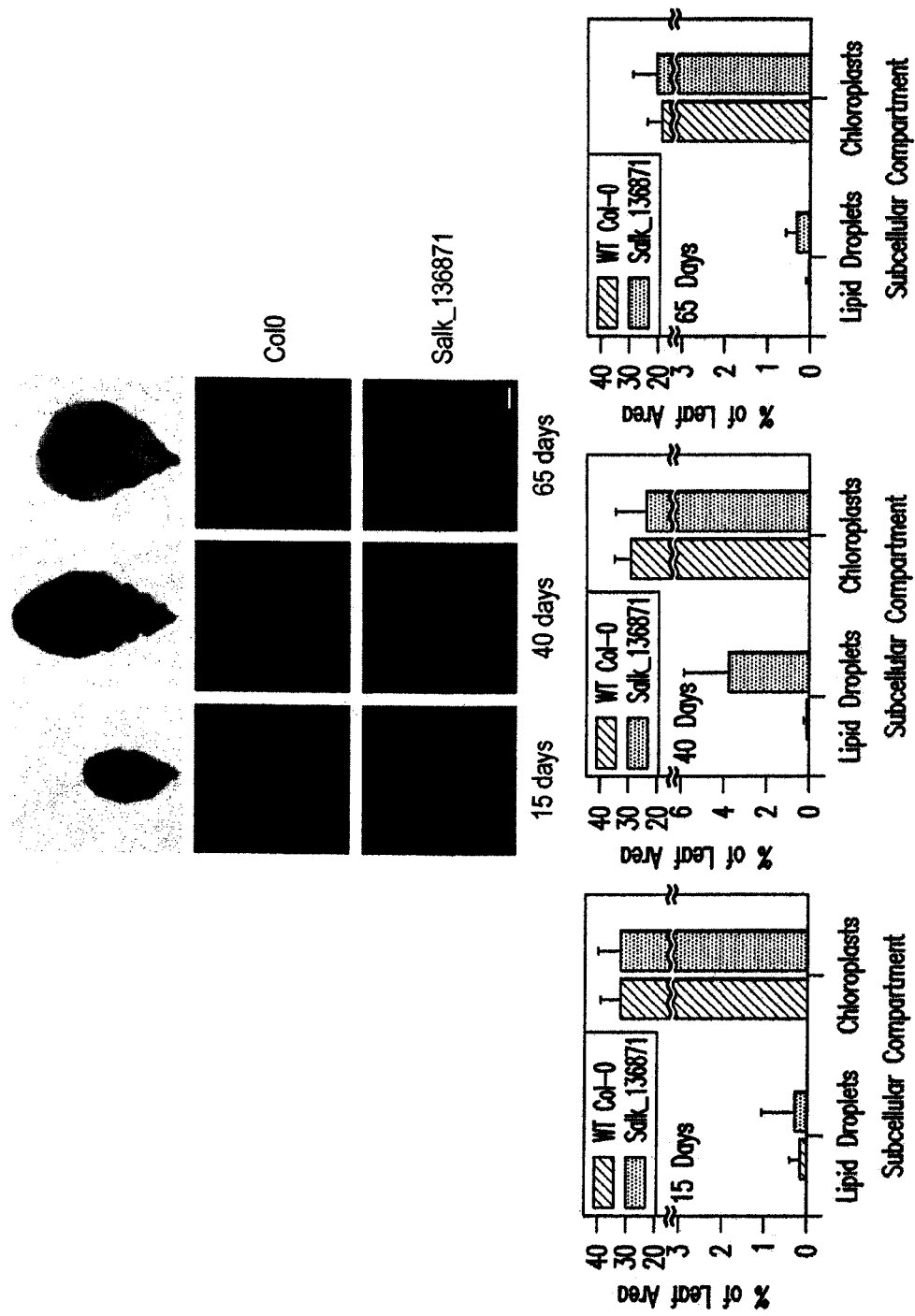
FIG. 12: shows temporal differences in lipid droplet accumulation in wild-type and cgi-58-disrupted *Arabidopsis* plant cells. Representative confocal fluorescence images of *Arabidopsis* leaves at 15 days after emergence, 40 d, or 65 d (WT and T-DNA mutant, Salk_136871). Lipid droplets are green and chloroplasts are red; imaging acquisition conditions were the same as for FIG. 11. Bar=20 microns.

A difference in cytosolic lipid droplet abundance was seen, depending upon the developmental stage of the leaves. That is, there were significantly more lipid droplets in mature, fully expanded leaves of the mutants (e.g., 40-day old), than either in younger leaves (15 days after emergence) or older, senescing leaves (65 days after emergence) of the mutants. Representative confocal fluorescence images of *Arabidopsis* leaves emerged at 15 d, 40 d, or 65 d (WT and T-DNA mutant, Salk_136871) are shown in FIG. 12. Lipid droplets are green and chloroplasts are red; imaging acquisition conditions were the same as for FIG. 11. The percent area of lipid droplets and chloroplasts (graphs in lower panel) were quantified as the percent of image area fluorescing from either the green or red channels, respectively. Averages and standard deviations are plotted from ten digital images of 25,000 microns$^2$ each over several leaves at each stage. There were significant differences between the amounts of lipid droplets in mutants and wild-type leaves at 40 days ($p<0.0001$) and at 65 days ($p<0.002$), but not at 15 days ($p>0.63$). Abundant droplets were most evident in mature, 40 day-old leaves of mutants. No statistical differences were observed in the relative percentage of chloroplasts between mutant and wild-type leaves, suggesting the mutation affected lipid accumulation in cytosolic droplets, not lipid biosynthesis which primarily occurs in chloroplasts.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references are incorporated herein by reference:

U.S. Pat. No. 4,536,475; U.S. Pat. No. 5,416,011; U.S. Pat. No. 5,463,174; U.S. Pat. No. 5,591,616; U.S. Pat. No. 5,731,179; U.S. Pat. No. 5,959,179; U.S. Pat. No. 6,037,527; U.S. Pat. No. 6,153,812; U.S. Pat. No. 6,160,208.
Abell et al., *Plant J.* 37:461-470, 2004.
Adams et al., *JAOCS* 105:661, 1983.
Beach et al., *EMBO J.* 4:3047, 1985.
Bevan et al., *NAR* 11:369-385, 1983.
Broothaerts et al., *Nature,* 433:629-633, 2005.
Bruno et al., *Biochem. Biophys. Res. Commun.* 369:1125-1128, 2008.
Byrdwell, "Modern Methods for lipid analysis by liquid chromatography: Mass spectrometry and related techniques" 1$^{st}$ ed. Taylor & Francis, 2005.
Capuano et al., *Biotechnol. Adv.* 25:203-206, 2007.
Carruthers et al., *Cold Spring Harbor Symp. Quant. Biol.* 47:411-418, 1982.
Cernac & Benning, *Plant J.* 40:575-585, 2004.
Chandler et al., *Plant Cell* 1:1175, 1989.
Chapman and Trelease, *J. Cell Biol.* 115:995-1007, 1991.
Chapman et al., *Crop Science* 48:1470-1481, 2008.
Christou et al., "Particle Bombardment for Genetic Engineering of Plants" pp. 50-60 (rice), pp. 63-69 (maize), Biotechnology Intelligence Unit, Academic Press, San Diego, Calif., 1996.
Ebert et al., *PNAS* 84:5745, 1987.
Elbashir et al., *Genes & Devel.,* 15:188-200 2001.
Evans et al., "Protoplast Isolation and Culture" pp. 124-176 in Handbook of Plant Cell Culture, MacMillan, New York, 1983.
Finnlayson et al., *Arch. Biochem. Biophys.,* 199:179-185, 1980.
Fraley et al., *PNAS* 80:4803, 1983.
Fromm et al., *PNAS* 82:5824, 1985.

Fuentes and Taliaferro, "Biomass yield stability of switchgrass cultivars." p. 276-282. In: Janick and Whipkey (eds.), Trends in new crops and new uses. ASHS Press, Alexandria, Va., 2002.
Ghosh et al., *J. Biol. Chem.* 283:24525-24533, 2008.
Graham, *Ann. Rev. Pl. Biol.* 59:115-142, 2008.
Guo & Gan, *Curr. Top. Dev. Biol.* 71:83-112, 2005.
Hamilton et al., *Pl. Physiol.* 18:223-229, 1999.
Hamilton and Baulcombe, *Science,* 286:950-952, 1999.
Heath and Rock, *J. Bacteriol.* 180:1425-1430, 1998.
Horsch et al., *Science* 233:496-498, 1984.
Hudspeth et al., *Plant Mol. Biol.* 12:579, 1989.
Innis et al., eds. "*PCR Protocols: A Guide to Methods and Applications*," Academic Press, San Diego, 1990.
Kay et al., *Science* 235:1299-1302, 1987.
Kridl et al., *Seed Sci. Res.* 1:209-219, 1991.
Kennedy et al., *J. Biol. Chem.,* 222:193, 1956.
Klein et al., *Nature* 327:70-73, 1987.
Lass et al., *Cell Metab.* 3:309-319, 2006.
Lawton et al., *Plant Mol. Biol.* 9:31F, 1987.
Lefèvre et al., *Am. J. Hum. Genet.* 69:1002-1012, 2001.
Lu & Mathews, *NAR* 36:W104-W108, 2008.
McCallum et al., *Pl. Physiol.* 123:439-442, 2000.
Munne-Bosch, *J. Pl. Physiol.* 162:743-748, 2005.
Murphy, *Prog. Lipid Res.* 32:247-280, 1993.
Murphy, *Prog. Lipid Res.* 40:325-438, 2001.
Odell et al., *Nature* 313:810-812, 1985.
Paszkowski et al., *EMBO J.* 3:2717-2722, 1984.
Quackenbush et al., *NAR* 29:159-164, 2001.
Reynolds, *Nature* 22:326-330, 2004.
Sambrook et al., (ed.), *Molecular Cloning*, Cold Spring Harbor Laboratory Press, Cold Spring Harbor, N.Y., 1989.
Schweiger et al., *J. Biol. Chem.* 281:40236-40241, 2006.
Schrag and Cygler, *Meth. Enzymol.* 284:85-107, 1997.
Stockhaus et al., *EMBO J.* 8:2445-2451, 1989.
Stormo, *Genome Res.* 10:394-397, 2000.
Sullivan et al., *Mol. Gen. Genet.* 215:431, 1989.
Tavian & Colombo, *J. Clin. Pathol.* 60:956-958, 2007.
Walker et al., *PNAS* 845:6624, 1987.
Wang et al., *Mol. Cell. Biol.* 12:3399, 1992.
Weising et al., *Anna Rev. Genet.* 22:421-477, 1988.
Wilmink & Dons, *Pl. Mol. Biol. Rep.* 11:165-185, 1993.
WO 84/02913;
Yamaguchi et al., *J. Lipid Res.* 48:1078-1089, 2007.
Yang et al., *PNAS* 87:4144, 1990.
Yang & Ohlrogge, *Pl. Physiol.* 150:1981-1989, 2009.
Yen & Farese, *Cell Metab.* 3:305-307, 2006.

What is claimed is:

1. A plant comprising increased lipid accumulation in vegetative tissues relative to a wild type plant of the same species and wherein activity of a CGI58 homolog is down-regulated in the plant, wherein down-regulation of a CGI58 homolog comprises at least one method selected from the group consisting of:
   a) expressing in the plant a RNA molecule complementary to all or a portion of an mRNA expressed from a gene comprising the sequence selected from the group consisting of SEQ ID NOs:18-36, wherein the RNA molecule inhibits the function of the CGI58 homolog in said plant;
   b) mutagenizing said CGI58 homolog so that the function thereof is down-regulated relative to wild type CGI58 homolog in a plant of the same species; and
   c) co-suppression;
   wherein the plant is of a species selected from the group consisting of corn, sugarcane, sorghum, millet, rice, wheat, barley, soybean, *Glycine* sp., grape, canola, *Brassica* sp., cotton, tobacco, sugar beet, sunflower, bamboo, switchgrass (*Panicum virgatum*), giant reed (*Arundo donax*), reed canarygrass (*Phalaris arundinacea*), *Miscanthus×giganteus, Miscanthus* sp., *Sericea lespedeza* (*Lespedeza cuneata*), ryegrass (*Lolium multiflorum, Lolium* sp.), timothy, kochia (*Kochia scoparia*), forage soybeans, alfalfa, clover, turf grass, sunn hemp, kenaf, bahiagrass, bermudagrass, dallisgrass, pangolagrass, big bluestem, indiangrass, fescue (*Festuca* sp.) including tall fescue, *Dactylis* sp., *Brachypodium distachyon*, smooth bromegrass, orchardgrass, kentucky bluegrass, yellow nutsedge (*Cyperus esculentus*), pine, poplar (*Populus* sp.), willow, and eucalyptus.

2. The plant of claim 1, wherein the plant is a transgenic plant.

3. The plant of claim 1, wherein the plant is non-transgenic.

4. The plant of claim 2, further defined as a fertile $R_0$ transgenic plant.

5. The plant of claim 2, further defined as a progeny plant of any generation of a fertile $R_0$ transgenic plant.

6. A seed of the plant of claim 1, wherein the seed is of a plant that comprises increased lipid accumulation in vegetative tissues relative to a wild type plant of the same species and wherein the CGI58 homolog is down-regulated in the seed, and wherein the seed comprises a polynucleotide encoding the RNA molecule, the mutagenized CGI58 homolog gene, or co-suppression.

7. A plant part of the plant of claim 1, comprising a polynucleotide encoding the RNA molecule, the mutagenized CGI58 homolog gene, or co-suppression.

8. The plant part of claim 7, selected from the group consisting of a cell, a leaf, a stem, a petiole, pollen, a tuber, and root tissue.

9. A method of altering lipid content in a plant or plant cell comprising down-regulating the function of a CGI58 homolog gene product, wherein down-regulating comprises expressing a RNA molecule that inhibits the function of the CGI58 homolog gene product in said plant or plant cell; mutagenizing said CGI58 homolog gene; or co-suppression, and
   wherein the plant or plant cell is of a species selected from the group consisting of corn, sugarcane, sorghum, millet, rice, wheat, barley, soybean, *Glycine* sp., grape, canola, *Brassica* sp., cotton, tobacco, sugar beet, sunflower, bamboo, switchgrass (*Panicum virgatum*), giant reed (*Arundo donax*), reed canarygrass (*Phalaris arundinacea*), *Miscanthus×giganteus, Miscanthus* sp., *Sericea lespedeza* (*Lespedeza cuneata*), ryegrass (*Lolium multiflorum, Lolium* sp.), timothy, kochia (*Kochia scoparia*), forage soybeans, alfalfa, clover, turf grass, sunn hemp, kenaf, bahiagrass, bermudagrass, dallisgrass, pangolagrass, big bluestem, indiangrass, fescue (*Festuca* sp.) including tall fescue, *Dactylis* sp., *Brachypodium distachyon*, smooth bromegrass, orchardgrass, kentucky bluegrass, yellow nutsedge (*Cyperus esculentus*), pine, poplar (*Populus* sp.), willow, and eucalyptus.

10. The method of claim 9, wherein the sequence of the homolog, or the gene encoding the homolog, comprises the sequence selected from the group consisting of: SEQ ID NOs:18-36; and a sequence at least 90% identical to the sequence selected from the group consisting of SEQ ID NOs: 18-36.

11. The method of claim 9, wherein down-regulating the function of a CGI58 homolog gene product comprises eliminating the function of said CGI58 homolog gene product, wherein the sequence of the homolog comprises the sequence selected from the group consisting of: SEQ ID NOs:18-36; and a sequence at least-90% identical to the sequence selected from the group consisting of SEQ ID NOs:18-36.

12. The method of claim 9, wherein down-regulating the function of a CGI58 homolog gene product comprises expressing in the plant a RNA molecule complementary to all or a portion of an mRNA expressed from a gene comprising the sequence selected from the group consisting of SEQ ID NOs:18-36, wherein the RNA molecule inhibits the function of a CGI58 homolog gene product in said plant.

13. The method of claim 12, wherein the RNA molecule is a single stranded RNA molecule.

14. The method of claim 12, wherein the RNA molecule is a double stranded RNA molecule.

15. The method of claim 9, wherein down-regulating the function of a CGI58 homolog gene product comprises mutagenizing said CGI58 homolog gene so that the function thereof is down-regulated relative to the wild type CGI58 homolog in a plant of the same species.

16. The method of claim 9, wherein down-regulating the function of a CGI58 homolog gene product comprises co-suppression.

17. A method of producing lipids in a plant comprising:
(a) obtaining a plant according to claim 1; and
(b) isolating lipid from said plant.

18. A method of breeding a plant having increased lipid accumulation in vegetative tissues comprising: identifying a plant comprising a reduced level of function of a CGI58 homolog gene product relative to that found in an otherwise isogenic plant that displays a wild-type level of function of a CGI58 homolog gene product; selecting the plant for crossing with a second plant; and crossing the first plant with a second plant of the same species or variety to produce a progeny plant comprising a reduced level of function of a CGI158 homolog gene product; wherein the plant is of a species selected from the group consisting of corn, sugarcane, sorghum, millet, rice, wheat, barley, soybean, *Glycine* sp., grape, canola, *Brassica* sp., cotton, tobacco, sugar beet, sunflower, bamboo, switchgrass (*Panicum virgatum*), giant reed (*Arundo donax*), reed canarygrass (*Phalaris arundinacea*), Miscanthus×giganteus, Miscanthus sp., *Sericea lespedeza* (*Lespedeza cuneata*), ryegrass (*Lolium multiflorum, Lolium* sp.), timothy, kochia (*Kochia scoparia*), forage soybeans, alfalfa, clover, turf grass, sunn hemp, kenaf, bahiagrass, bermudagrass, dallisgrass, pangolagrass, big bluestem, indiangrass, fescue (*Festuca* sp) including tall fescue, *Dactylis* sp., *Brachypodium distachyon*, smooth bromegrass, orchardgrass, kentucky bluegrass, yellow nutsedge (*Cyperus esculentus*), pine, poplar (*Populus* sp.), willow, and eucalyptus.

19. The method of claim 18, wherein the step of identifying comprises at least one method selected from the group consisting of: PCR, single strand conformational polymorphism analysis, denaturing gradient gel electrophoresis, cleavage fragment length polymorphism analysis and/or DNA sequencing.

20. The method of claim 18, wherein the reduced level of function of a CGI58 homolog gene is conferred by a polymorphism comprising an insertion, a deletion, or at least one single nucleotide polymorphism (SNP) at a position in the CGI58 homolog locus that reduces the function of the CGI58 homolog relative to that found in an otherwise isogenic plant displaying a wild-type level of function of the CGI58 homolog gene product.

21. A method of producing food, feed, or oil comprising:
(a) obtaining the plant of claim 1;
(b) cultivating said plant to obtain a plant product; and
(c) preparing food, feed, or oil from said plant or plant product.

22. The method of claim 21, wherein the oil comprises TAG.

23. The method of claim 21, wherein the neutral lipids isolated from vegetative tissues of the plant comprise a rationally designed fatty acid profile.

24. The method of claim 23, wherein the neutral lipids comprise hydroxyl, epoxy, cyclic, acetylenic, saturated, polyunsaturated, short-chain fatty acids, long-chain fatty acids, TAGs, wax-esters, or steryl-esters.

25. The method of claim 21, wherein the neutral lipids isolated from vegetative tissues of the plant comprise a leaf-specific fatty acid profile.

26. The method of claim 25, wherein the neutral lipids isolated from vegetative tissues of the plant comprise hexadecatrienoic and octadecatetraenoic fatty acids, or do not contain eicosaenoic fatty acid.

* * * * *

SEQUENCE LISTING

```
<160> NUMBER OF SEQ ID NOS: 41

<210> SEQ ID NO 1
<211> LENGTH: 5
<212> TYPE: PRT
<213> ORGANISM: Artificial
<220> FEATURE:
<223> OTHER INFORMATION: Consensus sequence
<220> FEATURE:
<221> NAME/KEY: MISC_FEATURE
<223> OTHER INFORMATION: X = any amino acid
<220> FEATURE:
<221> NAME/KEY: MISC_FEATURE
<222> LOCATION: (2)..(4)
<223> OTHER INFORMATION: X = any amino acid

<400> SEQUENCE: 1

Gly Xaa Ser Xaa Gly
1               5

<210> SEQ ID NO 2
<211> LENGTH: 50
<212> TYPE: PRT
<213> ORGANISM: Artificial
<220> FEATURE:
<223> OTHER INFORMATION: Consensus sequence

<400> SEQUENCE: 2

Ile Asp Ser Ile Glu Glu Trp Arg Cys Ala Lys Asn Leu Asp Asn Met
1               5                   10                  15

Ile Leu Leu Gly His Asn Phe Gly Gly Tyr Val Ala Ala Lys Tyr Ala
            20                  25                  30

Leu Lys Tyr Pro Glu His Val Gln His Leu Ile Leu Val Gly Pro Trp
        35                  40                  45

Gly Phe
    50

<210> SEQ ID NO 3
<211> LENGTH: 29
<212> TYPE: PRT
```

```
<213> ORGANISM: Artificial Sequence
<220> FEATURE:
<223> OTHER INFORMATION: Consensus sequence

<400> SEQUENCE: 3

Met Glu Glu Asp Lys Leu Val Thr Asp Tyr Ile Tyr His Cys Asn Ala
1               5                   10                  15

Gln Lys Pro Ser Gly Glu Leu Cys Phe Lys Tyr Met Phe
            20                  25

<210> SEQ ID NO 4
<211> LENGTH: 21
<212> TYPE: PRT
<213> ORGANISM: Artificial sequence
<220> FEATURE:
<223> OTHER INFORMATION: Consensus sequence

<400> SEQUENCE: 4

Arg Val Tyr Ala Ile Asp Gln Leu Gly Trp Gly Gly Ser Ser Arg Pro
1               5                   10                  15

Asp Phe Thr Cys Asp
            20

<210> SEQ ID NO 5
<211> LENGTH: 19
<212> TYPE: PRT
<213> ORGANISM: Artificial Sequence
<220> FEATURE:
<223> OTHER INFORMATION: Consensus sequence

<400> SEQUENCE: 5

Phe Thr Pro Gln Lys Leu Val Arg Gly Leu Gly Pro Trp Gly Pro Gly
1               5                   10                  15

Leu Val Asn

<210> SEQ ID NO 6
<211> LENGTH: 1257
<212> TYPE: DNA
<213> ORGANISM: Arabidopsis thaliana

<400> SEQUENCE: 6
atgaacttga gccgttttgc ttcgagatta agaatggcgg aagaaatctc aaagacgaag      60
gtgggatctt cttctactgc ttcggtggct gattcatctg ctgctgcgtc ggctgcaacg     120
aatgcggcca atcaagatg gaaaattttg tggcctaatt cgctccggtg gattcctacg      180
tccaccgatt acatcatcgc cgccgagaaa cgtcttctct ccatcctcaa gacgccttat     240
gtacaagagc aagtcagtat tggttcagga ccaccaggtt ctaaaatcag gtggtttagg     300
tctacgagca atgagtcacg ttacatcaac actgttacat tgatgccaa ggagggagct      360
cctacactcg tcatggttca tggttatggt gcttctcaag gttttttctt ccgtaatttt     420
gatgctcttg ccagtcgatt tagagtgatc gctattgatc aacttgggtg gggtggttca     480
agtaggcctg attttacatg tagaagcaca gaagaaactg aggcatggtt tatcgactcc     540
tttgaggaat ggcgtaaagc ccagaatctc agtaacttta ttctattagg acattctttt     600
ggaggctatg ttgctgctaa atacgcgctt aagcatcctg aacatgttca acacttaatt     660
ctggtgggat ctgctgggtt ctcagcagaa gcagatgcca atcagaatg gctcactaaa      720
tttagagcaa catggaaagg tgcagtccta aatcatttat gggagtcaaa tttcactcct     780
cagaagctgg ttagaggatt aggtccttgg ggtccaggtc ttgtaaatcg gtatacaact     840
```

```
gcaagatttg gtgcacattc ggagggaact gggctaacag aagaggaagc caaattgcta    900
accgattatg tgtaccatac tttggctgca aaggctagtg gagagttatg cttgaaatac    960
atcttctcat ttggagcatt tgctaggaag cccctcttac aaagtgcatc agagtggaaa   1020
gtgccaacaa cgtttatcta tggaatgaat gattggatga actatcaagg tgcggtggaa   1080
gcgaggaaat ccatgaaggt cccttgcgaa atcattcggg ttccacaggg tggtcatttt   1140
gtgttcatag acaacccaat tggttttcat tctgcagtgc tttatgcttg ccgcaagttt   1200
atatctcaag actcctctca tgatcaacaa ctcctagatg gtctacgatt ggtttag     1257
```

<210> SEQ ID NO 7
<211> LENGTH: 418
<212> TYPE: PRT
<213> ORGANISM: Arabidopsis thaliana

<400> SEQUENCE: 7

```
Met Asn Leu Ser Arg Phe Ala Ser Arg Leu Arg Met Ala Glu Glu Ile
1               5                   10                  15

Ser Lys Thr Lys Val Gly Ser Ser Thr Ala Ser Val Ala Asp Ser
            20                  25                  30

Ser Ala Ala Ser Ala Ala Thr Asn Ala Ala Lys Ser Arg Trp Lys
        35                  40                  45

Ile Leu Trp Pro Asn Ser Leu Arg Trp Ile Pro Thr Ser Thr Asp Tyr
    50                  55                  60

Ile Ile Ala Ala Glu Lys Arg Leu Leu Ser Ile Leu Lys Thr Pro Tyr
65                  70                  75                  80

Val Gln Glu Gln Val Ser Ile Gly Ser Gly Pro Pro Gly Ser Lys Ile
                85                  90                  95

Arg Trp Phe Arg Ser Thr Ser Asn Glu Ser Arg Tyr Ile Asn Thr Val
            100                 105                 110

Thr Phe Asp Ala Lys Glu Gly Ala Pro Thr Leu Val Met Val His Gly
        115                 120                 125

Tyr Gly Ala Ser Gln Gly Phe Phe Arg Asn Phe Asp Ala Leu Ala
    130                 135                 140

Ser Arg Phe Arg Val Ile Ala Ile Asp Gln Leu Gly Trp Gly Gly Ser
145                 150                 155                 160

Ser Arg Pro Asp Phe Thr Cys Arg Ser Thr Glu Glu Thr Glu Ala Trp
                165                 170                 175

Phe Ile Asp Ser Phe Glu Glu Trp Arg Lys Ala Gln Asn Leu Ser Asn
            180                 185                 190

Phe Ile Leu Leu Gly His Ser Phe Gly Gly Tyr Val Ala Ala Lys Tyr
        195                 200                 205

Ala Leu Lys His Pro Glu His Val Gln His Leu Ile Leu Val Gly Ser
    210                 215                 220

Ala Gly Phe Ser Ala Glu Ala Asp Ala Lys Ser Glu Trp Leu Thr Lys
225                 230                 235                 240

Phe Arg Ala Thr Trp Lys Gly Ala Val Leu Asn His Leu Trp Glu Ser
                245                 250                 255

Asn Phe Thr Pro Gln Lys Leu Val Arg Gly Leu Gly Pro Trp Gly Pro
            260                 265                 270

Gly Leu Val Asn Arg Tyr Thr Thr Ala Arg Phe Gly Ala His Ser Glu
        275                 280                 285

Gly Thr Gly Leu Thr Glu Glu Ala Lys Leu Leu Thr Asp Tyr Val
    290                 295                 300
```

```
Tyr His Thr Leu Ala Ala Lys Ala Ser Gly Glu Leu Cys Leu Lys Tyr
305                 310                 315                 320

Ile Phe Ser Phe Gly Ala Phe Ala Arg Lys Pro Leu Leu Gln Ser Ala
                325                 330                 335

Ser Glu Trp Lys Val Pro Thr Thr Phe Ile Tyr Gly Met Asn Asp Trp
            340                 345                 350

Met Asn Tyr Gln Gly Ala Val Glu Ala Arg Lys Ser Met Lys Val Pro
        355                 360                 365

Cys Glu Ile Ile Arg Val Pro Gln Gly Gly His Phe Val Phe Ile Asp
    370                 375                 380

Asn Pro Ile Gly Phe His Ser Ala Val Leu Tyr Ala Cys Arg Lys Phe
385                 390                 395                 400

Ile Ser Gln Asp Ser Ser His Asp Gln Gln Leu Leu Asp Gly Leu Arg
                405                 410                 415

Leu Val

<210> SEQ ID NO 8
<211> LENGTH: 1443
<212> TYPE: DNA
<213> ORGANISM: Arabidopsis thaliana

<400> SEQUENCE: 8
agtagcaaac ttctcgattc cttgattcgt gggaaaaaga aagtctagat ttttgtggat      60
tttgattttg tgattccgtg attgtatgaa cttgagccgt tttgcttcga gattaagaat     120
ggcggaagaa atctcaaaga cgaaggtggg atcttcttct actgcttcgg tggctgattc     180
atctgctgct gcgtcggctg caacgaatgc ggccaaatca agatggaaaa ttttgtggcc     240
taattcgctc cggtggattc ctacgtccac cgattacatc atcgccgccg agaaacgtct     300
tctctccatc ctcaagacgc cttatgtaca agagcaagtc agtattggtt caggaccacc     360
aggttctaaa atcaggtggt ttaggtctac gagcaatgag tcacgttaca tcaacactgt     420
tacatttgat gccaaggagg gagctcctac actcgtcatg gttcatggtt atggtgcttc     480
tcaagggttt ttcttccgta attttgatgc tcttgccagt cgatttagag tgatcgctat     540
tgatcaactt gggtgggtg gttcaagtag gcctgatttt acatgtagaa gcacagaaga     600
aactgaggca tggtttatcg actcctttga ggaatggcgt aaagcccaga atctcagtaa     660
ctttattcta ttaggacatt cttttggagg ctatgttgct gctaaatacg cgcttaagca     720
tcctgaacat gttcaacact taattctggt gggatctgct gggttctcag cagaagcaga     780
tgccaaatca gaatggctca ctaaatttag agcaacatgg aaaggtgcag tcctaaatca     840
tttatgggag tcaaatttca ctcctcagaa gctggttaga ggattaggtc cttggggtcc     900
aggtcttgta atcggtata caactgcaag atttggtgca cattcggagg gaactgggct     960
aacagaagag gaagccaaat tgctaaccga ttatgtgtac catactttgg ctgcaaaggc    1020
tagtggagag ttatgcttga atacatctt ctcatttgga gcatttgcta ggaagccct    1080 cttacaaagt gcatcagagt ggaaagtgcc aacaacgttt atctatggaa tgaatgattg    1140
gatgaactat caaggtgcgg tggaagcgag gaaatccatg aaggtccctt gcgaaatcat    1200
tcgggttcca cagggtggtc attttgtgtt catagacaac ccaattggtt ttcattctgc    1260
agtgctttat gcttgccgca gtttatatc tcaagactcc tctcatgatc aacaactcct    1320
agatggtcta cgattggttt agtcatagta tcttgttcct tttaccttcc aaatttattc    1380
tatatgtgta tacaagtata tatgaaaaag aacataaaaa agaattactt tctttatttg    1440
```

```
aat                                                                    1443
```

<210> SEQ ID NO 9
<211> LENGTH: 217
<212> TYPE: PRT
<213> ORGANISM: Arabidopsis thaliana

<400> SEQUENCE: 9

| Val | His | Gly | Tyr | Gly | Ala | Ser | Gln | Gly | Phe | Phe | Arg | Asn | Phe | Asp |
|---|---|---|---|---|---|---|---|---|---|---|---|---|---|---|
| 1 | | | | 5 | | | | | 10 | | | | | 15 |

| Ala | Leu | Ala | Ser | Arg | Phe | Arg | Val | Ile | Ala | Ile | Asp | Gln | Leu | Gly | Trp |
|---|---|---|---|---|---|---|---|---|---|---|---|---|---|---|---|
| | | | 20 | | | | | 25 | | | | | 30 | | |

| Gly | Gly | Ser | Ser | Arg | Pro | Asp | Phe | Thr | Cys | Arg | Ser | Thr | Glu | Glu | Thr |
|---|---|---|---|---|---|---|---|---|---|---|---|---|---|---|---|
| | | | 35 | | | | | 40 | | | | | 45 | | |

| Glu | Ala | Trp | Phe | Ile | Asp | Ser | Phe | Glu | Glu | Trp | Arg | Lys | Ala | Gln | Asn |
|---|---|---|---|---|---|---|---|---|---|---|---|---|---|---|---|
| | 50 | | | | | 55 | | | | | 60 | | | | |

| Leu | Ser | Asn | Phe | Ile | Leu | Leu | Gly | His | Ser | Phe | Gly | Gly | Tyr | Val | Ala |
|---|---|---|---|---|---|---|---|---|---|---|---|---|---|---|---|
| 65 | | | | | 70 | | | | | 75 | | | | | 80 |

| Ala | Lys | Tyr | Ala | Leu | Lys | His | Pro | Glu | His | Val | Gln | His | Leu | Ile | Leu |
|---|---|---|---|---|---|---|---|---|---|---|---|---|---|---|---|
| | | | | 85 | | | | | 90 | | | | | 95 | |

| Val | Gly | Ser | Ala | Gly | Phe | Ser | Ala | Glu | Ala | Asp | Ala | Lys | Ser | Glu | Trp |
|---|---|---|---|---|---|---|---|---|---|---|---|---|---|---|---|
| | | | | 100 | | | | | 105 | | | | | 110 | |

| Leu | Thr | Lys | Phe | Arg | Ala | Thr | Trp | Lys | Gly | Ala | Val | Leu | Asn | His | Leu |
|---|---|---|---|---|---|---|---|---|---|---|---|---|---|---|---|
| | | | 115 | | | | | 120 | | | | | 125 | | |

| Trp | Glu | Ser | Asn | Phe | Thr | Pro | Gln | Lys | Leu | Val | Arg | Gly | Leu | Gly | Pro |
|---|---|---|---|---|---|---|---|---|---|---|---|---|---|---|---|
| | 130 | | | | | 135 | | | | | 140 | | | | |

| Trp | Gly | Pro | Gly | Leu | Val | Asn | Arg | Tyr | Thr | Thr | Ala | Arg | Phe | Gly | Ala |
|---|---|---|---|---|---|---|---|---|---|---|---|---|---|---|---|
| 145 | | | | | 150 | | | | | 155 | | | | | 160 |

| His | Ser | Glu | Gly | Thr | Gly | Leu | Thr | Glu | Glu | Ala | Lys | Leu | Leu | Thr |
|---|---|---|---|---|---|---|---|---|---|---|---|---|---|---|
| | | | | 165 | | | | | 170 | | | | | 175 |

| Asp | Tyr | Val | Tyr | His | Thr | Leu | Ala | Ala | Lys | Ala | Ser | Gly | Glu | Leu | Cys |
|---|---|---|---|---|---|---|---|---|---|---|---|---|---|---|---|
| | | | 180 | | | | | 185 | | | | | 190 | | |

| Leu | Lys | Tyr | Ile | Phe | Ser | Phe | Gly | Ala | Phe | Ala | Arg | Lys | Pro | Leu | Leu |
|---|---|---|---|---|---|---|---|---|---|---|---|---|---|---|---|
| | | 195 | | | | | 200 | | | | | 205 | | | |

| Gln | Arg | Tyr | Val | His | Gln | Lys | His | Cys |
|---|---|---|---|---|---|---|---|---|
| | 210 | | | | | 215 | | |

<210> SEQ ID NO 10
<211> LENGTH: 349
<212> TYPE: PRT
<213> ORGANISM: Homo sapiens

<400> SEQUENCE: 10

| Met | Ala | Ala | Glu | Glu | Glu | Val | Asp | Ser | Ala | Asp | Thr | Gly | Glu | Arg |
|---|---|---|---|---|---|---|---|---|---|---|---|---|---|---|
| 1 | | | | 5 | | | | | 10 | | | | | 15 |

| Ser | Gly | Trp | Leu | Thr | Gly | Trp | Leu | Pro | Thr | Trp | Cys | Pro | Thr | Ser | Ile |
|---|---|---|---|---|---|---|---|---|---|---|---|---|---|---|---|
| | | | 20 | | | | | 25 | | | | | 30 | | |

| Ser | His | Leu | Lys | Glu | Ala | Glu | Glu | Lys | Met | Leu | Lys | Cys | Val | Pro | Cys |
|---|---|---|---|---|---|---|---|---|---|---|---|---|---|---|---|
| | | | 35 | | | | | 40 | | | | | 45 | | |

| Thr | Tyr | Lys | Lys | Glu | Pro | Val | Arg | Ile | Ser | Asn | Gly | Asn | Lys | Ile | Trp |
|---|---|---|---|---|---|---|---|---|---|---|---|---|---|---|---|
| | 50 | | | | | 55 | | | | | 60 | | | | |

| Thr | Leu | Lys | Phe | Ser | His | Asn | Ile | Ser | Asn | Lys | Thr | Pro | Leu | Val | Leu |
|---|---|---|---|---|---|---|---|---|---|---|---|---|---|---|---|
| 65 | | | | | 70 | | | | | 75 | | | | | 80 |

| Leu | His | Gly | Phe | Gly | Gly | Gly | Leu | Gly | Leu | Trp | Ala | Leu | Asn | Phe | Gly |
|---|---|---|---|---|---|---|---|---|---|---|---|---|---|---|---|
| | | | | 85 | | | | | 90 | | | | | 95 | |

Asp Leu Cys Thr Asn Arg Pro Val Tyr Ala Phe Asp Leu Leu Gly Phe

```
            100                 105                 110
Gly Arg Ser Ser Arg Pro Arg Phe Asp Ser Asp Ala Glu Glu Val Glu
            115                 120                 125

Asn Gln Phe Val Glu Ser Ile Glu Glu Trp Arg Cys Ala Leu Gly Leu
        130                 135                 140

Asp Lys Met Ile Leu Leu Gly His Asn Leu Gly Phe Leu Ala Ala
145                 150                 155                 160

Ala Tyr Ser Leu Lys Tyr Pro Ser Arg Val Asn His Leu Ile Leu Val
                165                 170                 175

Glu Pro Trp Gly Phe Pro Glu Arg Pro Asp Leu Ala Asp Gln Asp Arg
            180                 185                 190

Pro Ile Pro Val Trp Ile Arg Ala Leu Gly Ala Ala Leu Thr Pro Phe
        195                 200                 205

Asn Pro Leu Ala Gly Leu Arg Ile Ala Gly Pro Phe Gly Leu Ser Leu
            210                 215                 220

Val Gln Arg Leu Arg Pro Asp Phe Lys Arg Lys Tyr Ser Ser Met Phe
225                 230                 235                 240

Glu Asp Asp Thr Val Thr Glu Tyr Ile Tyr His Cys Asn Val Gln Thr
                245                 250                 255

Pro Ser Gly Glu Thr Ala Phe Lys Asn Met Thr Ile Pro Tyr Gly Trp
            260                 265                 270

Ala Lys Arg Pro Met Leu Gln Arg Ile Gly Lys Met His Pro Asp Ile
        275                 280                 285

Pro Val Ser Val Ile Phe Gly Ala Arg Ser Cys Ile Asp Gly Asn Ser
        290                 295                 300

Gly Thr Ser Ile Gln Ser Leu Arg Pro His Ser Tyr Val Lys Thr Ile
305                 310                 315                 320

Ala Ile Leu Gly Ala Gly His Tyr Val Tyr Ala Asp Gln Pro Glu Glu
                325                 330                 335

Phe Asn Gln Lys Val Lys Glu Ile Cys Asp Thr Val Asp
            340                 345

<210> SEQ ID NO 11
<211> LENGTH: 269
<212> TYPE: PRT
<213> ORGANISM: Oryza sativa

<400> SEQUENCE: 11

Val His Gly Tyr Gly Ala Ser Gln Gly Phe Phe Arg Asn Phe Asp
1               5                   10                  15

Ala Leu Ala Ser Arg Phe Arg Val Ile Ala Ile Asp Gln Leu Gly Trp
                20                  25                  30

Gly Gly Ser Ser Arg Pro Asp Phe Thr Cys Lys Ser Thr Glu Glu Thr
            35                  40                  45

Glu Ala Trp Phe Ile Asp Ser Phe Glu Glu Trp Arg Lys Ala Lys Asn
        50                  55                  60

Leu Ser Asn Phe Ile Leu Leu Gly His Ser Phe Gly Gly Tyr Val Ala
65                  70                  75                  80

Ala Lys Tyr Ala Leu Gln His Pro Glu His Val Gln His Leu Ile Leu
                85                  90                  95

Val Gly Pro Ala Gly Phe Ser Ser Glu Thr Glu His Ser Ser Glu Trp
            100                 105                 110

Leu Thr Lys Phe Arg Ala Thr Trp Lys Gly Met Leu Val Asn His Leu
        115                 120                 125
```

-continued

```
Trp Glu Ser Asn Phe Thr Pro Gln Arg Ile Val Arg Gly Leu Gly Pro
        130                 135                 140

Trp Gly Pro Gly Leu Val Gln Arg Tyr Thr Ser Ala Arg Phe Gly Ser
145                 150                 155                 160

His Ser Thr Asp Tyr Ile Tyr His Thr Leu Ala Ala Lys Ala Ser Gly
                165                 170                 175

Glu Leu Cys Leu Lys His Ile Phe Ser Phe Gly Ala Phe Val Arg Lys
            180                 185                 190

Pro Leu Leu Gln Ser Ala Ser Asp Trp Lys Val Pro Thr Thr Phe Ile
        195                 200                 205

Tyr Gly Gln Gln Asp Trp Met Asn Tyr Gln Gly Ala Gln Gln Ala Arg
210                 215                 220

Lys Glu Met Lys Gly Gly His Phe Val Phe Ile Asp Pro Ser Gly Phe
225                 230                 235                 240

His Ser Ala Val Phe His Ala Cys Arg Lys Phe Leu Ser Gly Asp Gly
                245                 250                 255

Glu Glu Gly Leu Ser Leu Pro Glu Gly Leu Thr Ser Ala
            260                 265
```

<210> SEQ ID NO 12
<211> LENGTH: 351
<212> TYPE: PRT
<213> ORGANISM: Mus musculus

<400> SEQUENCE: 12

```
Met Lys Ala Met Ala Ala Glu Glu Val Asp Ser Ala Asp Ala Gly
1               5                   10                  15

Gly Gly Ser Gly Trp Leu Thr Gly Trp Leu Pro Thr Trp Cys Pro Thr
            20                  25                  30

Ser Thr Ser His Leu Lys Glu Ala Glu Lys Met Leu Lys Cys Val
            35                  40                  45

Pro Cys Thr Tyr Lys Lys Glu Pro Val Arg Ile Ser Asn Gly Asn Arg
        50                  55                  60

Ile Trp Thr Leu Met Phe Ser His Asn Ile Ser Ser Lys Thr Pro Leu
65                  70                  75                  80

Val Leu Leu His Gly Phe Gly Gly Gly Leu Gly Leu Trp Ala Leu Asn
                85                  90                  95

Phe Glu Asp Leu Ser Thr Asp Arg Pro Val Tyr Ala Phe Asp Leu Leu
            100                 105                 110

Gly Phe Gly Arg Ser Ser Arg Pro Arg Phe Asp Ser Asp Ala Glu Glu
        115                 120                 125

Val Glu Asn Gln Phe Val Glu Ser Ile Glu Glu Trp Arg Cys Ala Leu
130                 135                 140

Arg Leu Asp Lys Met Ile Leu Leu Gly His Asn Leu Gly Gly Phe Leu
145                 150                 155                 160

Ala Ala Ala Tyr Ser Leu Lys Tyr Pro Ser Arg Val Ser His Leu Ile
                165                 170                 175

Leu Val Glu Pro Trp Gly Phe Pro Glu Arg Pro Asp Leu Ala Asp Gln
            180                 185                 190

Glu Arg Pro Ile Pro Val Trp Ile Arg Ala Leu Gly Ala Ala Leu Thr
        195                 200                 205

Pro Phe Asn Pro Leu Ala Gly Leu Arg Ile Ala Gly Pro Phe Gly Leu
210                 215                 220

Ser Leu Val Gln Arg Leu Arg Pro Asp Phe Lys Arg Lys Tyr Ser Ser
225                 230                 235                 240
```

```
Met Phe Glu Asp Asp Thr Val Thr Glu Tyr Ile Tyr His Cys Asn Val
                245                 250                 255

Gln Thr Pro Ser Gly Glu Thr Ala Phe Lys Asn Met Thr Ile Pro Tyr
            260                 265                 270

Gly Trp Ala Lys Arg Pro Met Leu Gln Arg Ile Gly Gly Leu His Pro
        275                 280                 285

Asp Ile Pro Val Ser Val Ile Phe Gly Ala Arg Ser Cys Ile Asp Gly
    290                 295                 300

Asn Ser Gly Thr Ser Ile Gln Ser Leu Arg Pro Lys Ser Tyr Val Lys
305                 310                 315                 320

Thr Ile Ala Ile Leu Gly Ala Gly His Tyr Val Tyr Ala Asp Gln Pro
                325                 330                 335

Glu Glu Phe Asn Gln Lys Val Lys Glu Ile Cys His Thr Val Asp
            340                 345                 350

<210> SEQ ID NO 13
<211> LENGTH: 344
<212> TYPE: PRT
<213> ORGANISM: Danio rerio

<400> SEQUENCE: 13

Met Ala Glu Glu Thr Val Leu Ala Asp Thr Gly Ser Trp Trp Ser Ala
1               5                   10                  15

Asp Trp Leu Pro Ser Trp Cys Pro Thr Ser Lys Asp Gln Leu Lys Gln
            20                  25                  30

Ala Glu Glu Arg Met Leu Gln Asn Ile Ala Ser Lys Leu Cys Arg Gln
        35                  40                  45

Ser Val His Ile Ser Asp Lys Asn Ser Leu Trp Thr Leu Ile Ser Lys
    50                  55                  60

Gly Pro Ala Glu Asn Lys Thr Pro Leu Val Leu Leu His Gly Phe Gly
65                  70                  75                  80

Gly Gly Val Gly Leu Trp Ala Leu Asn Leu Asp Ser Leu Ser Gln Gln
                85                  90                  95

Arg Pro Val Tyr Ala Phe Asp Leu Leu Gly Phe Gly Gln Ser Ser Arg
            100                 105                 110

Pro His Phe Asn Thr Asp Ala Gln Glu Ala Glu Ile Gln Phe Val Glu
        115                 120                 125

Ser Ile Glu Gln Trp Arg Glu Lys Leu Gly Leu Glu Ser Met Val Met
    130                 135                 140

Val Gly His Asn Leu Gly Gly Tyr Leu Ala Ala Ser Tyr Ala Ile Thr
145                 150                 155                 160

Tyr Pro Thr Arg Val Lys His Leu Ile Leu Val Glu Pro Trp Gly Phe
                165                 170                 175

Pro Glu Arg Pro Glu Pro Gly Asn Gln Asp Arg Pro Ile Pro Val Trp
            180                 185                 190

Ile Lys Ala Ile Gly Ala Met Leu Ser Pro Phe Asn Pro Leu Ala Gly
        195                 200                 205

Leu Arg Leu Ala Gly Pro Leu Gly Pro Thr Leu Val Gln Thr Leu Arg
    210                 215                 220

Pro Asp Phe Lys Lys Lys Phe Ala Thr Met Phe Asp Asp Asn Arg Val
225                 230                 235                 240

Thr Glu Tyr Ile Tyr His Leu Asn Val Gln Ser Pro Ser Gly Glu Thr
                245                 250                 255

Ala Phe Lys Asn Met Thr Ile Pro Tyr Gly Trp Ala Lys Arg Pro Met
```

```
                        260                 265                 270
Leu Gln Arg Ile Gly Leu Ile His Asp Asp Ile Pro Ile Thr Val Ile
            275                 280                 285

Tyr Gly Ser Arg Ser Ser Ile Asp Gly His Ser Gly Asn Ser Ile Lys
            290                 295                 300

Glu Met Arg Pro Asn Ser His Val Glu Ile Val Ile Arg Gly Ala
305                 310                 315                 320

Gly His Tyr Val Tyr Ala Asp Gln Pro Glu Asp Phe Asn Gln Lys Ile
                325                 330                 335

Leu His Val Cys Asp Thr Ile Ser
            340
```

<210> SEQ ID NO 14
<211> LENGTH: 444
<212> TYPE: PRT
<213> ORGANISM: Caenorhabditis elegans

<400> SEQUENCE: 14

```
Met Phe Gln Lys Thr Asp Phe Leu Ser Lys Ile Phe Ser Ser Ser Ser
1               5                   10                  15

His Pro Leu Thr Gly Ser Gln Asn Ile Val Val Lys Asp Pro Gln Thr
            20                  25                  30

Leu Asp Phe Ala Met Gln Ser Gln Asn Glu Ile Val Cys Ser Leu Arg
        35                  40                  45

Glu Arg Ser His Met Asn Thr Met Ser Tyr Ala Gln Thr Gln Met Met
50                  55                  60

Ala Ile Asp Glu Ile Arg Ala Phe Gln Ser Glu Gly His Leu His Leu
65                  70                  75                  80

Lys Tyr Ile Ser Leu Ile Ile Ala Met Met Ala Glu Thr Ala Val Val
                85                  90                  95

Thr Ser Arg Ser Trp Phe Pro Tyr Phe Ser Cys Pro Ser Lys Ser Gln
            100                 105                 110

Arg Leu Ala Glu Ala Glu Gly Arg Ile Leu Ser Ala Leu Gly Ile Lys
        115                 120                 125

Tyr Leu Ala Arg Leu Ile Gln Ile Pro Phe Lys Asn Thr Glu Ile Ser
    130                 135                 140

Thr Ile Thr Val Asn Cys Glu Ser Glu Gln Pro Ile Val Lys Ala Lys
145                 150                 155                 160

Tyr Pro Ile Val Leu Ile His Gly Phe Gly Ala Gly Val Ala Leu Trp
                165                 170                 175

Gly Ser Ala Ile Lys Arg Leu Ala Gln Phe Gln Thr Val His Ala Phe
            180                 185                 190

Asp Leu Pro Gly Phe Gly Arg Ser Ser Arg Pro Lys Phe Ser Ser Asp
        195                 200                 205

Pro Glu Thr Ala Glu Thr Glu Met Ile Asp Ser Ile Glu Gln Trp Arg
    210                 215                 220

Asp Lys Met Asn Leu Glu Lys Met Asn Leu Val Gly His Ser Phe Gly
225                 230                 235                 240

Gly Tyr Leu Ala Thr Ser Tyr Ala Leu Lys Tyr Pro Lys Arg Val Glu
                245                 250                 255

Asn Leu Ile Leu Ala Asp Pro Trp Gly Phe Asn Glu Met Asp Pro Glu
            260                 265                 270

Phe Ala Gln Lys Leu Thr Ser Arg Gln Lys Asn Ile Phe Trp Val Ile
        275                 280                 285
```

```
Gln Gln Phe Asn Pro Leu Ala Val Leu Arg Leu Val Gly Gly Tyr Gly
        290                 295                 300
Pro Ser Leu Val Arg Arg Leu Arg Pro Asp Leu Ala Leu Lys Tyr Ser
305                 310                 315                 320
Glu Asp Val Tyr Asp Tyr Ile Tyr Leu Ala Asn Ser Arg Asp Pro Thr
                325                 330                 335
Gly Glu Glu Val Phe Lys Cys Leu Ser Glu Asn Leu Gly Trp Ala Lys
            340                 345                 350
Gln Pro Met Ser Lys Arg Phe His Glu Leu Asp Asn Thr Val Pro Val
        355                 360                 365
Thr Phe Ile His Gly Glu Arg Ser Trp Ile Asp Trp Arg Thr Thr Arg
370                 375                 380
Arg Leu Phe Gly Glu Leu Glu His Val Glu Ser His Ile Met Asp Ser
385                 390                 395                 400
Ala Gly His His Val Tyr Ala Asp Asp Ala Asp Lys Phe Val Gln Leu
                405                 410                 415
Val Ile Gly Ser Leu Lys Asp Gly Lys Thr Gly Glu Leu Val Pro Glu
            420                 425                 430
Glu Val Asn Leu Glu Glu Glu Ile Val Thr Pro Ile
        435                 440

<210> SEQ ID NO 15
<211> LENGTH: 278
<212> TYPE: PRT
<213> ORGANISM: Vitis vinifera

<400> SEQUENCE: 15

Val His Gly Tyr Gly Ala Ser Gln Gly Phe Phe Arg Asn Phe Asp
1               5                   10                  15
Ala Leu Ala Arg Arg Phe Arg Val Ile Ala Ile Asp Gln Leu Gly Trp
                20                  25                  30
Gly Gly Ser Ser Arg Pro Asp Phe Thr Cys Lys Ser Thr Glu Glu Thr
            35                  40                  45
Glu Ala Trp Phe Ile Asp Ser Phe Glu Glu Trp Arg Lys Ala Lys Asn
50                  55                  60
Leu Ser Asn Phe Ile Leu Leu Gly His Ser Val Gly Gly Tyr Val Ala
65                  70                  75                  80
Ala Lys Tyr Ala Leu Lys His Pro Glu His Ile Gln His Leu Ile Leu
                85                  90                  95
Val Gly Pro Ala Gly Phe Ser Leu Glu Ser Asp Gly Lys Ser Glu Trp
            100                 105                 110
Leu Thr Arg Glu Arg Ala Thr Trp Lys Gly Ala Val Leu Asn His Leu
        115                 120                 125
Trp Glu Ser Asn Phe Thr Pro Gln Lys Leu Val Arg Gly Ile Gly Pro
    130                 135                 140
Trp Gly Pro Asp Leu Val Arg Lys Tyr Thr Ser Ala Arg Phe Ser Ser
145                 150                 155                 160
Tyr Ser Thr Gly Asp Leu Leu Thr Glu Glu Ser Lys Leu Leu Thr
                165                 170                 175
Asp Tyr Val Tyr His Thr Val Ala Ala Lys Ala Ser Gly Glu Leu Cys
            180                 185                 190
Leu Lys Tyr Ile Phe Ser Phe Gly Ala Phe Ala Arg Leu Pro Leu Leu
        195                 200                 205
His Ser Ala Ser Glu Trp Lys Val Pro Thr Thr Phe Ile Tyr Gly Phe
    210                 215                 220
```

Glu Asp Trp Met Asn Tyr Gln Gly Ala Gln Glu Ala Arg Lys Gln Met
225                 230                 235                 240

Lys Val Pro Cys Glu Ile Ile Arg Val Pro Gln Val Ser Leu Ser Leu
            245                 250                 255

Ser Leu Ser Leu Trp Arg Lys Ile Asn Arg Lys Thr Tyr Asn Ser Ser
        260                 265                 270

Trp Leu Thr Glu Phe Cys
        275

<210> SEQ ID NO 16
<211> LENGTH: 289
<212> TYPE: PRT
<213> ORGANISM: Physcomitrella patens

<400> SEQUENCE: 16

Val His Gly Tyr Ala Ala Ser Gln Gly Phe Phe Arg Asn Phe Asp
1               5                   10                  15

Ala Leu Ala Ser Lys Phe Arg Val Ile Ala Ile Asp Gln Ile Gly Trp
            20                  25                  30

Gly Ala Ser Ser Arg Pro Asp Phe Thr Cys Lys Asn Thr Glu Glu Ala
        35                  40                  45

Glu Ser Trp Phe Val Glu Ser Leu Glu Glu Trp Arg Lys Ala Lys Gln
50                  55                  60

Leu Gly Asp Phe Ile Leu Leu Gly His Ser Leu Gly Gly Tyr Val Ala
65                  70                  75                  80

Ser Arg Tyr Ala Leu Lys Tyr Pro Asp His Val Lys His Leu Val Leu
            85                  90                  95

Val Gly Pro Ala Gly Phe Asn Val Asp Ser Asp Arg Ile Met Lys Phe
        100                 105                 110

Lys Ser Thr Trp Pro Gly Val Leu Ile Asn Cys Leu Trp Glu Ser Asn
    115                 120                 125

Phe Thr Pro Gln Lys Ile Ile Arg Gly Leu Gly Pro Trp Gly Pro Lys
130                 135                 140

Leu Val Asn Gly Tyr Ala Val Arg Arg Phe Gly Asn Ser Glu Gln Arg
145                 150                 155                 160

Asp Pro Leu Ser Asp Val Glu Thr Lys Leu Leu Ser Asp Tyr Ile Phe
            165                 170                 175

His Thr Ala Ala Ala Lys Ala Ser Gly Glu Leu Cys Leu Asn Tyr Ile
        180                 185                 190

Phe Ser Phe Gly Ala Leu Ala Arg Thr Pro Leu Val Asp Ser Ala Pro
    195                 200                 205

Asn Trp Lys Val Pro Thr Ser Phe Ile Tyr Gly Thr His Asp Trp Met
210                 215                 220

Asn Phe Glu Gly Ala Lys Glu Ala Arg Lys Arg Leu Gly Ser Asn Leu
225                 230                 235                 240

Pro Cys Glu Ile Leu Arg Val Pro Arg Ala Gly His Phe Val Phe Leu
            245                 250                 255

Asp Asn Ala Pro Lys Phe His Asp Ala Leu Phe Tyr Ala Cys Arg Asn
        260                 265                 270

Tyr Leu Pro Gly Gly Ser Arg Phe Glu Leu Pro Glu Glu Ile Leu Glu
    275                 280                 285

Val

<210> SEQ ID NO 17

```
<211> LENGTH: 6
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(5)
<223> OTHER INFORMATION: X = any amino acid

<400> SEQUENCE: 17

His Xaa Xaa Xaa Xaa Asp
1               5

<210> SEQ ID NO 18
<211> LENGTH: 1448
<212> TYPE: DNA
<213> ORGANISM: Brassica napus

<400> SEQUENCE: 18
ggtctcagtc atttccacaa tctcagattc tttgactttt gtctcctctc tagattattg      60
gattcgtgta tgagcttaaa ccggttccgg ttaagaatgg cggggaaat  ctcaaagaca     120 aagctcggat cttcctcttc ttcctccgct tctgctgctg catcagctgc aacgaacgca     180
gcgaaatcga gatggaagat cttatggccc aattccctcc gctggatccc acctccacc     240 gacaacatca tcgccgccga gaaccgcctt ctctccatcc tcaagacgcc ttatatacaa     300
gagcaagtga atattggctc tggaccacca ggttcgaaaa tcaggtggtt taggtcttcc     360
agcgatgagt ctaggtacat caacactgtt acctttgacg ccaaggaggg ttctcctacg     420
cttgtgatgg ttcatggtta tgctgcttct caaggcttct tctttcgtaa cttcgatgct     480
cttgccagtc ggtttaaggt catcgctatt gatcaacttg ggtggggtgg atcgagtagg     540
cctgatttta cttgtaaaag cacagaagaa acagaggcgt ggtttatcga ctcatttgag     600
gaatggcgca aatccaagaa tctcagtaac ttcattctgt taggacattc ttttggaggt     660
tatgttgctg ctaagtacgc gcttaagcac cctgagcatg ttcagcactt ggttctggtg     720
ggatctgctg gtttctcagc agaatcagat gccaagtcgg agtggctcac taagttcaga     780
gcaacgtgga aaggtgctct tctaaatcat ctatgggagt ccaatttcac tcctcagaag     840
ctgattagag gattaggtcc ttggggtccg ggtcttgtga accggtatac aagtgcaaga     900
tttggagcac attcggtggg aactgtgcta acagatgagg agtccagatt gctcaccgat    960
tatgtgtatc atacgttggc tgcaaaggct agtggagagt tgtgcttgaa atacatcttc    1020
tccttcggag catttgctcg gaagccactc ttacaaagtg catcagagtg gaaagtgcca    1080
acaactttta tctatggaat gaatgattgg atgaactatc aaggtgcagt ggaagcacgg    1140
aaacacatga aggtcccttg cgaaatcatt cgtgttccac agggtggcca ttttgtgttc    1200
atagacaacc cagctggttt tcattcagca gtgatgtatg cttccgcaa  gtatatatct    1260 caagactctt ctcatcaaga actcattcca gatggttttc aattggttta atcgtgctat    1320
tgttcgtttt accttatcaa ctttactta  ttaaaaatgt acaaaaacca tatataaaag    1380
agaaacaatt attttcttaa tgttggttgt gtttgtactt tggagttcta agacctcttt    1440
ccattctc                                                               1448

<210> SEQ ID NO 19
<211> LENGTH: 1672
<212> TYPE: DNA
<213> ORGANISM: Populus sp.
```

-continued

<400> SEQUENCE: 19

| | | | | | |
|---|---|---|---|---|---|
| aaatttgaat | catttccgt | tctctaattt | gtatgattat | ttctatatga | ttttatgaac | 60 |
| ctgtttcgtt | cacgcgtttc | aagctcaata | gtatctacca | tgggcgaaga | gcaaggatcc | 120 |
| tctgcttccg | cttccaccgc | aacatcatca | tcacgggcaa | aaacaagatc | tacatggccc | 180 |
| tctattcttc | gctggatccc | cacttccacc | gatcacgtca | tcgccgccga | aaaacgcctt | 240 |
| ttctctctag | tcaagactcc | gtacgtggta | gagcaagtga | atattggttc | gggtccacca | 300 |
| gggtcgaaga | ctcggtggtt | tcgatctaag | agtgatgagc | ctaggtttat | caatacggtg | 360 |
| acttttcaaa | gcaaagagga | ttctcctacg | cttgtaatgg | tccatggata | tggtgcttct | 420 |
| caaggtttct | tcttcaggaa | ttttgatgct | cttgctagcc | gtttcaagat | cattgctatt | 480 |
| gatcagcttg | gttggggtgg | atcaagtaga | cctgacttta | cctgcaaaag | cactgaagaa | 540 |
| actgaggcgt | ggtttattga | ctcctttgag | gaatggcgaa | aagcaaagaa | cctcagtaac | 600 |
| ttcatattgc | ttgggcattc | atttggaggg | tatgttgcgg | ctaaatatgc | actcaagcat | 660 |
| cccgagcgtg | ttaagcagtt | gatttagtg | ggatctgctg | gattttcatc | agaatcagat | 720 |
| tccaagtctg | agtggctcgc | ccaatttagg | gcaacttgga | aaggagccat | tttgaatcat | 780 |
| ttgtgggagt | ctaattttac | tcctcagaag | gttgtcagag | ggttgggtcc | ttggggtcct | 840 |
| ggtctggtac | gtcgctacac | aactgctaga | tttggtgcat | attcaaccgg | agtagtattg | 900 |
| gctgaggagg | agtccaaatt | gctaacagat | tatgtgtatc | atactttagc | agccaaagct | 960 |
| agtggagagc | tatgcttgaa | atttatattt | tcttttggag | catatgcacg | gaagcccctt | 1020 |
| ttacagagtg | catcagaatg | gaaagtgcca | accactttca | tatatggctt | cgaagattgg | 1080 |
| atgagctacg | aaggtgccca | acaagctcgc | cagcatatga | aggttccatg | cgagatcatt | 1140 |
| cgggttccac | agggcgggca | ctttgtattc | atagacaacc | caactgcgtt | ccattcagct | 1200 |
| gtgtttatg | cttgtcggat | gtacatttca | cctaatcttg | aaactgaaca | tctccctgaa | 1260 |
| ggtctcacgc | ttgcgtagga | aatgttacca | taaatctta | attatttgtg | tatgattcat | 1320 |
| ttatttata | gctccgtcac | aaatttatac | taggatgtat | taataaaaca | ttcattttc | 1380 |
| atgtacatgt | acatctaatg | tacttgagtt | gtgctggatg | cagctgtatt | tattgaatat | 1440 |
| gagctccgga | agttgaaact | ttcaaaaatg | gtcatcaaac | agttcgtggt | ttcctcgacc | 1500 |
| cgtggagaaa | gtttctacat | taatcatact | gaaaatagga | aaatgtttgt | ttatgaaagg | 1560 |
| gatgcactat | agggtgcatt | ttggcaattt | catagtgtga | taattaatta | cgtgcggata | 1620 |
| aagggcttgg | ttgatatcat | atttataaa | atcttatttg | agatttgttt | tc | 1672 |

<210> SEQ ID NO 20
<211> LENGTH: 1134
<212> TYPE: DNA
<213> ORGANISM: Oryza sativa

<400> SEQUENCE: 20

| | | | | | |
|---|---|---|---|---|---|
| aagaactccg | cccagaagaa | gaggcgacga | gagtgacagg | ccgaggaggg | aggggggattc | 60 |
| gaggatcgca | tgcgccgtgc | cgccgccgcc | gccgtgacgg | tgacgacgac | gacgaggatg | 120 |
| gcggcggagg | ggatgtccac | ggccgccgcg | cagcggagg | cgacggcgac | ggcggcgccc | 180 |
| gcggcggggt | cgaggtgggg | gagggcgtgg | ccgtccgcgc | tgcgctggat | cccgacctcc | 240 |
| accgaccgca | tcatcgccgc | cgagaagcgg | ctcctctcca | tagtcaaaac | tggctatgtc | 300 |
| caagaacaag | ttaacattgg | ctcctctcca | cccggatcaa | aagttagatg | gtttagatca | 360 |
| tcaagtgatg | agccaagatt | catcaatact | gtaacatttg | atagcgaaga | aaatgctccc | 420 |

-continued

```
acccttgtca tggtccatgg gtatggtgct tcacagggtt tcttctttcg aaactttgat      480
gcccttgcaa gccgtttcag ggtgattgcc attgatcagc ttggttgggg tggatcaagt      540
agacctgact tcacttgtaa aagtactgaa gaaactgagg catggttcat agattccttt      600
gaggaatggc gcaaagcaaa gaatctcagt aattttatat tgctcggtca ctcttttgga      660
ggatatgttg cggcaaagta cgctttacag catcctgagc acgtccaaca cttgatcttg      720
gtcggccctg ctggcttttc atcagaaaca gagcatagct ctgagtggtt aaccaagttc      780
cgagctacat ggaaaggcat gctagtgaat catctatggg agtccaattt tactcctcaa      840
agaatagtga gaggattggg tccttgggga ccaggcttag ttcagagata taccagtgcc      900
agatttggct cacattcaac aggtgaatta ctaacagaac aggaatccac attactgaca      960
gattacattt accatacttt ggctgccaaa gctagtggga agttgtgctt aaaacatata     1020
tttcctttg gggcattcgc gaggaaacct cttctgcaaa ggtcagtttt cttcgtatta     1080
actaaatgta ggagttatga gcaccctggt gatcttgaga gcatatgcac aata          1134
```

<210> SEQ ID NO 21
<211> LENGTH: 1608
<212> TYPE: DNA
<213> ORGANISM: Triticum aestivum
<220> FEATURE:
<221> NAME/KEY: misc_feature
<222> LOCATION: (8)..(8)
<223> OTHER INFORMATION: n is a, c, g, or t

<400> SEQUENCE: 21

```
aaaacaancg cggcagagcc tactcgtgtg actaccccta ccaatctgcc cagcagagcc       60
ggcgcggggg gaacacgctc gctcgctcgc gccgcgttgc atgcgccggg cagccgccgc      120
cgccaccacc aggatcagga tcgggatggc ggtggaggag gtcaggcagg cgtccgcggc      180
cgccacggcg gccgaggccg cgtccgcgtc ggcgctggat ccccacctcc accgaacgca      240
tcatcgccgc agagaagcga ctcctctcca tcctcaaaac tgggtatgtc caagaacaag      300
tcaacattgg ctctgctcca cctgggtcaa aagtaaaatg gtttagatca tcaagtgatg      360
agccaaggtt catcaataca gtgacatttg atagcaagga gaatgctccc acccttgtca      420
tggtccatgg ttatggtgcg tcacaggggt tcttctttag aaactttgat gcccttgcaa      480
gccgtttccg ggtgattgcc attgaccagc ttggttgggg tggatcaagc agacctgact      540
ttgactgtag aagtactgaa gaaaccgagg cttggttcat agattctttt gaggaatggc      600
gcaaagcaaa aaacctcagt aatttttatat tgcttggtca ttctttcgga ggatatgttg      660
cggcaaagta tgccttacag catcctgaac atgttcagca cttgattttg gttggttctg      720
ctggcttttc gtcagaaaca gatcatagtt ctgagtggtt aaccaagttc cgtgcaacgt      780
ggaaaggcat gctagtaaac catctttggg agtccaattt cactcctcag agaattgtga      840
gaggattagg tccttggggc ccagatttag ttcggagata taccactgct aggtttggct      900
cacattcaac aggtgaatta ctaacagaaa acgagtcctc cttgctgaca gattacattt      960
accacacttt agctgccaaa gctagtggag agctgtgctt aaaacatatt ttttccttgg     1020
gggcatttgc aaggaaacca cttctgcaca gtgcatccga ctggaaagtg ccaactactt     1080
tcatatatgg tcacgacgat tggatgaatt accaaggggc gcagcaagca ccgcaaggac     1140
atgaaagttc ctttgcgaaa tcatcagagt cccacaggaa ggacattttg ggtttataga     1200
taaccccctgg ggggtttcca ccccgggggga tctttctacc gcggggccgg aaatttttta     1260
```

```
tctgggagag gcagagggag ggtctctctc cttcctgatg gctttgatat tctgcattgc    1320
gggggcctcc ctcggggggac ccccatcccg aaataatggg tatgggactt aaaagcaaag    1380
gttatccgac ccatagaaaa aggctccatg gacgcgcggg gcgtcccccc aactcggtta    1440
tttagaatgg atgaatctc ctgcgaaaat aagtcttttc tctattggta gttctccgtc     1500 accccctcaac actctaaact gaagaacaaa cttaagctgc cttgtcgtat gccgggcgcc    1560
tccgaatatt aaactaaagg ctcatatacg cgcacaacaa acacccc                   1608
```

<210> SEQ ID NO 22
<211> LENGTH: 811
<212> TYPE: DNA
<213> ORGANISM: Solanum tuberosum

<400> SEQUENCE: 22

```
gtgaaaccgg cgaaggagag aatgaggtta agtttcttgg aaaggcaata gagaacttgg     60
agaacactct atctagcaca tacgcctata ttttggggag ttcagcgaca aaagggaaa     120 ttaattatct gttgcatcaa tcgcatgagc atcggactaa ggaggttatc gaattcattg    180
gtaaaaatgg cggaacaaat caattcatca gccgccgata acacagctgc cggagcaaaa    240
cggtggtcat tttggccctc ttctcttcgt tggatacccta catctactga ccacatcatc    300
gctgctgaaa aacgtcttct ttctcttgtt aggactcctt atacacaaga gcaggtcaac    360
attgggtctg gtccaccagg ttcaaaagtt agatggtttc gatcggtgag caatgaaccg    420
agatttatca atactgttac tttcgacagc aaagagggtt ctcctactct tgttatggtc    480
catggatatg gtgcctctca aggtttcttc tttcggaatt ttgctgccct tgcaaagcat    540
ttcaaagtaa ttgctattga tcagcttggc tggggtggat caagcaggcc tgacttcaca    600
tgcaaaagta ccgaagagac tgaaaattgg tttattgatt cctttgagga gtggcgcaaa    660
gccaaaaatc ttagcaactt tattttgctt gggcactctt tggagggta tgtcactgcc     720 aaatatgctc tcaagcatcc tgagcatgtt cagcagttga ttctggtagg accagccgga    780
tttacatcac aaactggaca tatgtctgaa c                                    811
```

<210> SEQ ID NO 23
<211> LENGTH: 1152
<212> TYPE: DNA
<213> ORGANISM: Oryza sativa

<400> SEQUENCE: 23

```
atggtttgtg ttagttacaa gatacaacct cctaaggttg tattaattgt tggtgtggtg     60
tttcttcctg gtttatgct ctcagctata ttgttaacaa atatacttca gttctttctt     120
cattttgctc tagatatatc tgaggctctt tgcaattttc taattggtgg tgcacttttt    180
atatctcttt acagaactgg ctatgtccaa gaacaagtta acattggctc ctctccaccc    240
ggatcaaaag ttagatggtt tagatcatca agtgatgagc aagattcat caatactgta     300 acatttgata gcgaagaaaa tgctcccacc cttgtcatgg tccatgggta tggtgcttca    360
cagggtttct tctttcgaaa ctttgatgcc cttgcaagcc gtttcagggt gattgccatt    420
gatcagcttg gttgggggtgg atcaagtaga cctgacttca cttgtaaaag tactgaagaa    480
actgaggcat ggttcataga ttcctttgag gaatggcgca aagcaaagaa tctcagtaat    540
tttatattgc tcggtcactc ttttggagga tatgttgcgg caagtacgc tttacagcat     600 cctgagcacg tccaacactt gatcttggtc ggccctgctg gcttttcatc agaaacagag    660
catagctctg agtggttaac caagttccga gctacatgga aaggcatgct agtgaatcat    720
```

```
ctatgggagt ccaattttac tcctcaaaga atagtgagag gattgggtcc ttggggacca      780
ggcttagttc agagatatac cagtgccaga tttggctcac attcaacaga ttacatttac      840
catactttgg ctgccaaagc tagtggagag ttgtgcttaa acatatatt ttcctttggg       900 gcattcgtga ggaaacctct tctgcaaagt gcatccgatt ggaaagtgcc aactactttc      960
atatatggcc aacaagattg gatgaattac caaggtgcac agcaagcacg gaaagaaatg     1020
aaaggaggac atttttgtgtt catagataat ccttcgggt tccactccgc ggtcttccac     1080
gcatgccgca gtttctatc tggagatgga gaggaaggcc tctctcttcc tgaaggccta     1140
acatcggcct ga                                                        1152

<210> SEQ ID NO 24
<211> LENGTH: 1405
<212> TYPE: DNA
<213> ORGANISM: Allium cepa

<400> SEQUENCE: 24
tccaattaga cggctctggt actttcctac ttaattgtta attagggaac gaaaattgga      60
atgatcagat ttagtgcacg aaaaatggca gaaatggcga cagctgaaac tacttcttct     120
tcaccagcat ctacttcaag atggaattgg cttcgatgga ttccgacctc tactgatcat     180
atcatcgctg ccgagaaacg cctcctctct atagtcaaaa ctggatatgt acaagagaag     240
gtaaatattg gttctggacc gcccgggtca aaaattagat ggttcaggtc atccagtgat     300
gactcgagat ttataaatac ggttactttt gatagcaagg acgatgctcc gactttagtc     360
atggtacatg gttatggtgc ttctcagggg ttttcttc gaaactttga tgctttggcc      420
agtcgctttc gagttattgc cattgatcag ctcggttggg gtggctcaag tcgtccagac     480
tttacttgca aaagcacgga agaaacggaa acctggttta ttgattcatt tgaggcatgg     540
cgtaaatcca aaaacttgag taacttcatt ttgcttgggc attctttgg aggatacgtg      600 gctgcaaaat atgctctgaa gcaccctgag catgtccaac atttaatatt ggtgggccct     660
gcaggcttca cgtcagaaac ggaacataaa tcagaatggt tgactaaatt cagagccact     720
tggaaaggag ctattttcaa tcatctctgg gaatccaact ttactcctca gaaagttatt     780
agaggtttag gaccatgggg cccagatatg gtacgaagat atactagtgc tagatttggt     840
tcttattcta atggcaccac attgacagat gaggagtcag ctttgcttac agattacata    900
taccacactt tagctgctaa agcaagtgga gaactgtgct tgaagtacat tttttcattt     960
ggagcattcg cacggaaacc tctttacag agtgcatctg agtggaaagt tcctactact     1020
ttcatatatg gctatcatga ctggatgaac taccaaggtg cacaacaagc tcgcaaagac     1080
atggaagtac cttgcgaaat cataagagtt cccgaggcag gcattttgtt gttcatagat     1140
aacccatctg gattccactc agctgtgttc cacgcatgtc gtaaatttat caacggtctt     1200
gcagaagaca acctctacct gaaggacttt catctgctta agtaatttg tatcacaaca     1260 catccatgct ataacacatt tccataattg ctttgcatcc aggctctatt acatagaaat     1320
caatttcgaa atgcataccc ttcacatcca gttaacgttt gtacaattaa acataggtct     1380
tggtatctta catttgcacg cgttt                                          1405

<210> SEQ ID NO 25
<211> LENGTH: 1457
<212> TYPE: DNA
<213> ORGANISM: Pinus sp.
<220> FEATURE:
```

```
<221> NAME/KEY: misc_feature
<222> LOCATION: (1455)..(1456)
<223> OTHER INFORMATION: n is a, c, g, or t

<400> SEQUENCE: 25
agctgaggcc caaaacatga tataaagacc aacaacacgg atgacactgc attaatggtc      60
gatgagcact cgaatgccca gtagatggtc cagaatggcc gaagaattag ctaaagtcga     120
agcaccagag gttgccaccg gaagtagatc gtggtctatc cttcgttggc ctcctgctct     180
cagatggatt cccacctcca tcaaagaagt ccttgcctcc gaacgcagtc tcctttccct     240
cgtcaagact ccctatgtgg aagaggaggt caatattggt agcgggccac ctggatcgaa     300
ggtaagatgg ttcaggtctt caagcaacga gccgcgcttc atacacactg ttacctatga     360
gactgccgaa aacagcaaag caccgacctt ggtgatggtt catggctacg ggcttccca     420
gggcttcttc ttccggaact tcgatgcact cgccagtcgc ttcagggtta ttgccatcga     480
ccaattggga tggggtgcct caagtcgacc tgactttacc tgtaaaagca cagaagaaac     540
tgaagcctgg ttcattgatt cattcgaaga atggcgtaaa gctaaaaact tggatcagtt     600
tatttttgcta ggtcattctt ttggaggtta tgtggctgca aaatatgctc tgaagtatcc     660
agagcatgtc aggcacctaa tattggtagg ctcagctgga ttctctgacg agtcaaataa     720
aaaggctgag tggtaacac aatttaaatc aacatggaag ggtgcaatat taaatcatct     780
ttgggaatct aacttcactc cacaaaagtt tgttcggagt ctagggcctt ggggtccacg     840
tatagtaaaa ggatatacaa gtgttcggtt tgtgacccgt acaactggtg atacattgaa     900
tgaagttgag gccaaattgc tttcagatta tgtctaccac acattagctg ctaaagcgtc     960
tggggagctg tgtctgaagt atatatttgc ttttggagca tttgctcgat cacctcttt    1020
aagaagtgcc tcagaatgga aagtaccaac cacctttatc tatggttatt atgactggat    1080
ggattatgaa ggagctgtgg aggctcgtaa acttatgagt gttcctgctg agatcataag    1140
agttcctcaa gcgggtcact ttgctttcct agacaatgca tcggcattcc attcagcagt    1200
gttgtatgct tgtcggaaat ttttttagcga gaatgaagaa aatgaaatct tccctgaagg    1260
gctaacaaga gtgtagcaat attgtgtaat acgagcattc aattgtttat aatttaagaa    1320
actggcagga gagtttgcct ttatatatta tttttatttgg acttaatata taacatggtg    1380
gaattccgtc atgaaaatgt tgactgaaaa tgattgcaaa gcttactgta taatcttgta    1440
tatgttattc ttttnnt                                                   1457

<210> SEQ ID NO 26
<211> LENGTH: 1174
<212> TYPE: DNA
<213> ORGANISM: Picea sp.

<400> SEQUENCE: 26
aagcaacaag ccgcgcttca tacatactat tacctacgag tctgccaaga acagcaacgc      60
accgactttg gtgatggttc atggctacgg ggcttcccag ggcttcttct tccggaactt     120
cgatgcactc gccagtcgct ttagggttat tgccatcgac caattgggat ggggtgcctc     180
aagtcgacct gacttcacct gtaaaagcac aaaagaaact gaagcctggt tcattgattc     240
atttgaagaa tggcgtaaag ccaaaaactt ggatcagttt attttgctag gtcactcttt     300
tggaggttat gtggctgcaa aatatgctat taagtatcca gagcatgtta agcacctaat     360
attggtaggc ccagctggat tctccgacga gtcaaataaa aaggctgagt ggataacaca     420
atttagaaca acatggaagg gtgtaatatt aaatcatctt tgggaatcta acttcactcc     480
```

```
acaaaagttt gttcggggtc tagggccttg gggtccacgt atagtgaacg gatatacaag    540
tgctcggttt gtaactggtt cgactggtga tatattgaat gaagtcgagg ccaaactgct    600
ttcggattat gtctaccaca ccttagctgc taaagcatct ggggagttgt gtctgaagta    660
tatattttct tttggagcat ttgctcgatc acctctttta aaatgtgcac cagaatggaa    720
ggtaccaacc acctttatct atggtcatca tgactggatg gattatgaag gagctgtgga    780
ggctcgtaaa cgtatgaatg ttcctgttga gatcataaga gttcctcaag ccggtcactt    840
tgctttccta gacaacgcat cggcatttca ttcagcagtg ttctatgctt gtcggaattt    900
ttttatcaag gatgaagaaa aagaaaactt cccagaaggg ataataagag tgtaacaata    960
tttgtgtagt acaagcattc attgctccta atttaagaaa ctggcatgca agtttgcctt   1020
tatatattat tttatttgaa ctttatgtat aaatatggtgg aattccatca tgaaaatgtt   1080
gactgataat ggttgtgaag ctttgtgcat aatcttgtat ttacgttatt cttttgatag   1140
ttgaaaatgt tgaatctagt tcactttagg tgcc                               1174

<210> SEQ ID NO 27
<211> LENGTH: 864
<212> TYPE: DNA
<213> ORGANISM: Sorghum bicolor

<400> SEQUENCE: 27
acacattcag cacttagttt tggttggtcc tgctggcttc tcgtcagaaa cagaccatag     60
ctctgagtgg ttaaccaagt ttcgagcaac atggaaaggc atgctagtga atcatctttg    120
ggagtccaat tttactcccc aaagagttat tagaggattg ggcccttggg gtccaggtct    180
agtacaaaga tataccagtg ccaggtttgg tacacgttca actggtgata tactaacaga    240
tcaagaatca acattgttga cagattatat ttaccatacc ttagctgcca aagctagtgg    300
agagctgtgc ttgaaatata tattttcctt cggggcattt gcaaggaaac ctcttctgca    360
gtgcgcatcc gattggaaag tgccgactac tttcatatat ggtcaggaag attggatgaa    420
ctaccaaggg gctcagcaag cacggaagga catgaaaagtt ccttgtgaaa taatcagggt    480
gccacagagt ggacattttg tgtttataga caacccttca gggttccact cggctgtctt    540
ctacgcgtgc cgtaatcttt tatcccaaaa tggggaggag ggcttcacat ttcctggtgg    600
cctaatatct gcatgaagtg gcatgttcaa caatcttatc gtgcccaaca atagtttata    660
tgaagcaaag atatacgatg gtggaaatct ttgctcattt ccaccaatct ggaaatattt    720
gtgccctctt ccaccaattt gttttgtatac ggattatgcc gtgtatatat tctgtgttga    780
ctgtaagaaa cataatgtat taacattatg taatgtatgt acgattcttt atttgatttt    840
caacttgcaa tacgcaagaa ccac                                           864

<210> SEQ ID NO 28
<211> LENGTH: 755
<212> TYPE: DNA
<213> ORGANISM: Saccharum officinarum

<400> SEQUENCE: 28
tagtgaatca tctttgggag tccaattttta ctccccaaag agttattaga ggattgggtc     60
cttggggtcc aggtctagta cgaagatata ccagtgccag gtttggtaca cgttcaactg    120
gtgaattact gacagatcaa gaatcgacat tgttaacaga ttatatttac catacccttag    180 ctgccaaagc tagtggagag ctgtgcttga aatatatatt ttccttcggg gcatttgcaa    240
```

```
ggaaacctct tctgcagtgc gcatccgatt ggaaagtgcc gactactttc atatatgggc    300
aggaagattg gatgaactac caaggggctc agcaagcacg gaaggacatg aaagttcctt    360
gtgaaataat cagggtgcca cagggtggac attttgtgtt tatagacaac ccttcagggt    420
tccactcggc tgtcttctac gcgtgccgta atcatgggga ggagggcttc acatttcctg    480
atggcctaat atctgcatga agtggcatgt tcaacaatct tgtcctgccc aagaatagtt    540
tatatgaagg aaagatatac gatggtggaa atctttgctc atttccacca atttggaaat    600
atctgtgccc tcgtccacca atttgtttgt atacggatca tgccgtgtgt atattctgtg    660
atgactgtaa gaaacataat gtattaacat tatgtaatgt atgtacgatt ctttatatga    720 tttttcgaatt gcaatacgcg agaaccattt tcttt                             755

<210> SEQ ID NO 29
<211> LENGTH: 1725
<212> TYPE: DNA
<213> ORGANISM: Zea mays

<400> SEQUENCE: 29
gggccgcacc gaccgaacct aaccgagagc acgagcatac ccgtcccgac tccgactgca     60
gagcatcagc cgaggagaaa agtcgggaga acgcgcgtg acgtctgccc gcgtcgtatg    120
cgccgcgctg ccgtcgccgc gacgacgacg acgaccagga tggcagccga ggagatgaga    180
cgggcctccg cctcaacggc cacggcggag atgccggcgt cgccggcgcc ggcgcaagcg    240
gggtcgaggt gggcgcgggt gtggccgcgc gcgctccggt ggatccccac ctccacggac    300
cgcatcatcg ccgccgagaa gcgactcctc acgatagtca aaactggata tgtccaggaa    360
cgagtcaaca ttggctctgc tccacctggg tcaaaagtaa gatggtttag gtcagcaagt    420
gatgaaccaa ggttcattaa tactgtaaca tttgatagca aggagaatgc ccccaccctg    480
gttatggtcc atggctatgg agcttcacag gggttcttct ttcgaaactt tgatgccctt    540
gcaagccgtt ttagggtgat tgccattgat cagcttggct ggggtggttc aagcagacct    600
gacttcacat gtaaaagtac cgaagaaact gaggcatggt tcatagattc tttcgaggag    660
tggcgcaagg ccaagaacct cagtaatttt atattgcttg gtcactcttt tggaggatat    720
gttgctgcaa aatatgcgct aaagcaccct gaacacgttc aacagttgat tttggttggt    780
cctgctggct tctcatcaga aacagagcat agctctgagt ggttaaccaa gtttcgagca    840
acatggaaag gcatgctaat gaatcgtctt tgggagtcca atttactcc ccaaagggtt    900 attagggat tgggtccttg gggtccaggt ctagtacaaa gatataccag tgccaggttt    960
ggtacaagtt ctactggtga attactaaca gatgaagaat cggcattgat gacagattat   1020
atgtaccata cgttagctgc caaagctagt ggagagctgt gcttgaaata tatattttcc   1080
ttcggggcat ttgcaaggaa acctcttctg cagtgcgcgt ccgattggaa agtgccgact   1140
actttcatat atgggcagca agattggatg aactaccaag cgctcagca agcacggaag   1200 gacatgaaag ttccttgtga ataatcagg gtgccgcagg gtggacattt tgtgttcata   1260
gacaaccctt cagggttcca ctcggctgtc ttctatgcgt gccgtaatct tctatcagta   1320 aatgagagg agggattcac atttcctgat ggcctaatat ctgcgtgaag tggcatgttc   1380
aacaagcttg ctcaacaaca gtttacataa agcaaagata tacgattgtg gaaatcattg   1440
cccatttcca ccaatttgct tgtatacgga ttatgctgtg tatatattac ataacaaatg   1500
tattagtatc atttaatgca cgatttgtga aagggcctga gtttgtattt agcgaatttt   1560
aggttggttt ttttcccttt ttcttctttc agtgcgcttg ctagtcaatc ccatactata   1620
```

```
agccgtgatc attttttgtt tatgtctcat aatataaggc acatctcact acacacgttt    1680
atcgatgcag tgatatatag ggaattaaat acaattttg gtttt                     1725

<210> SEQ ID NO 30
<211> LENGTH: 1216
<212> TYPE: DNA
<213> ORGANISM: Hordeum vulgare

<400> SEQUENCE: 30
cggacgaggg gatcaaacag acctgacttc gactgtagaa gtactgaaga aaccgaggct      60
tggttcatag attcttttga ggaatggcgc aaagcaaaga acctcagtaa ttttatattg     120
ctcggtcatt ctttcggagg atatgttgcg gcaaagtatg cgttacagca tcctgaacat     180
gttcagcact tgattttggt tggttctgct ggcttttcat cagaaacaga tcatagttct     240
gagaggttaa ccaagttccg tgcaacgtgg aaaggcatgc tagtaaacca tctttgggag     300
tccaattgta ctcctcaaag aattgtgaga ggattgggtc cttggggtcc tgatttagtt     360
cggaaatata ccactgctag gtttggctca cattcaacag gtgaattact aacagaacat     420
gagtcctcct tactgacaga ttacatttac cacactttag ctgctaaagc tagtggagag     480
ttgtgcttaa acatattttt ctcattgggg gcatttgcaa ggaaaccact tctgcacagt     540
gcatccgact ggaaagtgcc aactactttc atatatggcc acgatgattg gatgaattac     600 caagggggcgc agcaagcacg caaggacatg aaagttcctt gcgaaatcat cagagtccca     660
cagggaggac attttgtgtt tatagataac cctgagggt tccactcggc gatcttctac     720
gcgtgccgga aattttatc tggagatgca gaggaaggtc tctctcttcc tgatggcttg     780
atatctgcat gaggcgtcat cttgtgtgat ctcgtaccga atagcggtgt cagcataaag     840
caaagctata aacaaataga aatgtttttg tatgtatgaa ttgtgtgaat atgtcattca     900
tatgtgcttg cgtaccaaca acactagtga gacaattatg ttttttttt gcaggtctag     960 acataattat gtcatatatg taagatcttc ctagtcagtt tttaggtcaa gttgctgtaa    1020
gtgatgctct atattcttta agggcaactt tatgtttgcc tgctacgaaa catcttcaca    1080
gtattaactg ccgctgtaca tttgctgcag tcattgctgc gtcgtagcca ttttagaaa     1140 gtattttgga acagtggaag tgcatttgg tgtcttacga tgctattatc ctaccagact    1200
attttgataa aaaaag                                                     1216

<210> SEQ ID NO 31
<211> LENGTH: 1048
<212> TYPE: DNA
<213> ORGANISM: Nicotiana tabacum

<400> SEQUENCE: 31
ctgaagattg gtttattgat tcctttgagg agtggcgcaa agccaaaaac cttagcaact      60
ttattttgct tgggcactct tttggagggt atgtcgctgc aaaatatgct ctcaagcatc     120
cagagcatgt tcagcagttg attctggtag gaccagctgg atttacatca gagactgaac     180
atatgtccga gcggcttacc cagtttagag caacatggaa gggagccgtc ttgaatcatc     240
tgtgggagtc taactttacc ccgatgaaac ttgtcagagg cttaggccca tggggtccag     300
acctagttcg caaatacact aatgctagat ttactgcata ttctaatgga gatagtttga     360
ccgaggagga gtccaggcta ctctcagatt atgtatatca taccttggct gcaaaaccga     420 gtgggggagct atgtttaaaa tatatatttt ccttcggagc atttgccaag agtcctcttt     480
```

```
tatacagagc accagattgg aaggtgccaa cagctttcat atatggatac gaagattgga    540
tgaattatca aggagcggaa caggctagga agaatatgaa ggttccatgt gaaatcttaa    600
gagtccctca ggctggtcac tttgtattta tagacaacac agccgcattc cactctgctg    660
tactctatgc ttgccgtaga tttatctcac cacagaagga caatgaccca cttcctgaag    720
gcttgatatc tgtctgatgg agatacattg ccgtggtgtt ttcattgcgt gtgttgtagg    780
taaatagtgt acaatagcat attagcattg atttaatatt ctctcaaatg tgtttactgg    840
tctgagtaac gtaacttacc agtttctcag aacataatat caatgttaag gaagtcatga    900
atgggtagca ttctgttctt ctgattgttc gttccttgta ggaagtcatg cacagatagg    960
tcgatgattt gtgttcttga aattacatta attttttta tgaatattgt actcaatagt    1020
tacgaaagca ataagatgat gtacaaat                                      1048

<210> SEQ ID NO 32
<211> LENGTH: 1613
<212> TYPE: DNA
<213> ORGANISM: Gossypium hirsutum

<400> SEQUENCE: 32
aaattcaacg ccacccttt aataattcca ttctccctaa taaagtcaaa aatcaaagct      60
tcggtatata aaacgaaaa agaatgttgt attgttaagc aaaagatcga acatcggatg     120
aacagatctg tctatcgttg gtccagctta attttaagaa aaatggccga agaaatcaat     180
aaatccgaga ttcgatcatc cccgtcgatt atagcgaaat ccagatcgtt atggccctcc     240
gttctccgtt ggattcctac ttccactgat catatcatcg cctccgagaa acgccttctc     300
tctctcgtca agactccata tgtgcaagag ctcgtgaata taggttcagg tccgcctggt     360
tctaaggtta ggtggtttcg ttcttcaagt aacgagccga ggttcataaa cacagttacc     420
tttgatagca aggagggttc tcccacccct tgttatggtac acggatatgc tgcttctcaa    480
ggtttctttt tcaagaattt tgattatctt gccaatcgtt tcaaggttat tgctattgat     540
cagcttggtt ggggtggatc aagtaggcct gactttacat gcaaaagcac tgaagaaact     600
gaggcatggt ttattgattc tttggaggag tggctgcaaa gcaaaaaacc ttagtaactt     660
catattactt gggcattctt ttggaggata tgttgcagct aaatatgctc tcaagcatcc     720
tgaacatgtt caacacttaa ttttagtggg gactgctgga cttttcatcag aatcagacac     780 aacatatgag tgggtaaccc gcttcagagc aacatggagg ggggcaattt tgagtcattt     840
gtgggagtct aattttactc ctcagaagat tataagaggc ttaggtcctt ggggtccaga     900
tcttgtacga agtatacag ctgctaggtt tactaacaga tattcacctg agggtgtatt      960
tacagaggag gagtctagac ttctatctga ttatgtgtac catacctcag ctgccaaagc    1020
aagtggagag ctctgcttaa aatatatatt tgcatttgga gcatttaatc gggcactttt    1080
aaacagtgca tctgagtgga aagtgccaac cactttttata tatggggctg aagattggat   1140
gaactaccaa ggagcccaag aagctcgcga gcaaatgaag gtcccatgtg aaattatcag    1200
ggttcctcag ggtggacatt tgtgttcct tgaaaataga gatggattcc attcagctgt     1260
gttgtatgcc tgtaggagat ttcttttcacc taaccctgat aaagaaccct ttcctgaagg   1320
tttggtatca gcatagaaga agcatagtat ttttttaatt tctctccaca tgttgtatgg   1380
cgcattacac cgagtttcat ggccagaag attatttggg taaagaaaaa aacattattt   1440
gcctgtagct tgtatcataa tattttttata tacgtattat gtgttttgta gtaccttgaa  1500
tctggttact ggtttaaggg aatggatatt gaagaattga ttttcaaaaa aaaacaaaat  1560
```
ccatgggggg cccggtccca atcccccaaa ggagtcgttt acaatcaggg cca        1613

<210> SEQ ID NO 33
<211> LENGTH: 862
<212> TYPE: DNA
<213> ORGANISM: Vitis vinifera

<400> SEQUENCE: 33
gtacaagtgc tagatttagt tcatattcaa ctggtgattt gttaactgaa gaggagtcca   60
agttactcac agattatgtg taccatactg tagcagccaa agctagtgga gagctgtgct  120
tgaaatacat attttcattt ggagcgattt gatcggttgc cccttctgca caacgcatca  180
gaatggaaag tgccaaccac ttttatatat ggcttcgaag attggatgaa ctaccaagga  240
gcccaagaag ctcgcaagca atgaaggtc ccatgtgaaa ttattagggt cccccaggct  300
gggcattttg tattcataga caatccctcg ggttccact cggctgtatt gtatgcttgc  360
cgcagatttc tcttgcctga ccctgatagt caatcccttc ctgaaggctt gacatctgcc  420
taaaaataga gtaggctata aattgtaaat tgatagccta tgtataaaaa aaaaacaaaa  480
cattcttcct gcgaagtttg ttggttcata cattcttctg tagttgatga cttcataaga  540
aaattccatt gttcctcaga gaagctatat tctgaacgca tgcataattt aattcagttg  600
ttatgagcgg ttgaatttgc caccggatct tcaacaaatt tcttaaatgc tatttatgag  660
taaatctgaa tttgagggta ccttgtacat gcattgtgac tgaagtaaaa ttcgggttgc  720
ccttccttgt acctctgcat gagagctatg aagagatttt ataattttgg tttatgccct  780
tcattgtaga aaagttcact gttggtataa ttaatgccgc cctcacttgc agctctgcat  840
agtcatgagg gaggaggtat tt                                            862

<210> SEQ ID NO 34
<211> LENGTH: 1560
<212> TYPE: DNA
<213> ORGANISM: Lotus japonicus

<400> SEQUENCE: 34
ccgtttagtg gaatcatcaa ttttcactcc tccatgctct atctgtctgt ctgcaattgc   60
tacacgcttc taatcatgct cacaaatttg aagagacaac atagttagtt aatcctgctc  120
catgaacgca attcggtcgc gttggttggc gacaatggca gaaaacattg gcaaaaccaa  180
tctccaaacc tctgcttctt ctgcaacaac aacatcttcc tcgcttcgtc gtttcttgcc  240
ttctgtcctg cgttggatcc caacttccac cgaccacatc atcaacgccg agaagcgcct  300
cctctctctt gtcaagactc cgtatgttca ggaacaagtt aatataggtt ctggaccacc  360
agattctaga gttaggtggt tccgttccgc gagcaacgag ccacggttta tcaacaccgt  420
cacgtttcaa agtaaagatg acgctcctac gttggtgatg gttcatggat atgccgcgtc  480
acagggtttc ttttccgca actttgatgc tcttgcctct cgtttcagag tcattgctat  540
tgatcaactt ggttggggtg gatctagcag gcctgatttt acatgcaaaa gcactgaaga  600
aactgaggcg tggttcattg attcctttga ggaatggaga aaagccaaaa acctgagcaa  660
ttttatactg gttgggcatt cttttggggg ttatgttgct tccaaatatg cacttaagca  720
cccagagcat gtacaacact tggttctggt gggatctgct ggattttcat cagaaacaga  780
gaggattact aagttcttat cgacttggaa gggatcaatc ctgaagcaaa tatgggattc  840
taatttcaca cctatgaaaa ttatcagagg attaggtcct tggggtcctg atttggtccg  900

| | |
|---|---:|
| caggtataca agtgctagat tttcaactgg ggaaatgctg acagaatctg aatcgacatt | 960 |
| gctgacagat tatctttacc acacaacagc tgccaaacct agtggcgagc tgtgcttaaa | 1020 |
| ctatatattt tcatttggag cattcaccaa gttgccccct cttcaaagtg cctcagagtg | 1080 |
| gaaggtgccc actactttca tatatggtgt ccaagactgg atgaattatg aaggggctca | 1140 |
| agaagctcgc aagcatatga agttccctg tgaaatcatt agggttcccc aggccgggca | 1200 |
| ttttgtgttc atcgaaaacc cgtctggctt ccattcagct gtgtttcatg cttgccggag | 1260 |
| gtttctgagt cctgatcctg acaatgaacc ccttcctgaa gggctaatct ctgcatagag | 1320 |
| tataattttc ttgtgtagtg ctgtctatat ttttatttt tcattttttt gacaaataaa | 1380 |
| attccataat ttaatcaagc catattctag tcttgtaagt tgtaagagca attcaaagaa | 1440 |
| aaaccaactg taatataaat ttgatgtgtg taacatgtgc taattaaaac atgtaattgg | 1500 |
| tttttgtatt attttgtgct atggatgaaa atttagtctt actaatttaa cctctaccat | 1560 |

<210> SEQ ID NO 35
<211> LENGTH: 716
<212> TYPE: DNA
<213> ORGANISM: Glycine max

<400> SEQUENCE: 35

| | |
|---|---:|
| ggtttcgagc aacatggaag ggggcagttt tgaaccatct ttgggaatca aatttcacac | 60 |
| ctcagaaact tgtcaggggt ttaggtcctt ggggtcccaa catagtccgc aagtatacaa | 120 |
| gtgctaggtt tggtacacat tcaactgggg aaatactgac tgaagaggaa tcaacattgc | 180 |
| tgacagacta tgtttaccac acattggcgg ccaaagctag tggagagctg tgcttaaaat | 240 |
| atatttttc atttggagca tttgctagga tgccccttct tctcagtgcc tcagagtgga | 300 |
| aggtgcccac cactttcatg tatggtttcc aagactggat gaattatcaa ggtgcccaag | 360 |
| aagctcgcaa gcatatgaag gttccatgcg aaatcatcag gattcctcag ggtgggcact | 420 |
| ttgcgttcat tgacaaccca actgccttcc attcagctgt tttttatgct tgtcgaaggt | 480 |
| ttcttacacc tgatccagac aatgaatctc ttcctaaagg ctaacctct gcataggtta | 540 |
| ggtcttaatt ttgtgctatt cctgtctata tgtatttaa tattttttt tactaattaa | 600 |
| atttcataat tgaatgaaat catatgtata ttgtttcagt aaagtggaat ttactgaaaa | 660 |
| tatttgtaat agcaacttca acaaaaatcg atttgtagga gaaatttctt ccctgg | 716 |

<210> SEQ ID NO 36
<211> LENGTH: 1480
<212> TYPE: DNA
<213> ORGANISM: Medicago sp.

<400> SEQUENCE: 36

| | |
|---|---:|
| ggttggctca tagttccttt tacctgttga aaacaaaaca tatggagtaa cattttagtc | 60 |
| agaaattcaa agctacgcac ttgattaaac taattatcga aaatggcgg aagaaattag | 120 |
| acaaaaggac gacgtcgatt catcttcgaa atctaaaagc ttctggtctt cactccgttg | 180 |
| gattcccact tctaccgatc atatcatcgc cgctgagaaa cgccttcttt ccattatcaa | 240 |
| gactgggtat gctcaagagc atgttaatat aggttctggt cctcctggct ctaaagttag | 300 |
| atggttccgt tcaaccagta acgagccacg ctttctcaac actgttacat tgatagtaa | 360 |
| acccgattct cctacacttg ttatggttca tggatacgct gcttctcagg gtttcttctt | 420 |
| tcgcaatttt gatgctctcg cctctcgttt cagaatcatt gctgttgatc aacttggttg | 480 |
| gggaggatca agcagacctg atttcacatg caaaagtacc gaagaaactg aggcatggtt | 540 |

```
cattgattct tcgaggaat ggagaaaagc caaaaatctt accaatttca tactgcttgg      600
acattctttt ggtggttatg ttgcttccaa atacgcgctc aagcaccctc agcacgtaca      660
acacttaatt ttggtgggac ctgccgggtt tacagaagaa acagatccaa agactgagtt      720
tgttactaag tttcgagcaa catggaaggg agcagttctg aaccatctat gggaatctaa      780
ttttacacct cagaaaattg tcagaggttt aggtccttgg ggtcctaaca tggtccgcaa      840
atatacaagt gctaggtttg gtacacattc aaccgggcaa aaactgattg acgaggaatc      900
aagtctgctg actgattatg tttatcatac attggcggcc aaagctagtg gggagctgtg      960
tttaaaatat atttttgcat ttggagcatt tgctaggatg ccccttcttc aaagtgctca     1020
agagtggaag gtgcccacca cattcatata tggttacgaa gattggatga attatgaagg     1080
tgcccaagaa gctcgcaagc atatgaaggt tccatgtgaa attatcaggg tccctaaggc     1140
cggccatttt gtgttcattg acaacccaag tggcttccat tcagctgtgt tttatgcttg     1200
tcgaaggttt cttaccccaa attcggacaa tgaatctctt cccgaagggc tatcgtctgc     1260
ttaggattta attttgcatc aatccagtgt atattaatat ggttattaat ttttttttac     1320
ttcataactg aatgaagccg tgtcttgttt ctcagtgaag tggaatataa tggaaatata     1380
tgtaattgta ataacaataa tattgatttg ttggggaact ttgaggacaa aaacatattc     1440
tggtaaaatt tgttgcaca tgcgacaaac atatgctgtg                            1480
```

<210> SEQ ID NO 37
<211> LENGTH: 1029
<212> TYPE: DNA
<213> ORGANISM: Arabidopsis thaliana

<400> SEQUENCE: 37

```
atgaacttga gccgttttgc ttcgagatta agaatggcgg aagaaatctc aaagacgaag       60
gtgggatctt cttctactgc ttcggtggct gattcatctg ctgctgcgtc ggctgcaacg      120
aatgcggcca atcaagatg gaaaattttg tggcctaatt cgctccggtg gattcctacg      180
tccaccgatt acatcatcgc cgccgagaaa cgtcttctct ccatcctcaa gacgccttat      240
gtacaagagc aagtcagtat tggttcagga ccaccaggtt ctaaaatcag gtggtttagg      300
tctacgagca atgagtcacg ttacatcaac actgttacat tgatgccaa ggagggagct       360 cctacactcg tcatggttca tggttatggt gcttctcaag ggtttttctt ccgtaatttt      420
gatgctcttg ccagtcgatt tagagtgatc gctattgatc aacttgggtg gggtggttca      480
agtaggccta atttacatg tagaagcaca gaagaaactg aggcatggtt tatcgactcc       540
tttgaggaat ggcgtaaagc ccagaatctc agtaacttta ttctattagg acattctttt      600
ggaggctatg ttgctgctaa atacgcgctt aagcatcctg aacatgttca acacttaatt      660
ctggtgggat ctgctgggtt ctcagcagaa gcagatgcca atcagaatg gctcactaaa       720 tttagagcaa catggaaagg tgcagtccta aatcatttat gggagtcaaa tttcactcct      780
cagaagctgg ttagaggatt aggtccttgg ggtccaggtc ttgtaaatcg gtatacaact      840
gcaagatttg gtgcacattc ggagggaact gggctaacag aagaggaagc caaattgcta      900
accgattatg tgtaccatac tttggctgca aaggctagtg gagagttatg cttgaaatac      960
atcttctcat ttggagcatt tgctaggaag cccctcttac aaaggtatgt ccaccaaaaa     1020
cattgctga                                                             1029
```

<210> SEQ ID NO 38

<211> LENGTH: 342
<212> TYPE: PRT
<213> ORGANISM: Arabidopsis thaliana

<400> SEQUENCE: 38

```
Met Asn Leu Ser Arg Phe Ala Ser Arg Leu Arg Met Ala Glu Glu Ile
1               5                   10                  15

Ser Lys Thr Lys Val Gly Ser Ser Thr Ala Ser Val Ala Asp Ser
            20                  25                  30

Ser Ala Ala Ser Ala Ala Thr Asn Ala Ala Lys Ser Arg Trp Lys
        35                  40                  45

Ile Leu Trp Pro Asn Ser Leu Arg Trp Ile Pro Thr Ser Thr Asp Tyr
50                  55                  60

Ile Ile Ala Ala Glu Lys Arg Leu Leu Ser Ile Leu Lys Thr Pro Tyr
65                  70                  75                  80

Val Gln Glu Gln Val Ser Ile Gly Ser Gly Pro Pro Gly Ser Lys Ile
                85                  90                  95

Arg Trp Phe Arg Ser Thr Ser Asn Glu Ser Arg Tyr Ile Asn Thr Val
                100                 105                 110

Thr Phe Asp Ala Lys Glu Gly Ala Pro Thr Leu Val Met Val His Gly
            115                 120                 125

Tyr Gly Ala Ser Gln Gly Phe Phe Arg Asn Phe Asp Ala Leu Ala
130                 135                 140

Ser Arg Phe Arg Val Ile Ala Ile Asp Gln Leu Gly Trp Gly Gly Ser
145                 150                 155                 160

Ser Arg Pro Asp Phe Thr Cys Arg Ser Thr Glu Glu Thr Glu Ala Trp
                165                 170                 175

Phe Ile Asp Ser Phe Glu Glu Trp Arg Lys Ala Gln Asn Leu Ser Asn
            180                 185                 190

Phe Ile Leu Leu Gly His Ser Phe Gly Gly Tyr Val Ala Ala Lys Tyr
        195                 200                 205

Ala Leu Lys His Pro Glu His Val Gln His Leu Ile Leu Val Gly Ser
    210                 215                 220

Ala Gly Phe Ser Ala Glu Ala Asp Ala Lys Ser Glu Trp Leu Thr Lys
225                 230                 235                 240

Phe Arg Ala Thr Trp Lys Gly Ala Val Leu Asn His Leu Trp Glu Ser
                245                 250                 255

Asn Phe Thr Pro Gln Lys Leu Val Arg Gly Leu Gly Pro Trp Gly Pro
            260                 265                 270

Gly Leu Val Asn Arg Tyr Thr Thr Ala Arg Phe Gly Ala His Ser Glu
        275                 280                 285

Gly Thr Gly Leu Thr Glu Glu Glu Ala Lys Leu Leu Thr Asp Tyr Val
290                 295                 300

Tyr His Thr Leu Ala Ala Lys Ala Ser Gly Glu Leu Cys Leu Lys Tyr
305                 310                 315                 320

Ile Phe Ser Phe Gly Ala Phe Ala Arg Lys Pro Leu Leu Gln Arg Tyr
                325                 330                 335

Val His Gln Lys His Cys
            340
```

<210> SEQ ID NO 39
<211> LENGTH: 27
<212> TYPE: DNA
<213> ORGANISM: Artificial sequence
<220> FEATURE:
<223> OTHER INFORMATION: Synthetic primer

```
<400> SEQUENCE: 39
atgaacttga gccgttttgc ttcgaga                                          27

<210> SEQ ID NO 40
<211> LENGTH: 24
<212> TYPE: DNA
<213> ORGANISM: Artificial Sequence
<220> FEATURE:
<223> OTHER INFORMATION: Synthetic primer

<400> SEQUENCE: 40
aaccaatcgt agaccatcta ggag                                             24

<210> SEQ ID NO 41
<211> LENGTH: 24
<212> TYPE: DNA
<213> ORGANISM: Artificial Sequence
<220> FEATURE:
<223> OTHER INFORMATION: Synthetic primer

<400> SEQUENCE: 41
gcaatgtttt tggtggacat acct                                             24
```